United States Patent
Siemer et al.

(10) Patent No.: US 10,660,672 B2
(45) Date of Patent: May 26, 2020

(54) EXTERNAL FIXATION SYSTEM

(71) Applicant: Integra LifeSciences Corporation, Plainsboro, NJ (US)

(72) Inventors: Michael Siemer, Orlando, FL (US); Brian Schumacher, Orlando, FL (US); James Spitler, Orlando, FL (US); Paul Cooper, Potomac, MD (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 52 days.

(21) Appl. No.: 15/947,368

(22) Filed: Apr. 6, 2018

(65) Prior Publication Data
US 2018/0353212 A1    Dec. 13, 2018

Related U.S. Application Data

(63) Continuation of application No. 14/849,163, filed on Sep. 9, 2015, now Pat. No. 9,936,975.
(Continued)

(51) Int. Cl.
*A61B 17/62* (2006.01)
*A61B 17/64* (2006.01)
*A61B 17/66* (2006.01)

(52) U.S. Cl.
CPC .......... *A61B 17/62* (2013.01); *A61B 17/6416* (2013.01); *A61B 17/66* (2013.01)

(58) Field of Classification Search
CPC ................................ A61B 17/62; A61B 17/66
See application file for complete search history.

(56) References Cited

U.S. PATENT DOCUMENTS

| 2,625,934 A | 1/1953 | Halliday |
| 2,838,948 A | 6/1958 | Lassy |

(Continued)

FOREIGN PATENT DOCUMENTS

| CA | 2633944 A1 | 7/2007 |
| EP | 2052756 A1 | 4/2009 |

(Continued)

OTHER PUBLICATIONS

Synthes®, Monolateral External Fixation System for Trauma and Orthopaedics, Surgical Technique, 2004, Synthes, Switzerland.
(Continued)

*Primary Examiner* — Ellen C Hammond
(74) *Attorney, Agent, or Firm* — Middleton Reutlinger; Robert H. Eichenberger; Chad D. Bruggeman

(57) ABSTRACT

In embodiments of the invention, there is provided an external fixation system comprising a first plate and a second plate and connectors therebetween. Some or all of the connectors may be adjustable in length or angular position or both. Angular adjustment may comprise a fixed amount of friction and an adjustable amount of friction, and the permitted angular deflection can vary around the perimeter of the angular joint. An adjustable-length connector may comprise a tiltable nut that can either engage or not engage a threaded rod to provide both coarse adjustment and fine adjustment. Tactile or audible feedback may be provided. Other accessories may include: provisional alignment clamps to position parts of the patient's body; a K-wire alignment guide; a K-wire support post; a universal fixation bolt; a plurality of half-pins that can be used with a common support post or block; and a resilient retention device.

16 Claims, 34 Drawing Sheets

Related U.S. Application Data

(60) Provisional application No. 62/048,074, filed on Sep. 9, 2014.

(56) References Cited

U.S. PATENT DOCUMENTS

| | | | |
|---|---|---|---|
| 4,475,546 A | 10/1984 | Patton | |
| 4,799,496 A | 1/1989 | Hargreaves et al. | |
| 4,915,627 A | 4/1990 | Hirdes | |
| 5,062,844 A | 11/1991 | Jamison et al. | |
| 5,087,258 A | 2/1992 | Schewior | |
| 5,152,280 A | 10/1992 | Danieli | |
| 5,325,868 A | 7/1994 | Kimmelstiel | |
| 5,451,225 A | 9/1995 | Ross, Jr. et al. | |
| 5,458,599 A * | 10/1995 | Adobbati | A61B 17/7225 606/54 |
| 5,540,686 A | 7/1996 | Zippel et al. | |
| 5,601,551 A | 2/1997 | Taylor et al. | |
| 5,630,814 A | 5/1997 | Ross, Jr. et al. | |
| 5,653,707 A | 8/1997 | Taylor et al. | |
| 5,662,650 A | 9/1997 | Bailey et al. | |
| 5,681,309 A | 10/1997 | Ross, Jr. et al. | |
| 5,688,271 A | 11/1997 | Faccioli et al. | |
| 5,690,633 A | 11/1997 | Taylor et al. | |
| 5,693,015 A | 12/1997 | Walker et al. | |
| 5,702,389 A | 12/1997 | Taylor et al. | |
| 5,728,095 A | 3/1998 | Taylor et al. | |
| 5,766,173 A | 6/1998 | Ross, Jr. et al. | |
| 5,776,132 A | 7/1998 | Blyakher | |
| 5,797,908 A | 8/1998 | Meyers et al. | |
| 5,863,292 A | 1/1999 | Tosic | |
| 5,891,143 A | 4/1999 | Taylor et al. | |
| 5,928,230 A | 7/1999 | Tosic | |
| 5,931,837 A | 8/1999 | Marsh et al. | |
| 5,968,043 A | 10/1999 | Ross, Jr. et al. | |
| 5,971,984 A | 10/1999 | Taylor et al. | |
| 5,997,537 A | 12/1999 | Walulik | |
| 6,030,386 A * | 2/2000 | Taylor | A61B 17/62 606/54 |
| 6,033,414 A | 3/2000 | Tockman et al. | |
| 6,217,577 B1 | 4/2001 | Hoffmann | |
| 6,277,118 B1 | 8/2001 | Grant et al. | |
| 6,277,119 B1 | 8/2001 | Walulik et al. | |
| 6,355,037 B1 | 3/2002 | Crosslin et al. | |
| 6,500,177 B1 | 12/2002 | Martinelli et al. | |
| 6,520,961 B1 | 2/2003 | Marsh | |
| 6,533,772 B1 | 3/2003 | Sherts et al. | |
| 6,537,275 B2 | 3/2003 | Venturini et al. | |
| 6,678,562 B1 | 1/2004 | Tepper et al. | |
| 6,689,138 B2 | 2/2004 | Léchot et al. | |
| 6,860,883 B2 * | 3/2005 | Janowski | A61B 17/645 606/56 |
| 6,964,663 B2 | 11/2005 | Grant et al. | |
| 7,004,943 B2 | 2/2006 | Ferrante et al. | |
| 7,048,735 B2 | 5/2006 | Ferrante et al. | |
| 7,226,449 B2 | 6/2007 | Venturini et al. | |
| 7,261,713 B2 | 8/2007 | Langmaid et al. | |
| 7,306,601 B2 | 12/2007 | McGrath et al. | |
| 7,311,711 B2 | 12/2007 | Cole | |
| 7,361,176 B2 | 4/2008 | Cooper et al. | |
| 7,422,593 B2 | 9/2008 | Cresina et al. | |
| 7,449,023 B2 | 11/2008 | Walulik et al. | |
| 7,465,303 B2 | 12/2008 | Riccione et al. | |
| 7,468,063 B2 | 12/2008 | Walulik et al. | |
| 7,588,571 B2 | 9/2009 | Olsen | |
| 7,608,074 B2 | 10/2009 | Austin et al. | |
| 7,632,271 B2 | 12/2009 | Baumgartner et al. | |
| 7,749,224 B2 | 7/2010 | Cresina et al. | |
| 7,758,582 B2 | 7/2010 | Ferrante et al. | |
| 7,806,843 B2 | 10/2010 | Marin | |
| 7,815,586 B2 | 10/2010 | Grant et al. | |
| 7,831,297 B2 | 11/2010 | Opie et al. | |
| 7,887,498 B2 | 2/2011 | Marin | |
| 7,955,334 B2 | 6/2011 | Steiner et al. | |
| 7,985,221 B2 | 7/2011 | Coull et al. | |
| 8,002,773 B2 | 8/2011 | Kehres et al. | |
| 8,016,830 B2 | 9/2011 | Veldman et al. | |
| 8,029,505 B2 * | 10/2011 | Hearn | A61B 17/66 606/56 |
| 8,038,628 B2 | 10/2011 | Von Malmborg et al. | |
| 8,057,474 B2 | 11/2011 | Knuchel et al. | |
| 8,062,293 B2 | 11/2011 | Steiner et al. | |
| 8,080,016 B2 | 12/2011 | Moorcroft et al. | |
| 8,096,998 B2 | 1/2012 | Cresina | |
| 8,192,434 B2 | 6/2012 | Huebner et al. | |
| 8,202,273 B2 | 6/2012 | Kardis | |
| 8,257,353 B2 | 9/2012 | Wong | |
| 8,377,060 B2 | 2/2013 | Vasta et al. | |
| 8,419,733 B2 | 4/2013 | Hajianpour | |
| 8,425,512 B2 | 4/2013 | Vasta et al. | |
| 8,425,521 B2 | 4/2013 | Cremer et al. | |
| 8,439,914 B2 | 5/2013 | Ross et al. | |
| 8,444,644 B2 | 5/2013 | Ross et al. | |
| 8,454,604 B2 | 6/2013 | Wong | |
| 2002/0010465 A1 | 1/2002 | Koo et al. | |
| 2004/0073212 A1 | 4/2004 | Kim | |
| 2005/0015087 A1 | 1/2005 | Walulik et al. | |
| 2006/0184169 A1 | 8/2006 | Stevens | |
| 2007/0161984 A1 | 7/2007 | Cresina et al. | |
| 2007/0233061 A1 | 10/2007 | Lefhmann et al. | |
| 2007/0255280 A1 | 11/2007 | Austin et al. | |
| 2008/0132817 A1 | 6/2008 | Vito | |
| 2008/0139978 A1 | 6/2008 | Talish et al. | |
| 2008/0269741 A1 | 10/2008 | Karidis | |
| 2008/0300606 A1 | 12/2008 | Moorcroft et al. | |
| 2009/0036890 A1 | 2/2009 | Karidis | |
| 2009/0036892 A1 | 2/2009 | Karidis et al. | |
| 2009/0082709 A1 | 3/2009 | Marin | |
| 2009/0131935 A1 | 5/2009 | Yeager | |
| 2009/0177197 A1 | 7/2009 | Marin | |
| 2009/0177198 A1 * | 7/2009 | Theodoros | A61B 17/62 606/56 |
| 2009/0326532 A1 | 12/2009 | Schulze | |
| 2010/0179548 A1 | 7/2010 | Marin | |
| 2010/0191239 A1 | 7/2010 | Sakkers et al. | |
| 2010/0234844 A1 | 9/2010 | Edelhauser et al. | |
| 2010/0305568 A1 | 12/2010 | Ross et al. | |
| 2010/0312243 A1 | 12/2010 | Ross et al. | |
| 2010/0318084 A1 | 12/2010 | Hajianpour | |
| 2010/0331840 A1 | 12/2010 | Ross et al. | |
| 2011/0118737 A1 | 5/2011 | Vasta et al. | |
| 2011/0196380 A1 | 8/2011 | Cremer et al. | |
| 2011/0208187 A1 | 8/2011 | Wong | |
| 2011/0245830 A1 | 10/2011 | Zgonis et al. | |
| 2011/0301610 A1 | 12/2011 | Ali et al. | |
| 2012/0041439 A1 | 2/2012 | Singh et al. | |
| 2012/0143190 A1 | 6/2012 | Wolfson | |
| 2012/0184958 A1 | 7/2012 | Knuchel et al. | |
| 2012/0253410 A1 * | 10/2012 | Taylor | A61B 17/6458 606/329 |
| 2012/0303028 A1 | 11/2012 | Wong | |
| 2012/0303029 A1 | 11/2012 | Vasta et al. | |
| 2013/0103001 A1 | 4/2013 | BenMaamer et al. | |
| 2013/0123784 A1 | 5/2013 | Ross et al. | |
| 2013/0131675 A1 | 5/2013 | Vasta et al. | |
| 2016/0066956 A1 | 3/2016 | Siemer et al. | |

FOREIGN PATENT DOCUMENTS

| | | |
|---|---|---|
| ES | 2012188 | 3/1990 |
| JP | 3732485 B2 | 1/2006 |
| WO | 199730650 A1 | 8/1997 |
| WO | 9857686 A1 | 12/1998 |
| WO | 2005094936 A2 | 10/2005 |
| WO | 2006124580 A1 | 11/2006 |
| WO | 2012102685 A1 | 8/2012 |

OTHER PUBLICATIONS

EBI, Trauma Products, Reconstruction Products, Catalog, 2002, EBI, New Jersey.

(56) References Cited

OTHER PUBLICATIONS

Zimmer Trauma, TransFx® External Fixation System Large and Intermediate Surgical Technique, 97-4450-002-01 Rev. 3 1004-T28 May 20, 2010, 2010, Zimmer, Inc. LL, Indiana.

BIOMET® Trauma, Biomet Multi-Axial Correction (MAC) System, Surgical Technique, Biomet Orthopedics, Form No. BMT0331.0-Eng, Rev0111513, 2013, Warsaw, Indiana.

Smith & Newphew, Tibiotalocalcaneal Arthrodesis with the ILIZAROV Method, 7108-0983 Rev0 May 2010, 2010, Smith & Nephew, Inc., Memphis, Tennessee.

Stryker, Hoffmann II Lower Extremity Ring System, Operative Technique, 2010, Stryker, Mahwah, New Jersey.

Synthes®, The Distraction Osteogenesis Ring System. Length correction frames, Technique Guide, 2008 Synthes, Inc., West Chester, Pennsylvania.

Wright, Sidekick® Freedom™ Circular Fixator, Surgical Technique, 2010, Wright Medical Technology, Inc., Arlington, Tennessee.

Biomet® Vision™ FootRing™ System, Fixation in a Snap, Surgical Technique, 2013, Form No. BMET0355.0, Rev011513, Biomet Orthopedics, Warsaw, Indiana.

DePuy Trauma, TempFix™ External Fixation System, Surgical Technique Spanning the Ankle Joint Half Pin and Transfixing Pin Techniques, 2010 DuPuy Orthopaecis, Inc., Warsaw, Indiana.

DePuy, Johnson-Johnson Company, Ace-Fischer® External Fixation System Construct Guide, Created for Support. Designed for Versatility, 2004 DePuy Orthopaedics, Inc., Warsaw, Indiana.

SBi Small Bone Innovations, Inc., RingFIX™ RAD, Surgical Technique Rozbruch Ankle Distraction, 2008 Small Bone Innovations, Inc., Morrisville, Pennsylvania.

Orthofix®, Truelok Parts Reference Guide Truelok™ Ring Fixation System, TL-0910 PL-US, Sep. 2009, Orthofix, Inc., Lewisville, Texas.

Orthofix®, Sheffield Ring Fixator, Consider all the Angles, SR-01005-SS, 2002 Orthofix, Inc., Lewisville, Texas.

SBi Small Bone Innovations, Inc., RingFIX™ Foot and Ankle Fixation System, Frame Assembly and Application Just Got a Whole Lot Easier, RingFIX™ Multi-hole Footplates and Tab Rings, Raising Expectations for Lower Limb Surgery, MKT 20120 Rev C, 2007, Small Bone Innovations, Inc., Morrisville, Pennsylvania.

Smith & Newphew, Jet-X Bar Unilateral Fixator, Ankle Spanning, Metaphyseal/Diaphyseal, Optional Cannulated and Hybrid Surgical Technique, 30036403003a 7108-0633, Jan. 2007, Memphis, Tennessee.

Orthofix®, Prepared with Prefix, PF-0401(a)-PL-US, Nov. 2004, Orthofix, Inc., Lewisville, Texas.

Smith & Newphew, Foot and Ankle Solution from smith&nephew, Making strides toward effective diabetic foot treatment, 7118-1761 REV0.2, 2011 Smith & Nephew, Inc., Cordova, Tennessee.

Simard, S.; Marchant, M.; and Mencio, G., "The Ilizaroz Procedure: Limb Lengthening and Its Implications", 1992, Physical Therapy, 72(1), 25-34.

Gardner, T. N.; Hardy, J. R. W.; Evans, M.; Richardson, J.B., and Kenwright, J, The static and dynamic behavior of tibial fractures due to unlocking external fixators, vol. 11, No. 8, 425-430, 1996 Elsevier Science Limited, Clinical Biomechanics, Great Britain.

Baidya, Krishna P.; Ramakrishna, Seeram; Ritchie, A. and Rahman, M., Advanced Textile Composite External Fixator Ring, Department of Mechanical and Production Engineering, National University of—Singapore, Singapore-119260, Institute of Materials Research and Engineering, National University of Singapore, Singapore-19260.

Cunningham, J.L.; Evans, M.; and Kenwright, J., Measurement of fracture movement in patients treated with unilateral external skeletal fixation, Mar. 1989, 11(2): 118-22, Oxford Orthopaedic Engineering Centre, University of Oxford, UK, J Biomed Eng.

DiDomenico, Lawrence A.; Ziran, Bruce H.; and Cane, Laurence Zachary, The Use of External Fixation in the Lower Extremity, A. Saxena (ed.), International Advances in Foot and Ankle Surgery, 2012, DOI: 10.1007/978-0-85729-609-2_41, Springer, London, 439-452.

Kershaw, C. J.; Cunningham, J. L.; Kenwright, J., Tibial external fixation, weight bearing, and fracture movement, Leicester Royal Infirmary, Aug. 1993; (293), 28-36, Clinical Orthopaedics and Related Research, England.

Chao, E.Y.; Aro, H.T.; Lewallen, D.G.; Kelly, P.J., The effect of rigidity on fracture healing in external fixation, Apr. 1989 ; (241); 24-35, Clinical Orthopaedics and Related Research, Mayo Clinic Rochester, Minnesota.

Antoci, MD, PHD, Valentin; Voor, PHD, Michael J.; Antoci, Jr., BS, Valentin; and Roberts, MD, Craig S., Effect of Wire Tension on Stiffness of Tensioned Fine Wires in External Fixation: A Mechanical Study, Sep. 2007, 36(9), 473-476, The American Journal of Orthopedics, Louisville, Kentucky.

E Mešić, A Muminović, N Repčić, Structural Analysis and Experimental Testing of External Fixator System Under Axial Compression, 13th International Research/Expert Conference, "Trends in the Development of Machinery and Associated Technology" TMT 2009, Oct. 16-21, 2009, 497-500, Hammamet, Tunisia.

Catagni, M.D., Maurizio A., Atlas for the Insertion of Transosseous Wires and Half-Pins, Ilizarov Method, Copyright 2003 Medi Surgical Video, First edition 2002, Second revised edition 2003, Department of Medicalplastics srl, Via Mercadante, 15—20124 Milan—Italy.

Kenwright, J.; Richardson, J.B.; Cunningham, J.L.; White, S. H.; Goodship, A.E.; Adams, M.A.; Magnussen, P.A.; Newman, J.H., Axial Movement and Tibial Fractures, A Controlled Randomised Trial of Treatment, Journal of Bone and Joint Surgery, vol. 73-B, No. 4, 654-659, Jul. 1991, Nuffield Orthopaedic Center, Oxford and Bristol Royal Infirmary.

Easley MD, Mark; Looney MD, Colin; Wellman MD, Samuel; and Wilson MD, Joseph, Ankle Arthrodesis Using Ring External Fixation, Techniques in Foot and Ankle Surgery, 150-163, 2006 Lippincott Williams, Wilkins, Philadelphia, Pennsylvania.

Fragomen MD, Austin T.; Rozbruch MD, S. Robert, The Mechanics of External Fixation, 2007, 3: 13-29, HSS Journal, New York, New York.

Taylor MD, J. Charles, Correction of General Deformity with the Taylor Spatial Frame Fixator™, 2002, Memphis, Tennessee.

Huiskes, R; Chao, E.Y., Guidelines for external fixation frame rigidity and stresses, 1986; 4(1); 68-75, Journal of Orthopaedic Research.

Gardner, T.N.; Evans, M; Kenwright, J., The influence of external fixators on fracture motion during simulated walking, Oxford Orthopaedic Engineering Centre, University of Oxford, Nuffield Orthopaedic Centre, Heading, UK, Med Eng Phys, 18(4); 305-13, Jun. 1996 , Oxford Orthopaedic Engineering Centre, University of Oxford, Nuffield Orthopaedic Center, Headington, UK.

\* cited by examiner

EXTERNAL FIXATION SYSTEM

CLAIM TO PRIORITY

This utility patent application is a continuation of, and claims priority to and benefit under 35 U.S.C. § 120 to copending U.S. application Ser. No. 14/849,163, filed Sep. 9, 2015, which claims priority to and benefit under 35 U.S.C. § 119(e) to U.S. Provisional Application No. 62/048,074, filed on Sep. 9, 2014, the entire contents of which are hereby incorporated by reference.

TECHNICAL FIELD

This patent application pertains to orthopedic surgery.

BACKGROUND

External Fixation Devices are utilized to stabilize bone fractures. Such devices can also be utilized to either compress or distract bones to the desired alignment and length, and can also be used for correction of deformity. Although such devices have been in use for some time, there remains opportunity for improvement in certain aspects such as ease of use and ease of adjustment during and after surgery.

SUMMARY OF THE INVENTION

In an embodiment of the invention, there may be provided two plates (which may be full rings or may be shapes that are less than full rings, in which a plate may comprise an outrigger shape on its perimeter, and in which the outrigger has both a hole and a slot. In an embodiment of the invention, there may be provided a footplate and a rocker bottom, such that the rocker bottom connects to the footplate at places that are not part of a regularly repeating pattern of holes in the footplate.

In an embodiment of the invention, there may be provided a first plate and a second plate and connectors therebetween. The connectors may be of different lengths and may have different numbers or types of degrees of freedom respectively. It is possible to use connectors having different numbers or types of degrees of freedom together with each other in the same apparatus. Degrees of freedom can include length adjustment and can include angular adjustment of an angularly adjustable joint.

In an embodiment of the invention, there may be provided, for engaging a threaded rod with a plate, a speed-nut that is threadedly engaged with the threaded rod when the speed-nut is axially aligned with the threaded rod, and is disengaged when the speed-nut is tilted with respect to the threaded rod.

In an embodiment of the invention, there may be provided a connector having an angularly adjustable joint that is a ball-and-socket joint. In an embodiment of the invention, there may be provided a connector having an angularly-adjustable joint that has a non-user-adjustable frictional bearing component. In an embodiment of the invention, there may be provided a connector having an angularly-adjustable joint that has a user-adjustable frictional bearing component. In an embodiment of the invention, there may be provided a connector having an angularly-adjustable joint that has first and second frictional bearing components.

In an embodiment of the invention, there may be provided an angularly adjustable joint that has an extent of surrounding the ball, wherein the extent of surrounding the ball is non-uniform around the perimeter. In an embodiment of the invention, there may be provided an angularly adjustable joint that has different limits of permitted angular tilt in different positions around its circumference. In particular, one place along the circumference, a major dip, may be provided that allows up to approximately 90 degrees of angular deflection away from a central axis, while the rest of the circumference allows less than the angle for the major dip. There may also be provided a minor dip, smaller than the major dip, which may be located opposite the major dip. The largest permitted tilt may be in a direction away from the centers of the rings.

In an embodiment of the invention, there may be provided a combination of coarse adjustment and fine adjustment that comprises a tiltable nut that can either engage or not engage a threaded rod. The assembly that comprises the tiltable nut may have certain features such as a slider, and a yoke comprising a pair of extension arms. The slider may have a recess that engages the extension arms. The tiltable nut may further have a dome-bump that can cooperate with a corresponding receiving space. The slider may have a through-slot that engages the extension arms. All of these features may be contained in or inside a housing.

In an embodiment of the invention, this assembly can provide two definite configurations, one of which is an engaged configuration and the other of which is a non-engaged configuration. In the engaged configuration, the assembly can be rotated to produce fine adjustment of the length of the connector. In the non-engaged configuration, the assembly is freely translatable along the threaded rod to allow coarse adjustment. There may also be provided a setscrew for positive locking. The transition between the engaged and the non-engaged configurations may provide feedback to the user about the thread engagement or lack thereof. Such feedback can be tactile or audible or both. Sufficient force moves the tiltable nut between its two defined positions may be less than the force to initially leave either of the two defined positions.

In an embodiment of the invention, there may be provided provisional alignment clamps that attach to the rings or plates, and that contact or bear against various parts of the patient's body for purposes of positioning.

In an embodiment of the invention, there may be provided a K-wire alignment guide. In an embodiment of the invention, there may be provided a K-wire support post. In an embodiment of the invention, there may be provide a tensioning adapter. The tensioning adapter may have a pattern of legs to fit with a plate. There may further be provided an alignment spacer to assist in use of the tensioning adapter.

In an embodiment of the invention, there may be provided a plurality of half-pins that can be used with a common support post or other form of connector. The various half-pins may differ in certain dimensions but may be grasped by the common support post without the need for respective adapters, such as by virtue of the various half-pins having certain dimensions in common with each other.

In an embodiment of the invention, there may be provided a universal fixation bolt that has a side slot and a central hole, both of which are suitable to receive a K-wire.

In an embodiment of the invention, in which the plate or ring comprises an outrigger on its perimeter shape, there may be provided a filler-alignment piece for use in tensioning a K-wire when it is located near an outrigger.

In an embodiment of the invention, there may be provided a retention device that may be mounted on either a K-wire or a half-pin, and may frictionally retain a dressing against a patient's skin. In an embodiment of the invention, there may be provided a retention device that has flaps. Such a device may provide easier motion in one direction than in the opposite direction.

In an embodiment of the invention, there may be provided an external fixation system may include a first plate, a second plate, and a first connector connecting the first plate with the second plate. The first connector may include a lengthwise adjustable member, wherein the lengthwise adjustable member may include a threaded rod having external threads and may include a tiltable nut. The tiltable nut having internal threads on a portion of an internal surface thereof. The lengthwise adjustable member may include a housing that generally surrounds the tiltable nut with the threaded rod being able to pass through at least a portion of the housing. The tiltable nut can occupy a first position in which the internal threads of the tiltable nut engage the external threads of the threaded rod and the tiltable nut can occupy a second position in which the internal threads of the tiltable nut do not engage the external threads of the threaded rod. The tiltable nut may include an extension and the extension may include an engagement feature that cooperates with a complementary feature in the housing to define a position of the tiltable nut. The engagement feature may be a protrusion and the complementary feature may be a hole in the housing. The extension may be a cantilever from the tiltable nut. When the tiltable nut enters the first position or enters the second position, a tactile feedback may be provided or an audible feedback may be provided. In some embodiments, both the tactile feedback and the audible feedback are provided. A slider that extends through the housing and can translate in a direction generally perpendicular to a long direction of the threaded rod, wherein the slider cooperates with the tiltable nut to create or remove tilting of the tiltable nut. The slider may have a through-slot through which the threaded rod may pass in any permitted position of the slider, wherein the slider has a recess that can receive an extension arm of the tiltable nut so that translation of the slider causes the tiltable nut to move between the first position and the second position. The system may include a locking feature that upon actuation both prevents the tiltable nut from moving out of the first position and prevents rotation of the tiltable nut with respect to the threaded rod. The locking feature may include a setscrew that can bear against the tiltable nut to frictionally lock the tiltable nut against the threaded rod. The first connector may further include an angularly adjustable joint including a ball and a housing, wherein the housing may include a socket complementary to the ball, and the angularly adjustable joint further may include a first frictional bearing component that can bear against the ball and a second frictional bearing component that can bear against the ball. One of the frictional bearing components may have a shape of a disc and another of the frictional bearing components may have a shape of a ring, wherein the ring contacts the ball in a ring-shaped region, and wherein the disc contacts the ball at a region that is interiorly with respect to the ring-shaped region. The first frictional bearing component may thread into a first housing thread in the housing, and the second frictional bearing component may thread into a second housing thread in the housing, wherein the second housing thread has a minor diameter that is larger than a major diameter of the first housing thread. Adjustment of the first frictional bearing component may not change, or may be independent of, how the second frictional bearing component bears against the ball. The first connector may further include an angularly adjustable joint comprising a ball and a socket complementary to the ball, wherein the ball has a post extending therefrom, the post having an axis, the socket having a perimeter that limits positions of the post relative to the housing, wherein the post has a central position and an angular displacement, wherein the angular displacement is an angular position of the axis of the post measured relative to the central position, wherein a magnitude of permitted angular displacement is distributed non-uniformly around the perimeter, wherein at some locations around the perimeter, the post can tilt a smaller nonzero angle away from the central position, and at least one location the post can tilt a larger angle away from the central position.

Another embodiment of the invention, there may be provided an external fixation system comprising a first plate, a second plate, and a first connector connecting the first plate with the second plate. The first connector may include a lengthwise adjustable member. The lengthwise adjustable member may include a threaded rod having external threads and may include a tiltable nut, the tiltable nut having internal threads on a portion of an internal surface thereof. The lengthwise adjustable member may include a housing that generally surrounds the tiltable nut, the threaded rod being able to pass through at least a portion of the housing. The tiltable nut can occupy a first position in which the internal threads of the tiltable nut engage the external threads of the threaded rod, and the tiltable nut can occupy a second position in which the internal threads of the tiltable nut do not engage the external threads of the threaded rod. The tiltable nut may include an extension arm. The system may include a slider, the slider being received in the housing and being capable of sliding with respect to the housing. The slider may have a through-slot through which the threaded rod may pass in any permitted position of the slider. The slider has a recess that can receive the extension arm so that translation of the slider causes the tiltable nut to move between the first position and the second position. The tiltable nut may include a pivot axis with the housing. A setscrew may be used that can bear against the tiltable nut to frictionally lock the tiltable nut against the threaded rod. The first connector may further include an angularly adjustable joint comprising a ball and a housing, wherein the housing may include a socket complementary to the ball, wherein the angularly adjustable joint further may include a non-user-adjustable frictional bearing component that bears against the ball or a user-adjustable frictional bearing component that can bear against the ball, wherein the non-user-adjustable frictional bearing component is set so that it exerts force against the ball at all times, and wherein the user-adjustable frictional bearing component can be adjusted by a user so that in a first configuration it exerts no force on the ball and in a second configuration it exerts some force on the ball. The angular adjustable joint further may include both the non-user-adjustable frictional bearing component and the user-adjustable frictional bearing component. The first connector may include an angularly adjustable joint comprising a ball and a housing, wherein the housing may include a socket complementary to the ball, wherein the angular adjustable joint further includes a post extending from the ball, the post having an axis, the post having a central position, the socket having a perimeter, wherein the perimeter, at any particular position around the perimeter, has an extent of enclosing the ball, wherein the extent of enclosing the ball is non-uniform as a function of position around the perimeter.

In an embodiment of the invention, there may be provided an external fixation system comprising a first plate, a second plate, and a first connector connecting the first plate with the second plate. The first connector may include a lengthwise adjustable member, wherein the lengthwise adjustable member may include a threaded rod having external threads and may include a tiltable nut, the tiltable nut having internal threads on a portion of an internal surface thereof. The lengthwise adjustable member may include a housing that generally surrounds the tiltable nut and the threaded rod can pass through at least a portion of the housing. The tiltable nut can occupy a first position in which the internal threads of the tiltable nut engage the external threads of the threaded rod, and the tiltable nut can occupy a second position in which the internal threads of the tiltable nut do not engage the external threads of the threaded rod. When the tiltable nut is in the first position the tiltable nut can be rotated with respect to the threaded rod to provide fine adjustment of a length of the first connector, and when the tiltable nut is in the second position the tiltable nut can be translated with respect to the threaded rod to provide coarse adjustment of the length of the first connector. A locking feature may be included that upon actuation prevents both the tiltable nut from moving out of the first position and prevents rotation of the tiltable nut with respect to the threaded rod. The locking feature may include a setscrew that can bear against the tiltable nut to frictionally lock the tiltable nut against the threaded rod. Motion from the first position to the second position or from the second position to the first position provides audible feedback or tactile feedback. In another embodiment, the first connector may further include an angularly adjustable joint comprising a ball and a housing, wherein the housing may include a socket complementary to the ball, wherein the angularly adjustable joint further may include a non-user-adjustable frictional bearing component that bears against the ball or a user-adjustable frictional bearing component that can bear against the ball, wherein the non-user-adjustable frictional bearing component is set so that it exerts force against the ball at all times, and wherein the user-adjustable frictional bearing component can be adjusted by a user so that in a first configuration it exerts no force on the ball and in a second configuration it exerts some force on the ball. The angular adjustable joint further may include both the non-user-adjustable frictional bearing component and the user-adjustable frictional bearing component. The angular adjustable joint may include a post extending from the ball, the post having an axis, the post having a central position, the socket having a perimeter, wherein the perimeter, at any particular position around the perimeter, has an extent of enclosing the ball, wherein the extent of enclosing the ball is non-uniform as a function of position around the perimeter.

In an embodiment of the invention, there may be provided a kit comprising various of the components described herein, coordinated in ways such that many of the components can be used together with many other of the components.

In an embodiment of the invention, there may be provided methods of use corresponding to various of the components described herein.

BRIEF DESCRIPTION OF THE ILLUSTRATIONS

FIG. 1 is a three-dimensional view of an assembly comprising upper and lower plates and three connectors connecting the plates.

FIG. 2A is a three-dimensional view of the upper plate as shown in FIG. 1. FIG. 2B is a three-dimensional view of the lower plate as shown in FIG. 1. FIG. 2C is a three-dimensional view of an alternative lower plate referred to as a five-eighths plate. FIG. 2D is a three-dimensional view of a half-plate. FIG. 2E is a three-dimensional view of a slightly different half-plate. FIG. 2F is a three-dimensional view of a footplate and rocker bottom, viewed slightly from above. FIG. 2G is a three-dimensional view of a footplate and rocker bottom, viewed slightly from below. FIG. 2H is a three-dimensional view, slightly from above, of a footplate further connected to an anterior half-plate or half-ring also having a crossbar assembly. FIG. 2I is a similar view slightly from below.

FIG. 3A depicts a connector having a length adjustment and two angular adjustments. FIG. 3B depicts a connector having a length adjustment and one angular adjustment. FIG. 3C depicts a connector having only a length adjustment.

Figure 11:
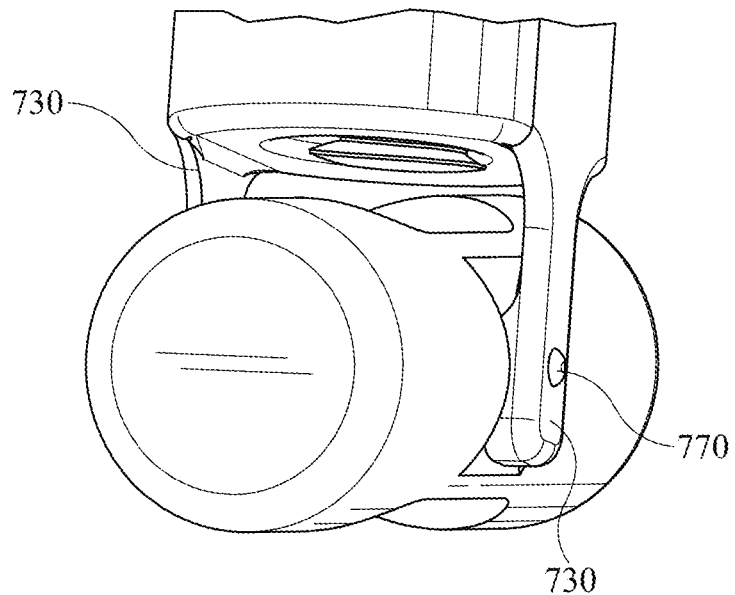
FIG. 11 is a three-dimensional view of the slider and a portion of the tiltable nut including its extension arms.
Figure 13A:
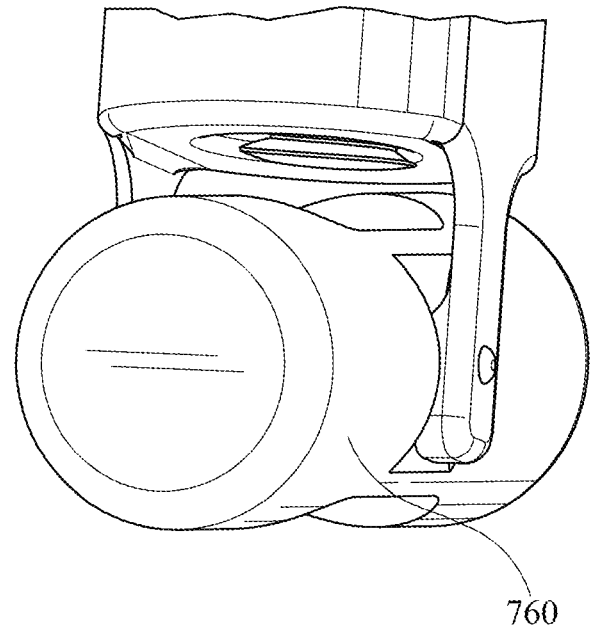
Figure 13B:
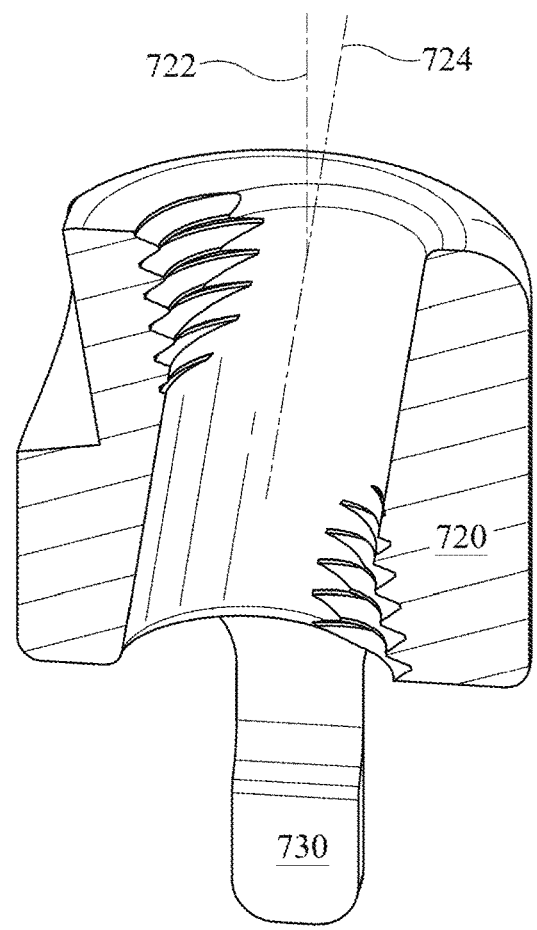
Figure 13C:
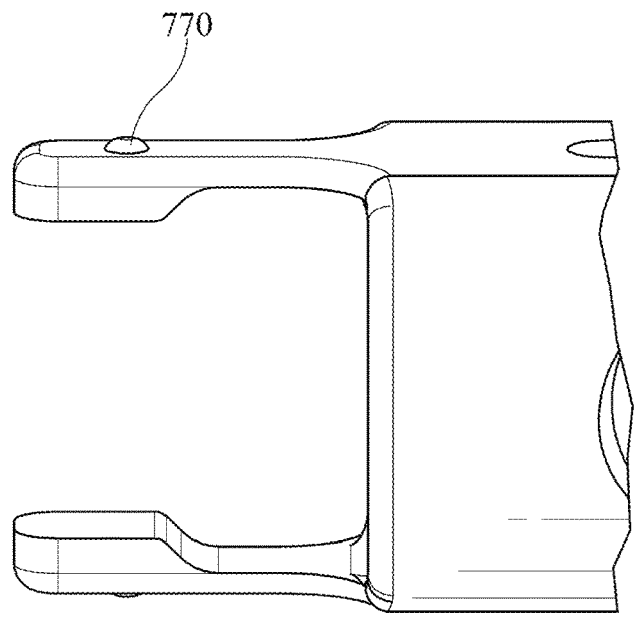

FIG. 13A is a three-dimensional view of the slider and a portion of the tiltable nut including its extension arms, similar to FIG. 11 but shaded. FIG. 13B is a section through the tiltable nut, also showing one extension arm. FIG. 13C is a three-dimensional view of the extension arms, showing the dome-bump.

Figure 14A:
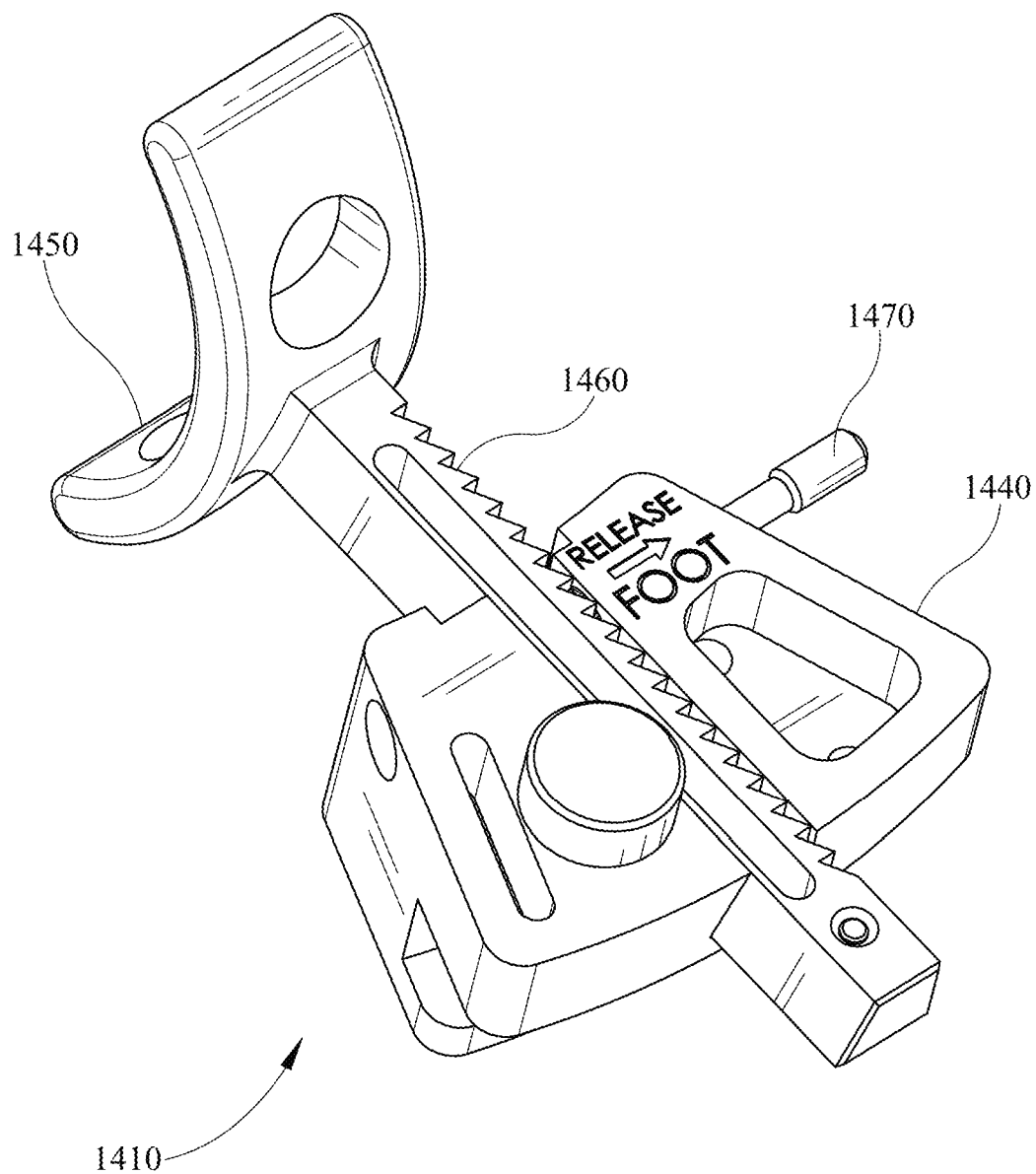
Figure 14B:
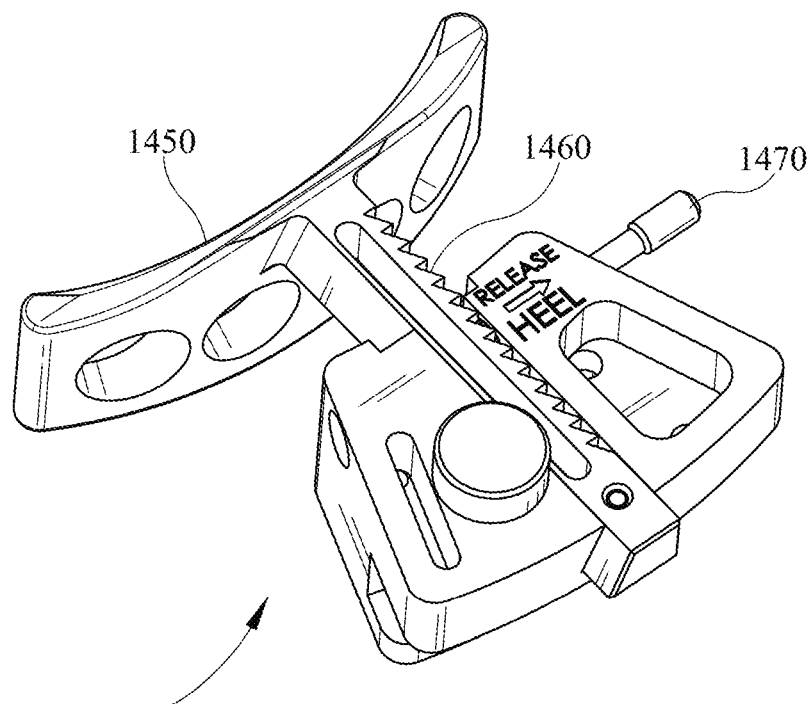
Figure 14C:
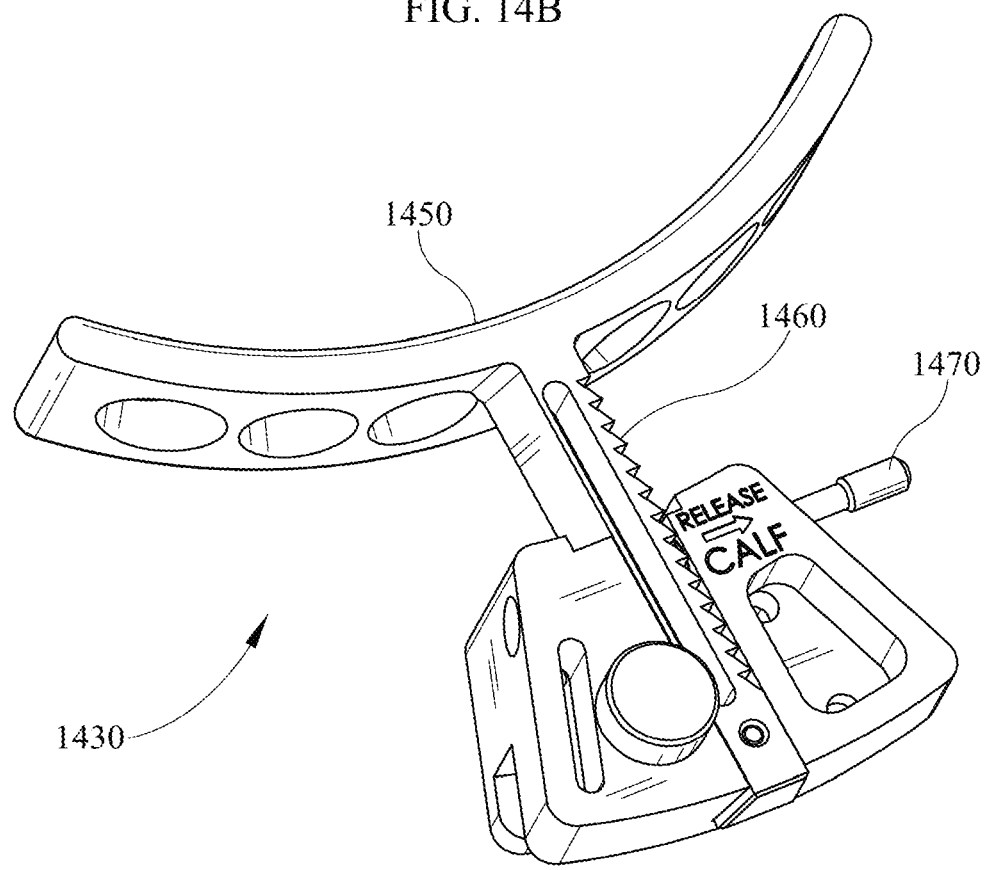

FIG. 14A depicts a provisional alignment clamp for the foot. FIG. 14B depicts a provisional alignment clamp for the heel. FIG. 14C depicts a provisional alignment clamp for the calf.

Figure 15A:
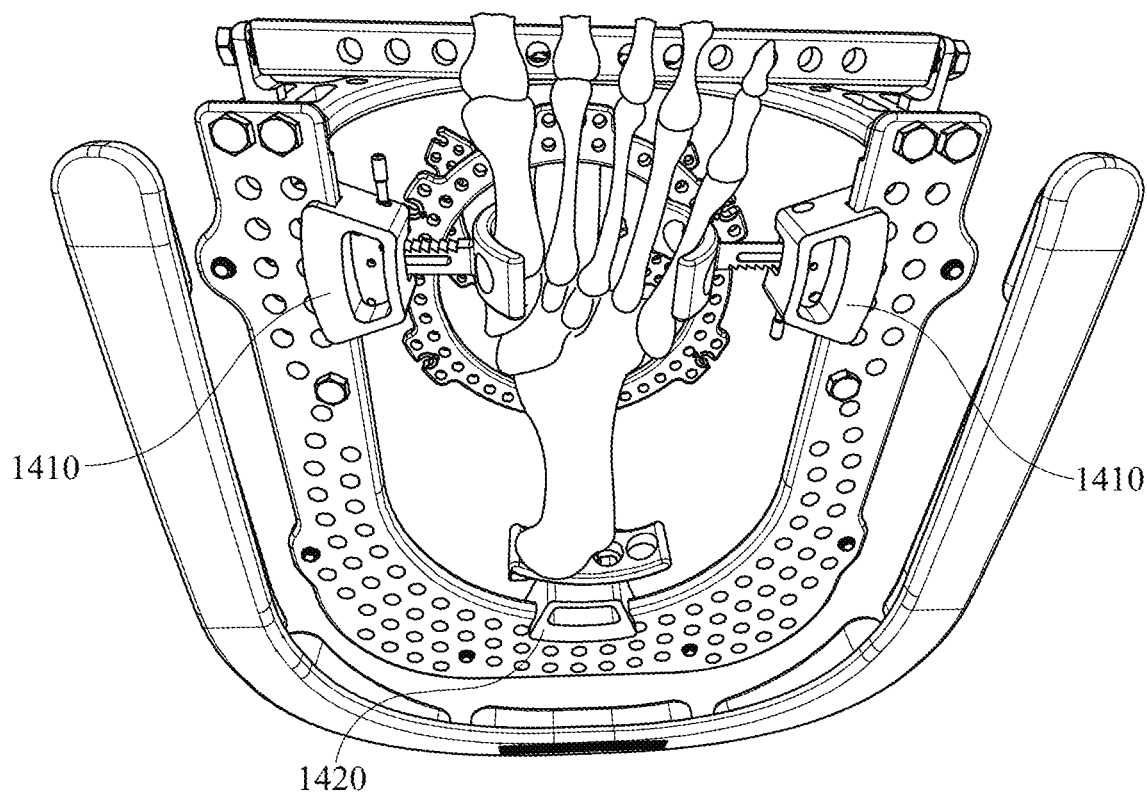
Figure 15B:
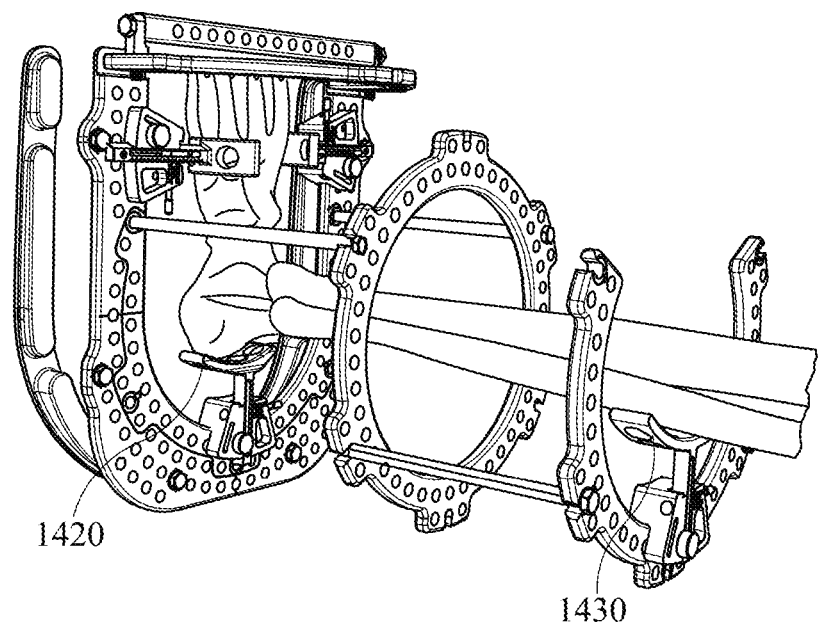

FIG. 15A is a photograph of a skeletal mock-up of the foot, with provisional alignment clamps being used. FIG. 15B is a photograph of a skeletal mock-up of the lower leg and heel, with provisional alignment clamps being used.

Figure 16A:
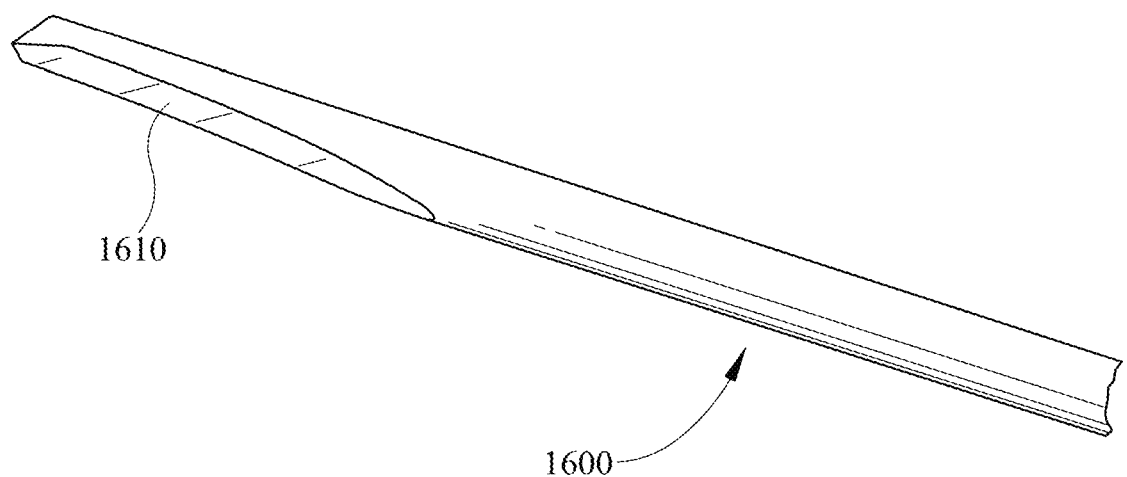
Figure 16B:
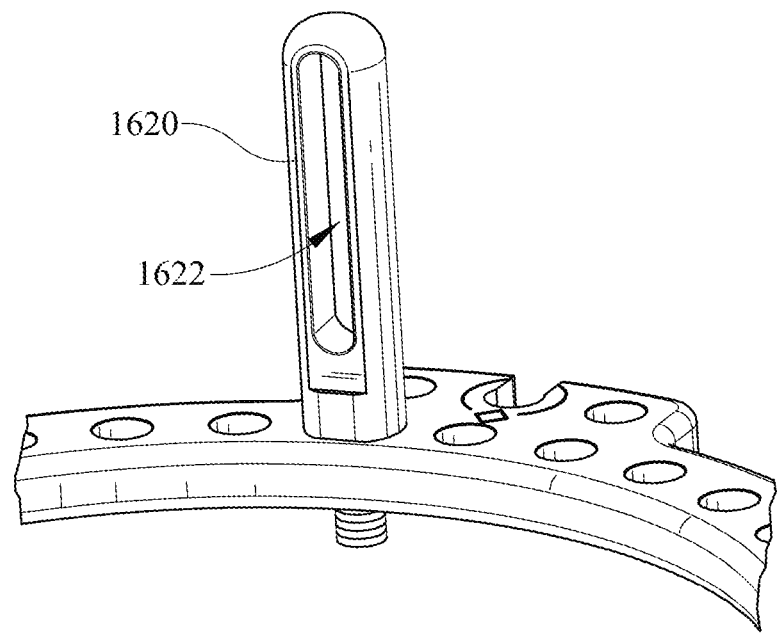
Figure 16C:
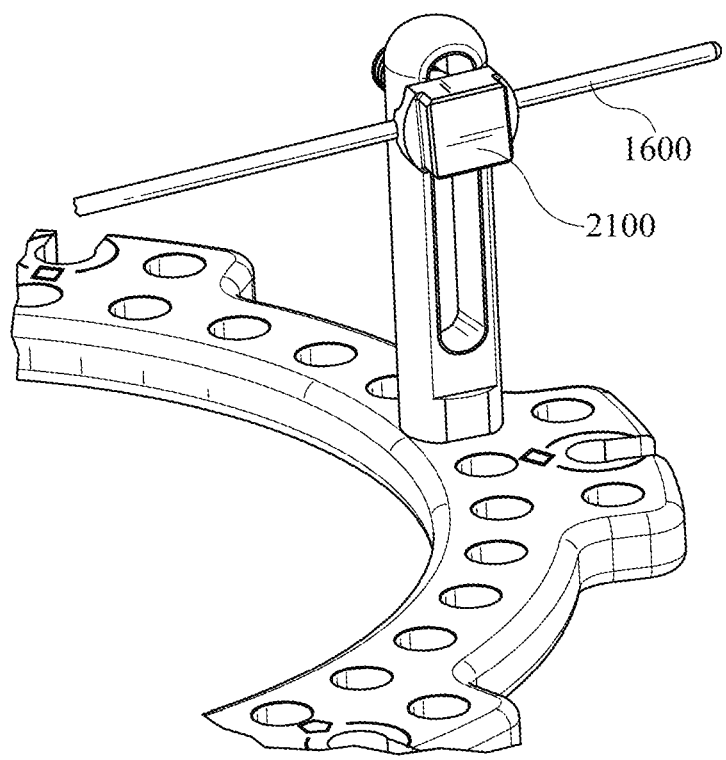

FIG. 16A is a three-dimensional view of an end of a K-wire. FIGS. 16B and 16C depict a K-wire support post attached to a plate.

Figure 17A:
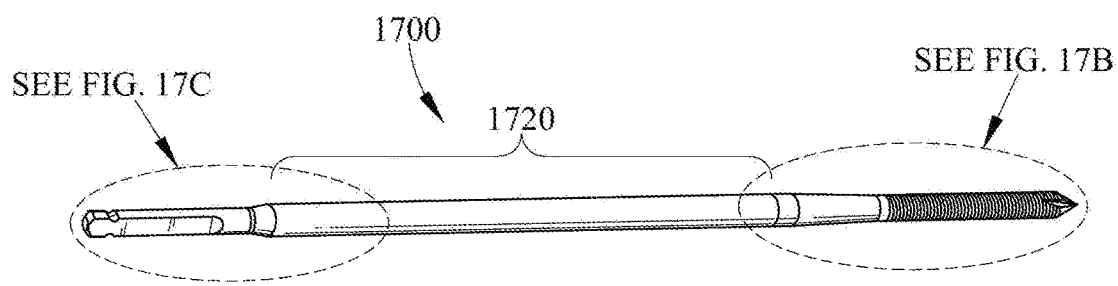
Figure 17B:
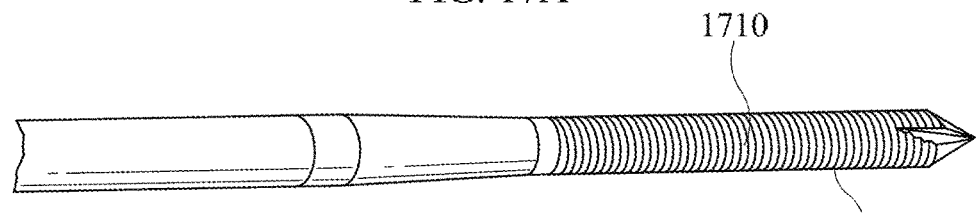
Figure 17C:
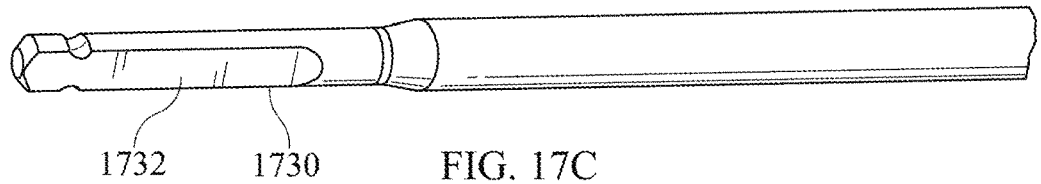

FIG. 17A depicts a half-pin. FIG. 17B is an enlarged view of the bone-engaging end of the half-pin. FIG. 17C is an enlarged view of the other end of the half-pin.

Figure 18A:
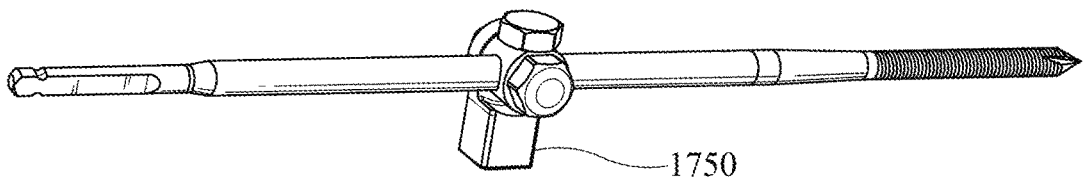
Figure 18B:
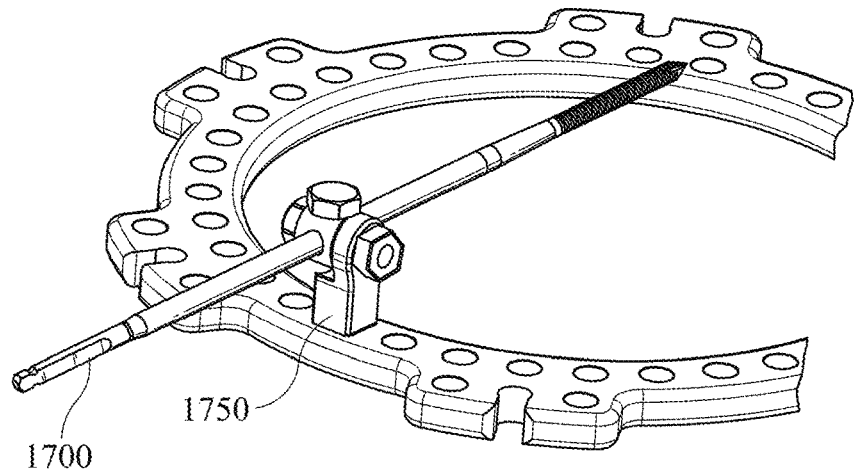

FIG. 18A depicts a half-pin being held on a half-pin support. FIG. 18B depicts the same further attached to a support ring or plate.

Figure 19A:
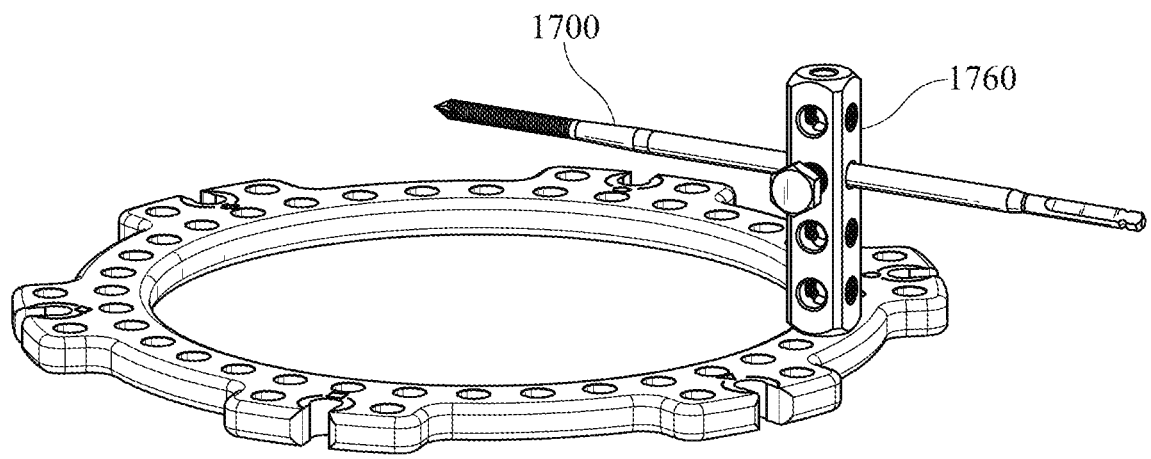
Figure 19B:
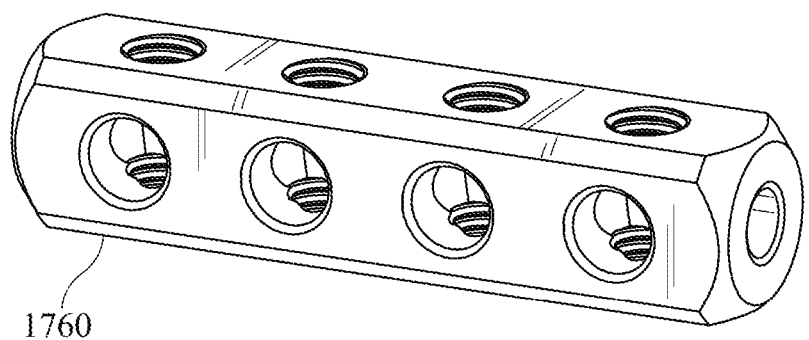
Figure 19C:
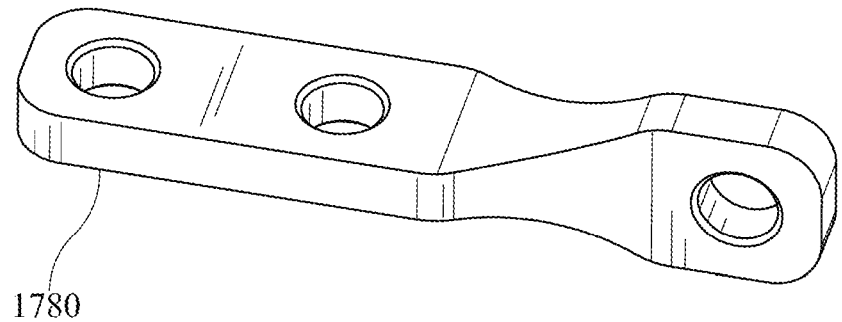

FIG. 19A depicts a half-pin attached to a ring or plate by a block. FIG. 19B is a close-up view of the block. FIG. 19C is a three-dimensional view of a connecting plate that has a 90 degree twist.

Figure 20A:
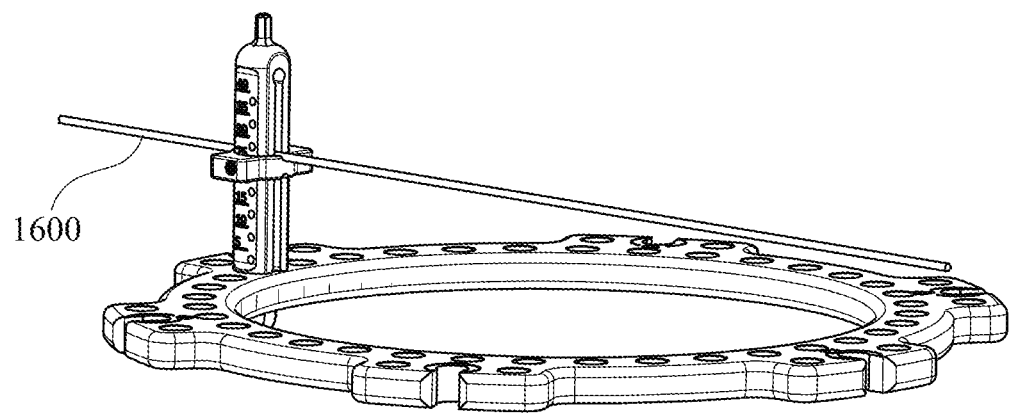
Figure 20B:
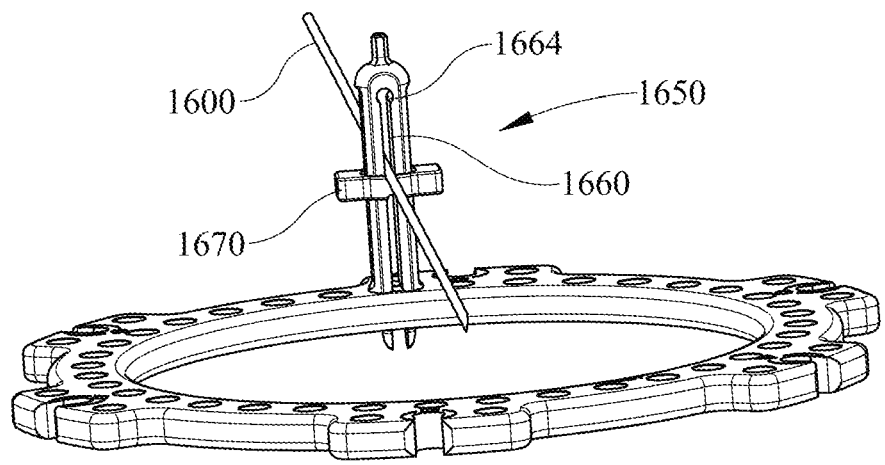
Figure 20C:
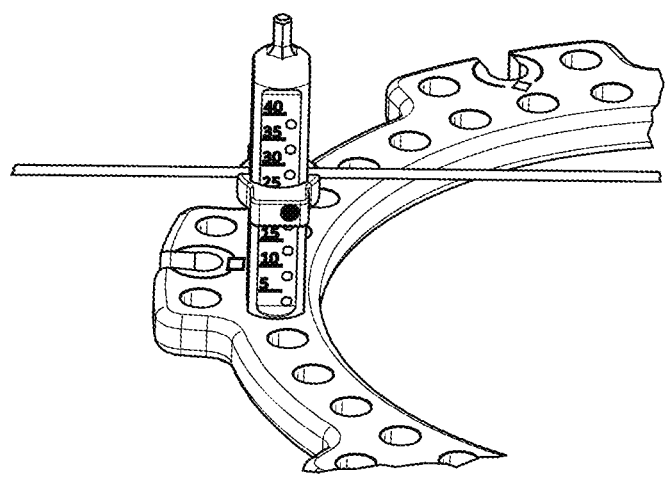

FIGS. 20A, 20B and 20C depict a K-wire being held on a K-wire alignment guide post.

Figure 21A:
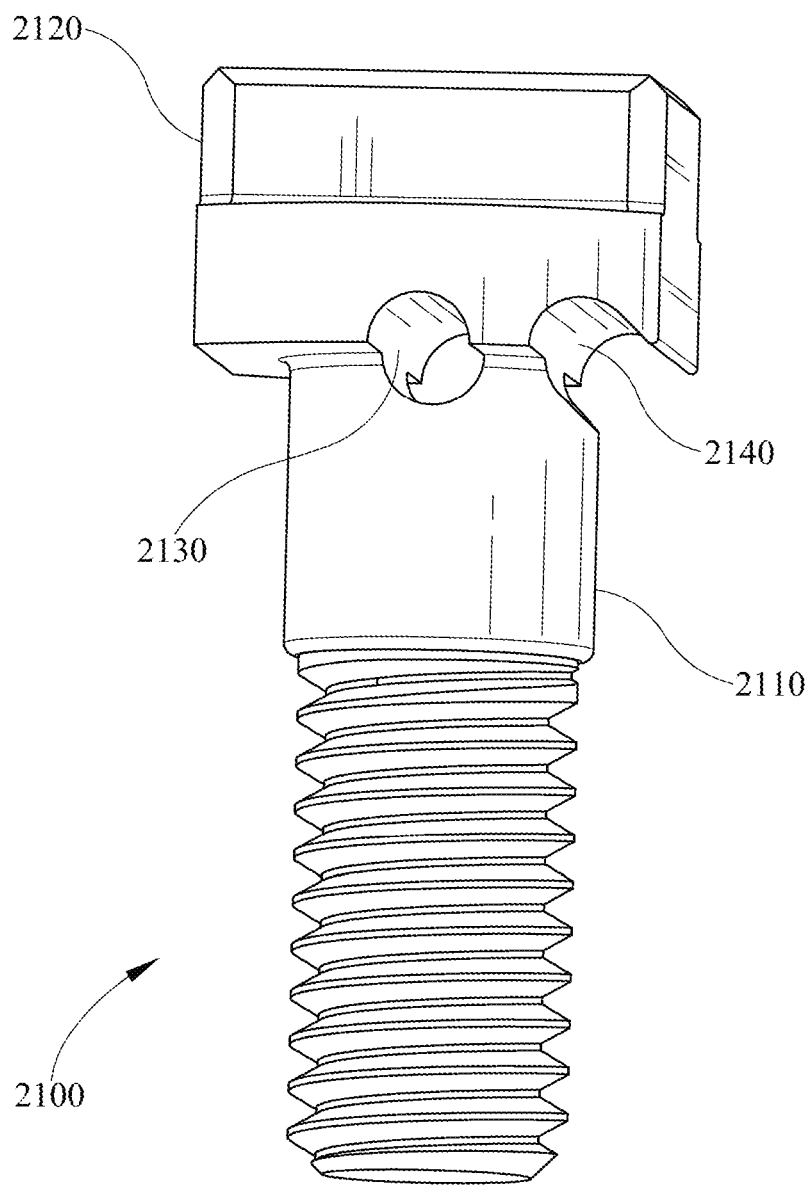
Figure 21B:
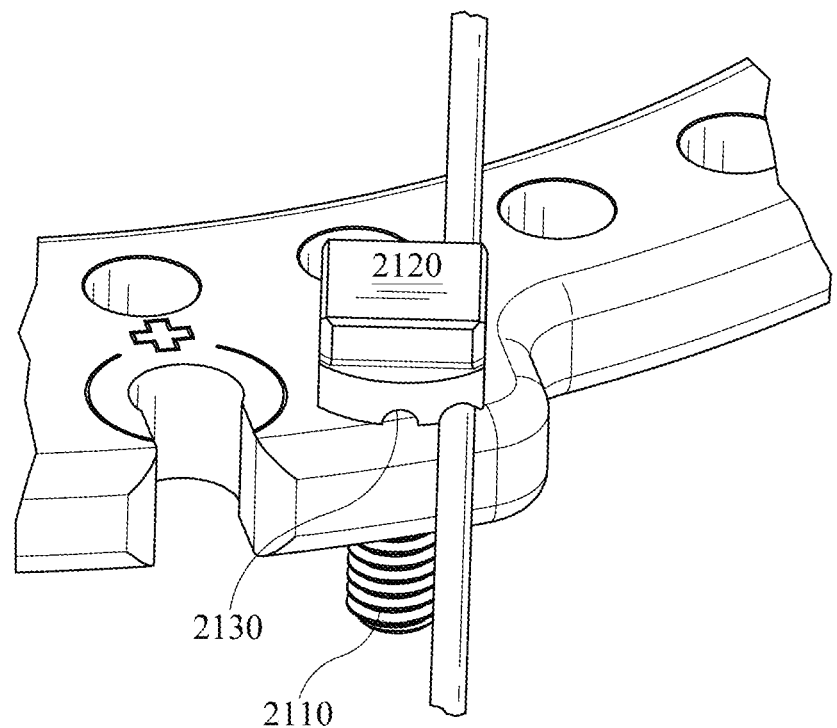
Figure 21C:
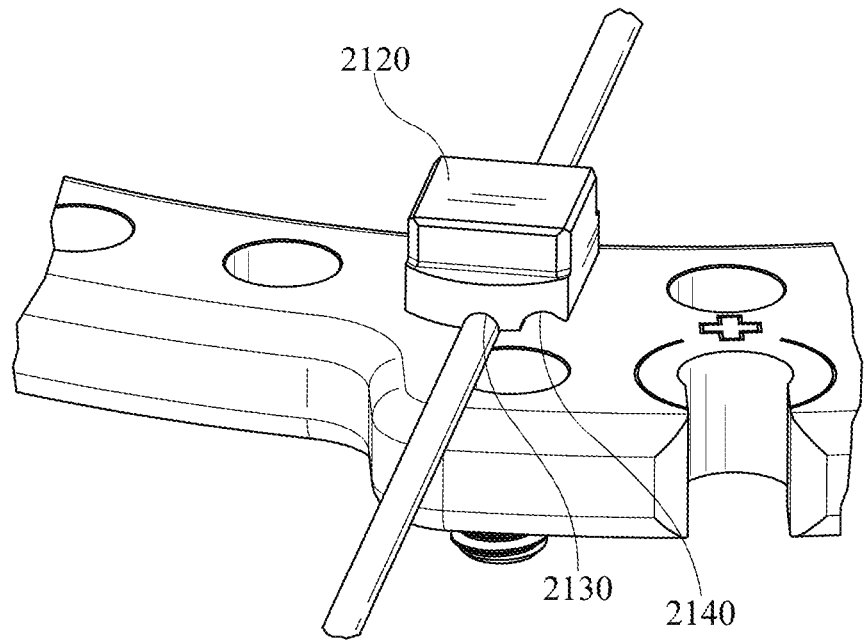

FIG. 21A depicts a universal fixation bolt, having both a through-hole and a side hole. FIG. 21B depicts a K-wire held in a side hole of a universal fixation bolt. FIG. 21C depicts a K-wire being held in a central hole of a universal fixation bolt.

Figure 22A:
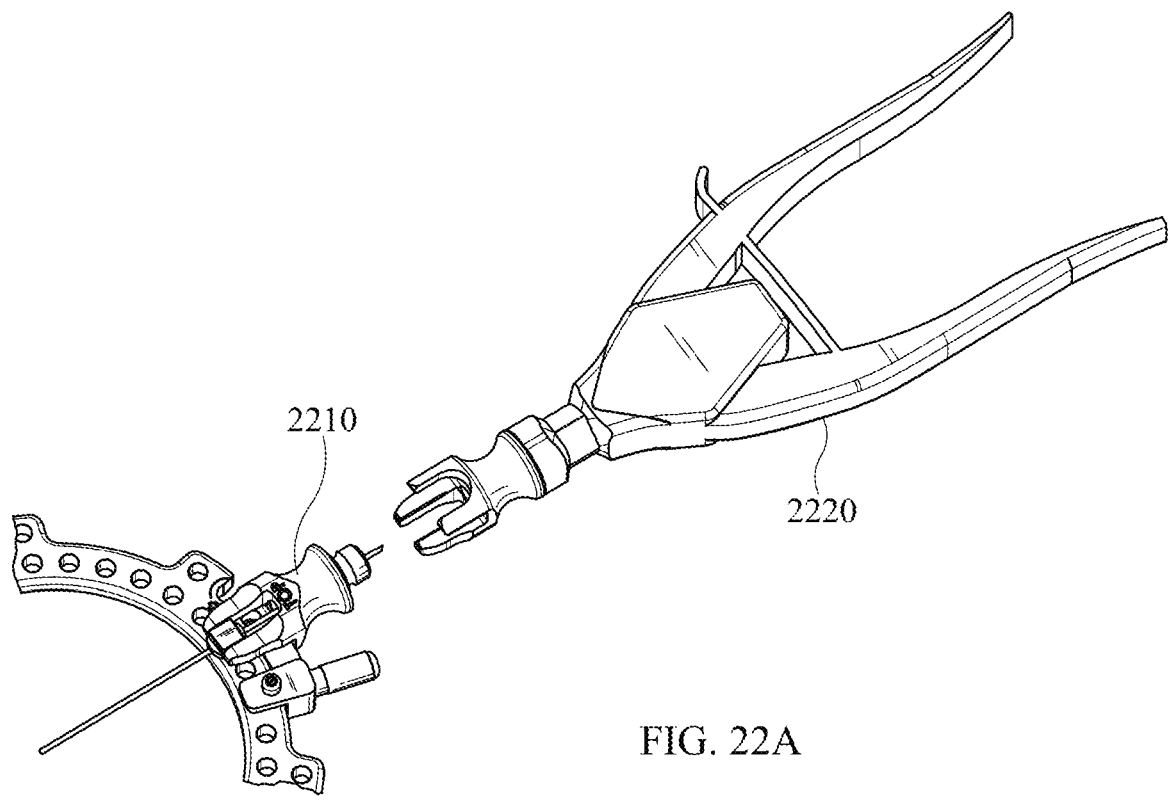
Figure 22B:
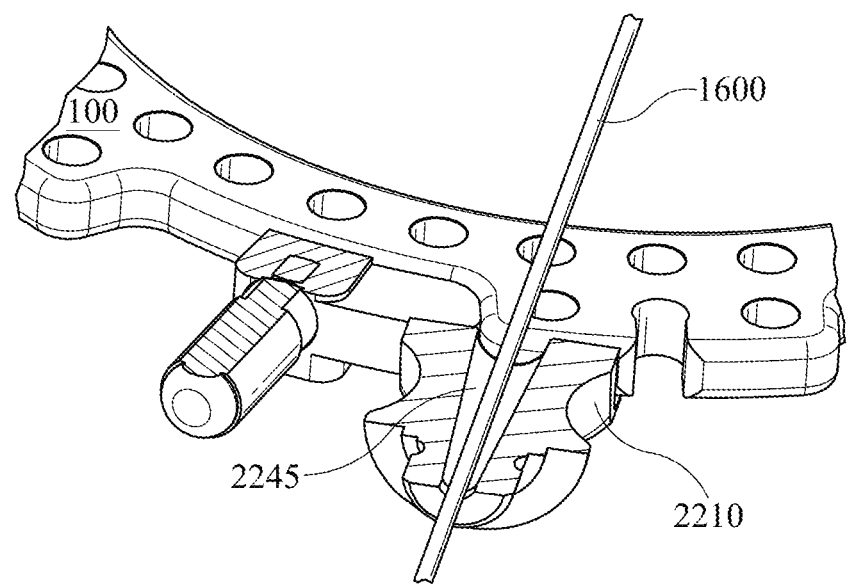
Figure 22C:
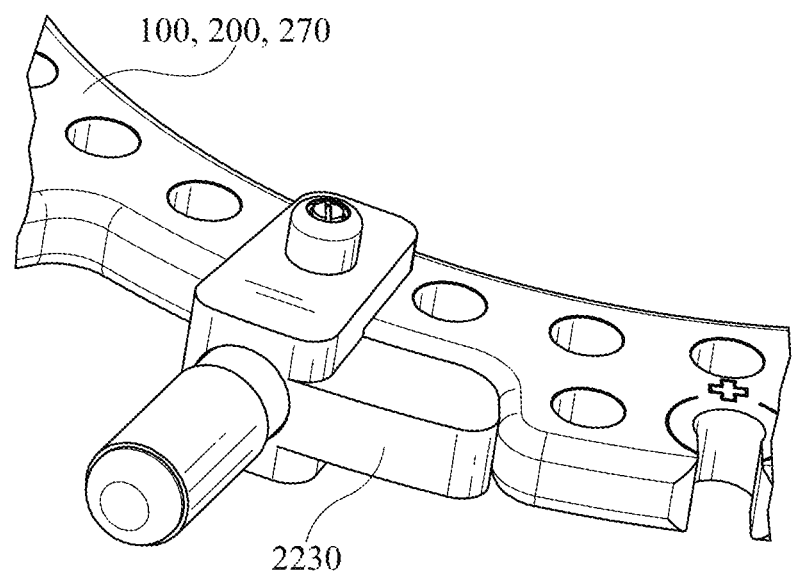
Figure 22D:
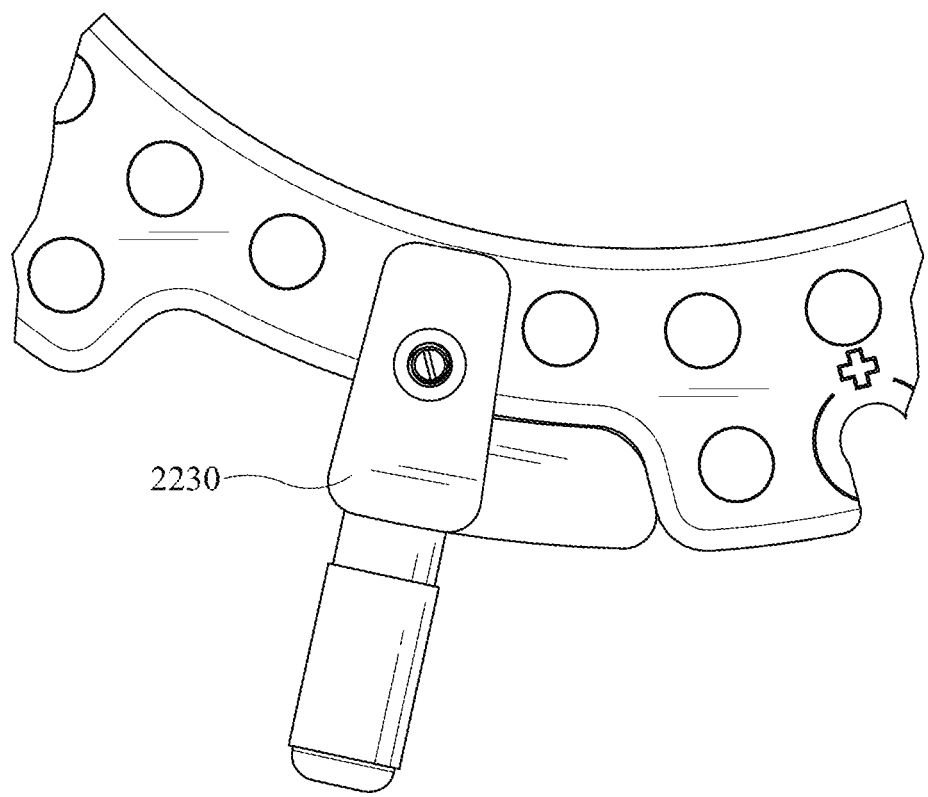
Figure 22E:
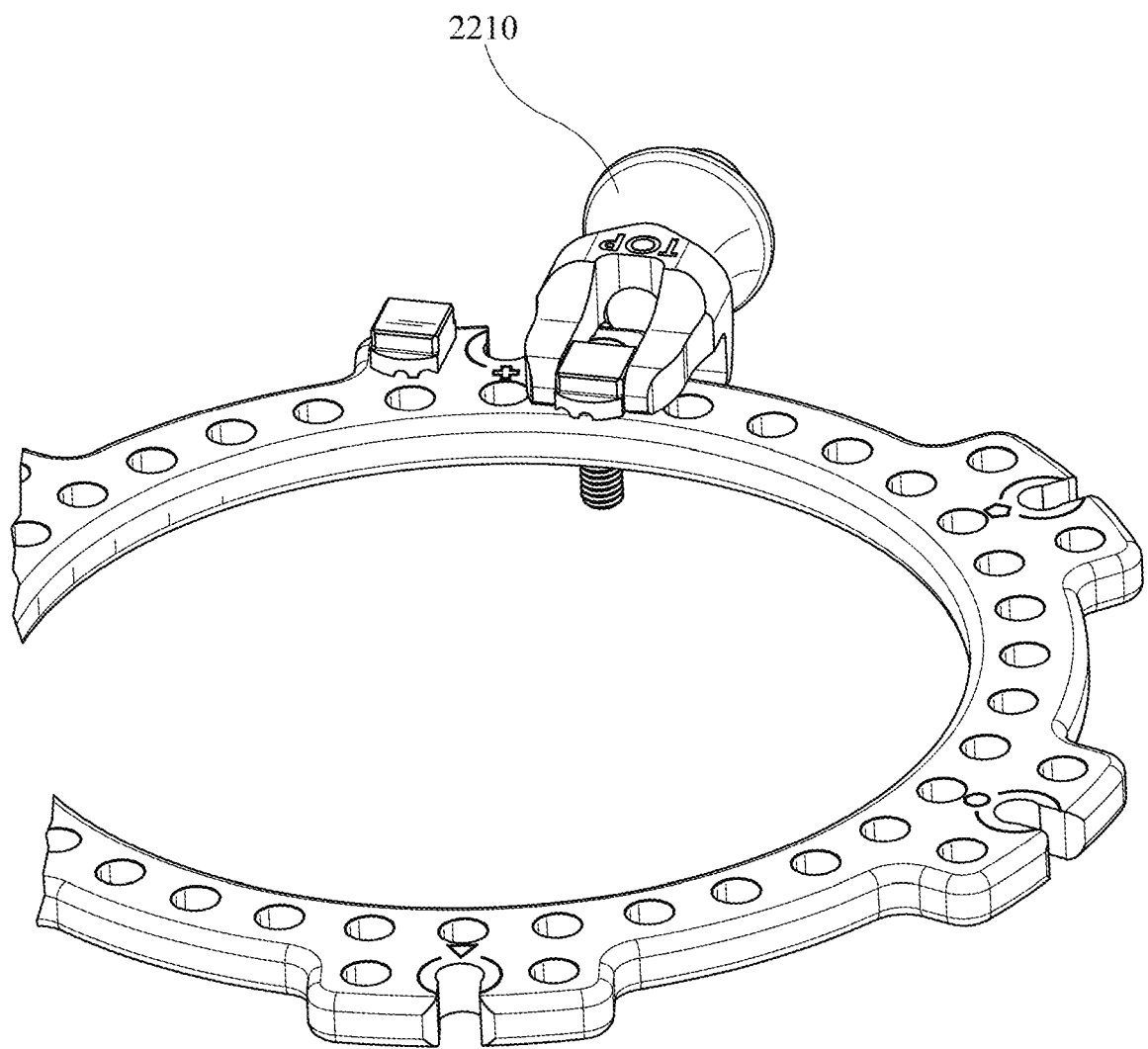
Figure 22F:
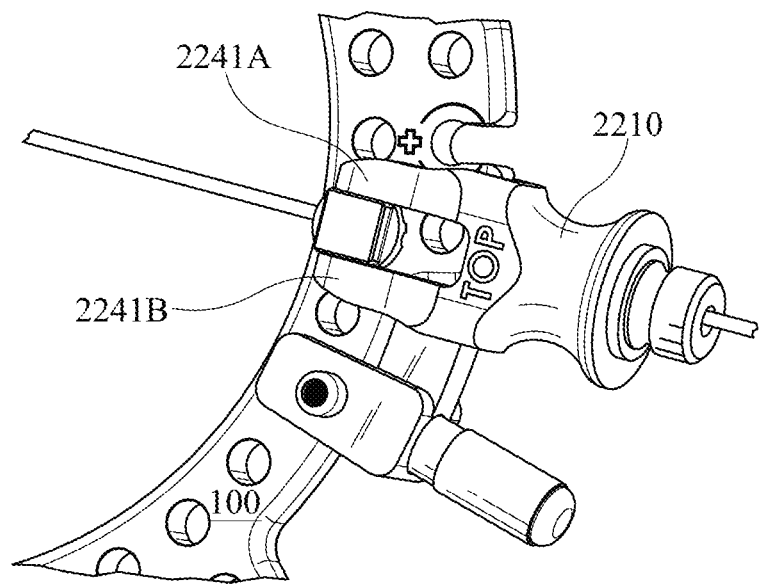
Figure 22G:
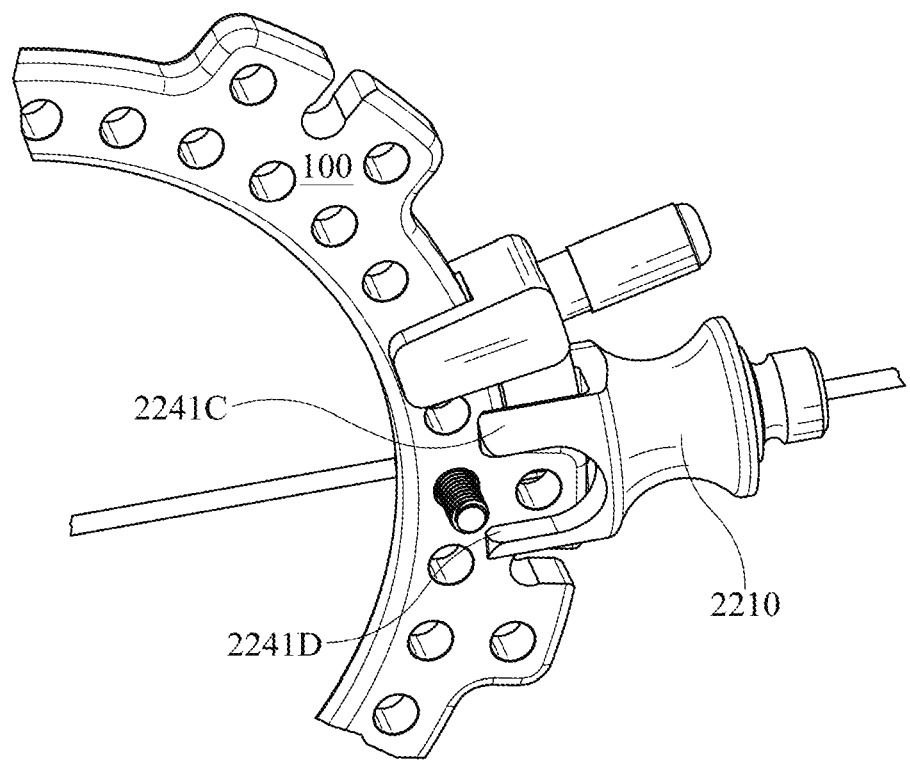
Figure 22H:
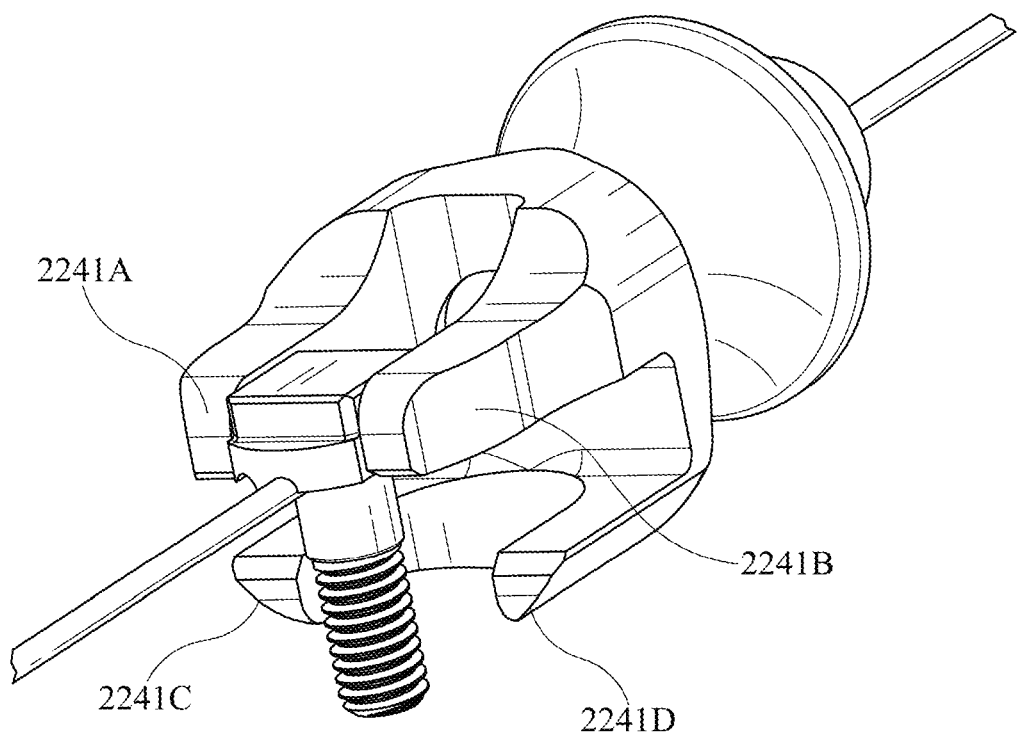
Figure 22I:
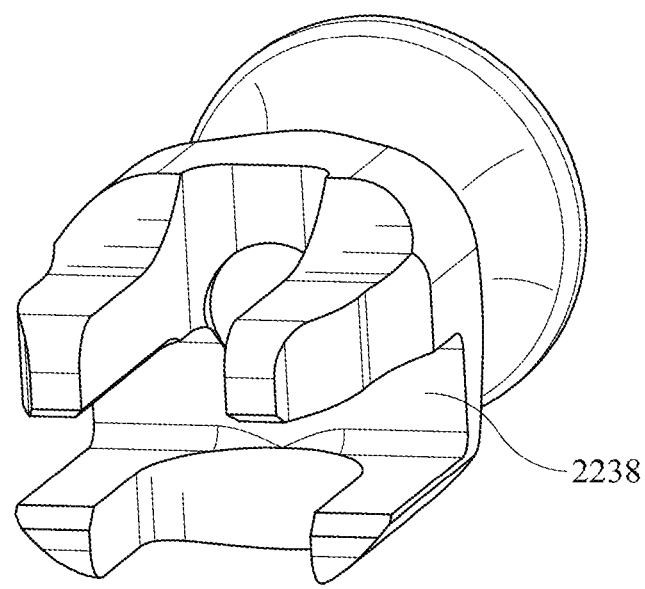

FIG. 22A shows a K-wire being tensioned using a K-wire tensioning adapter together with an alignment tool that may be used when the universal bolt is near an outrigger. FIG. 22B is a section of FIG. 22A. FIG. 22C shows just the plate or ring and the alignment spacer, in a three-dimensional perspective view. FIG. 22D is similar to FIG. 22C but in plan view. FIG. 22E shows the plate, the tensioning adapter and a universal fixation bolt, in a three-dimensional perspective view. FIG. 22F shows those same components somewhat from a top view, and FIG. 22G shows those same components somewhat from a bottom view. FIG. 22H shows the tensioning adapter and a universal fixation bolt, in a three-dimensional perspective view. FIG. 22I shows the tensioning adapter in isolation, in a three-dimensional perspective view.

Figure 23A:
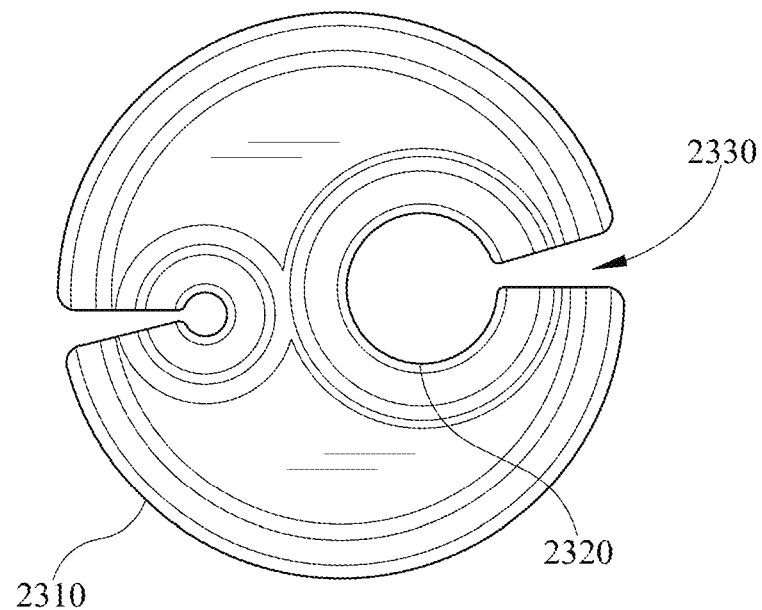
Figure 23B:
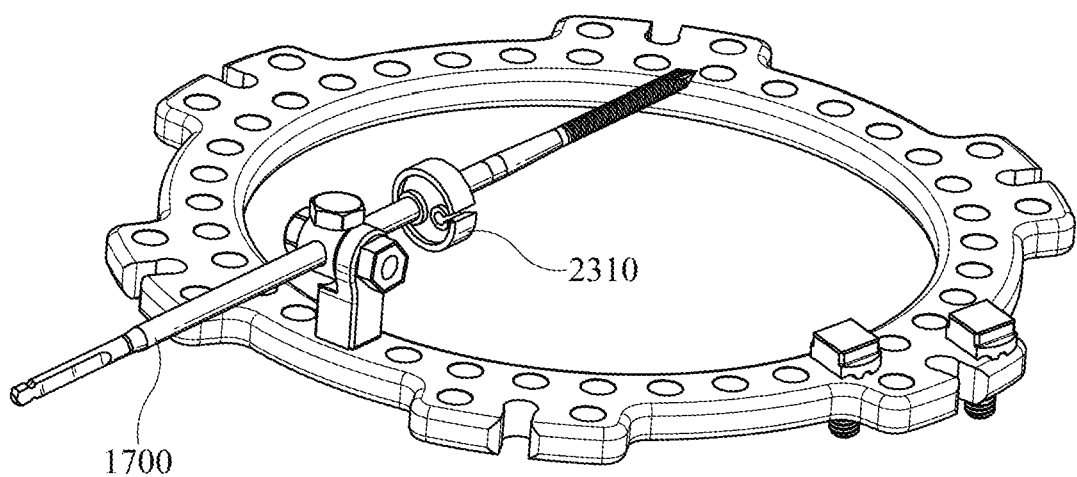
Figure 23C:
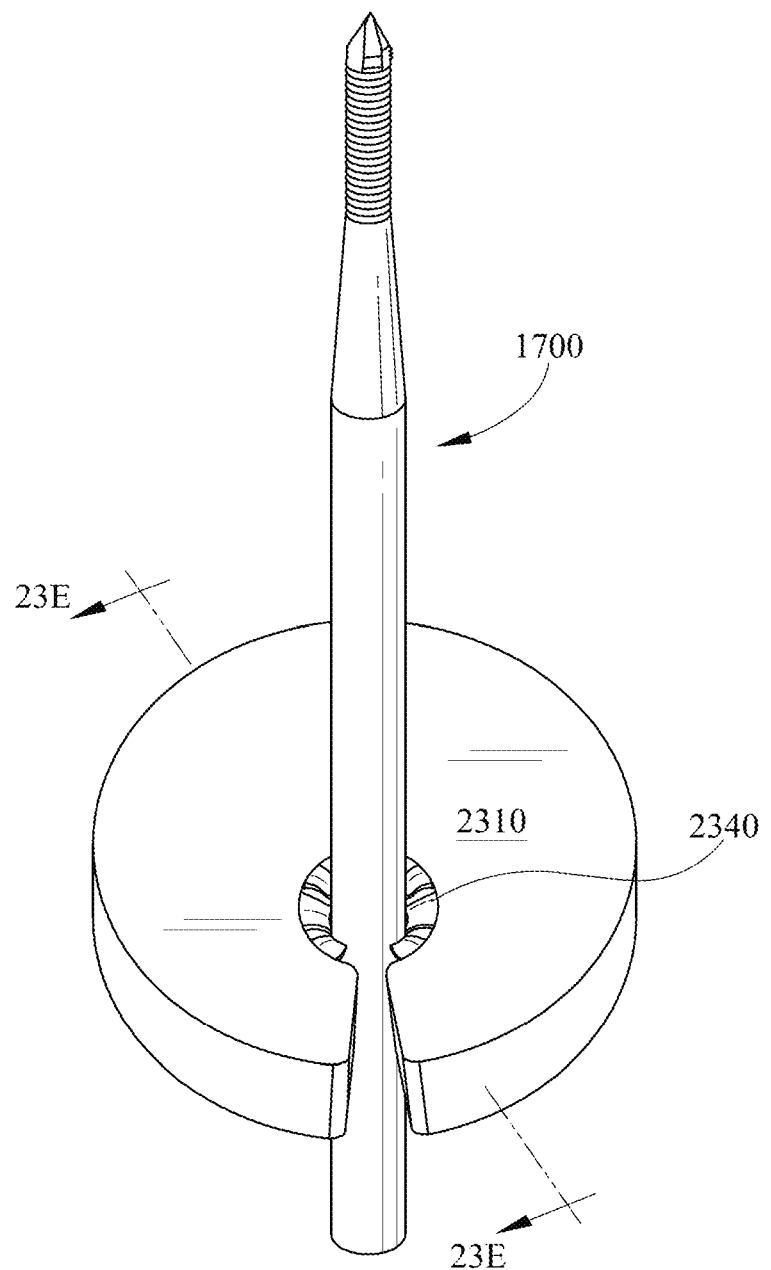
Figure 23D:
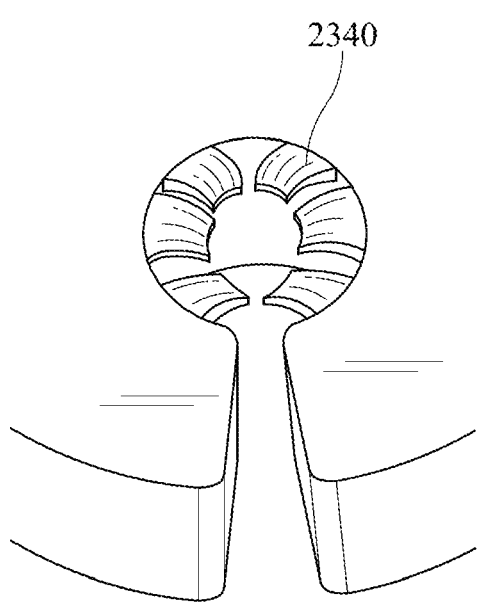
Figure 23E:
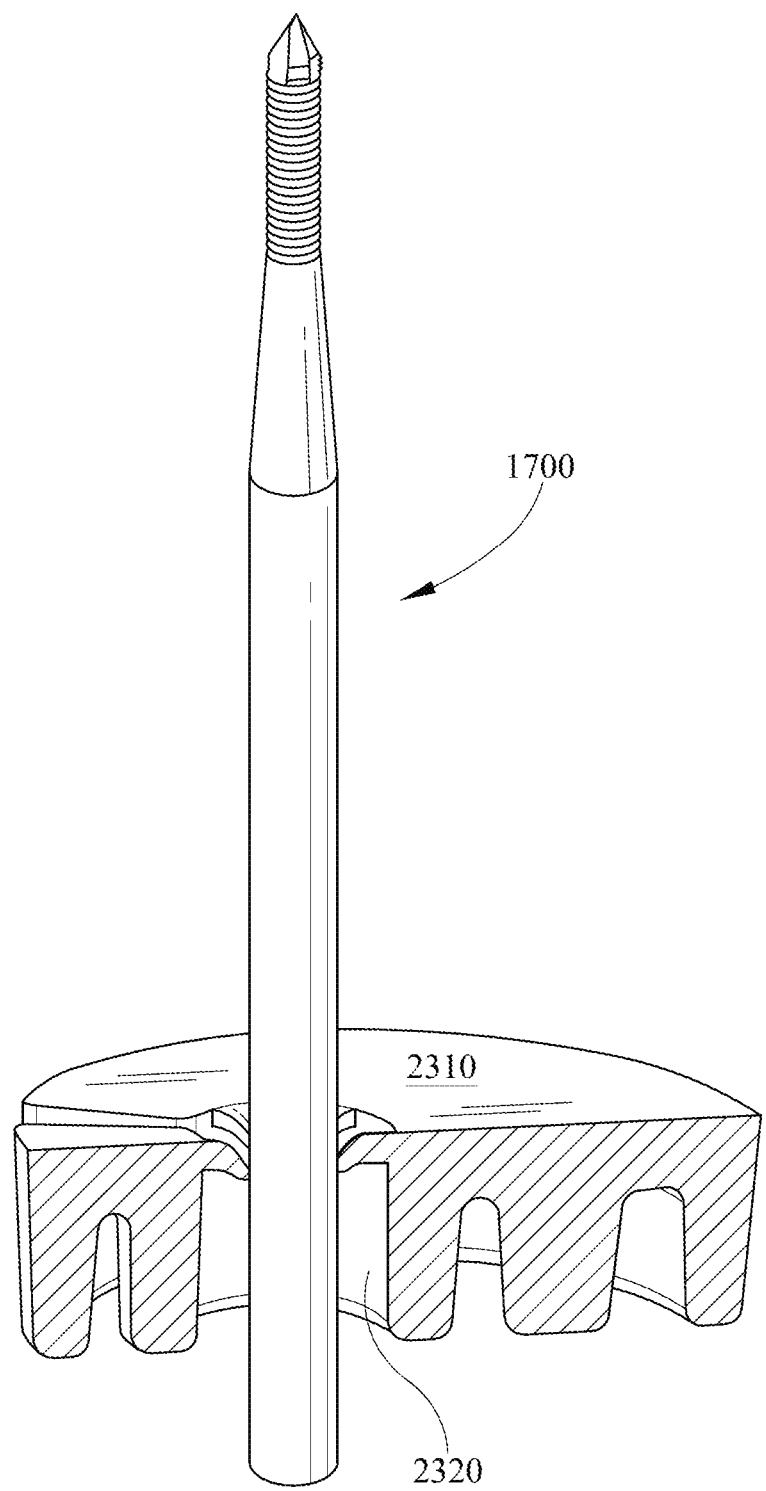

FIG. 23A depicts a retention device, which may be resilient, in isolation. FIG. 23B depicts a retention device mounted on a half-pin that is in turn mounted on a plate or ring. FIG. 23C depicts a retention ring that contains flaps. FIG. 23D is a close-up view of a portion of FIG. 23C. FIG. 23E is a cross-section of FIG. 23C.

DETAILED DESCRIPTION OF THE INVENTION

External fixation may be utilized to stabilize bone fractures so that they can heal. External fixation can also be utilized to either compress or distract the bones to a desired alignment and length, and can also be used for correction of deformity. An External Fixation System may contain various components including plates or rings, connectors, threaded rods, wires, pins, posts, blocks, and other components to align, stabilize, and connect to the bones. The wires or pins or both may pass through the patient's skin in order to connect a bone or bone fragment to the external fixation apparatus. The plates or rings may fully or partially encircle the patient's limb, and there may be wires or pins or both that may be connected to the rings. The plates or rings may be structurally connected to each other in such a way that the separation distance and other aspects of the spatial relationship between the rings can be adjusted. The adjustability may permit overall adjustment during surgery or at other times, and may permit adjustment in a very gradual manner as the bone heals.

Figure 1:
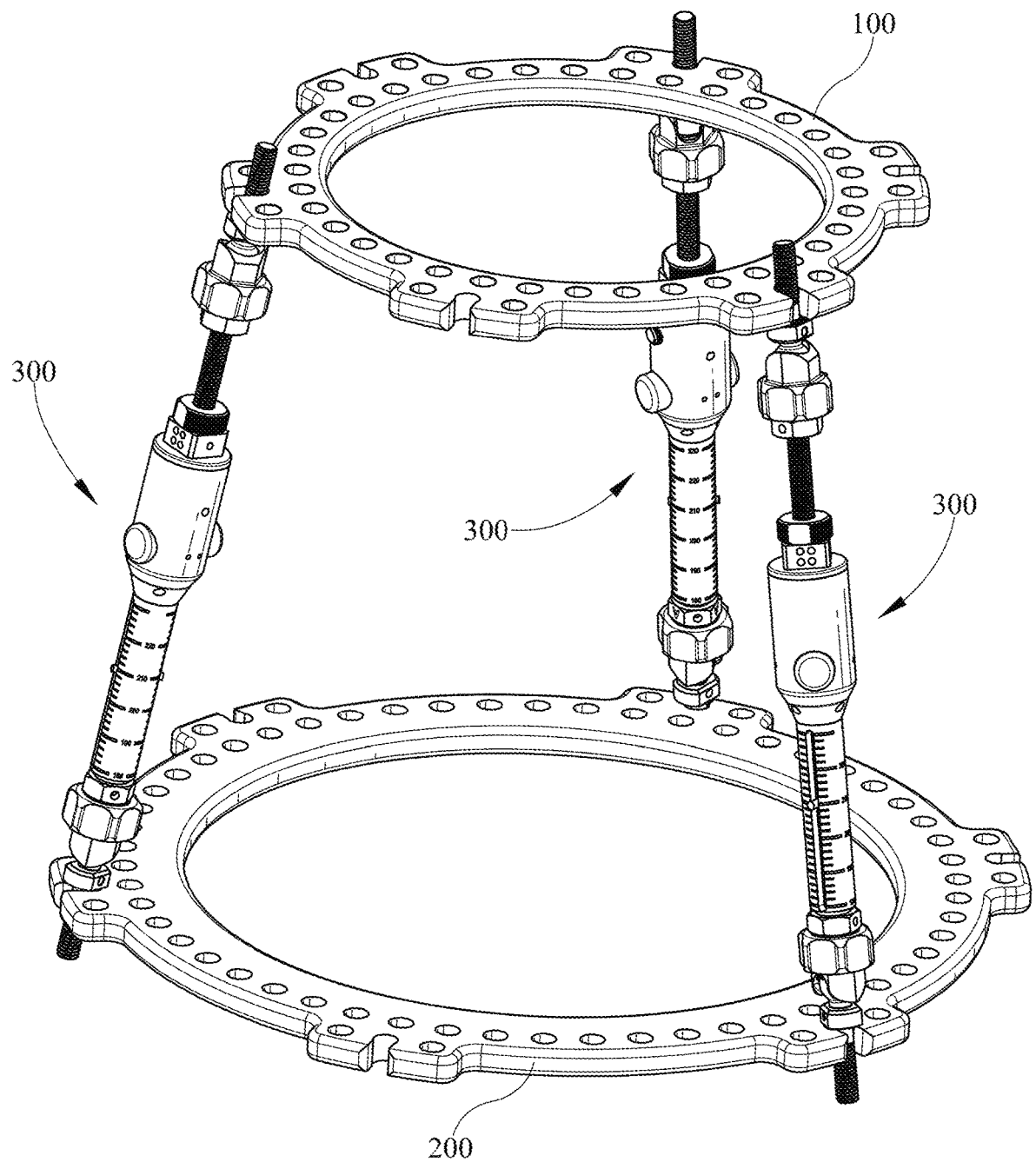
Figure 2A:
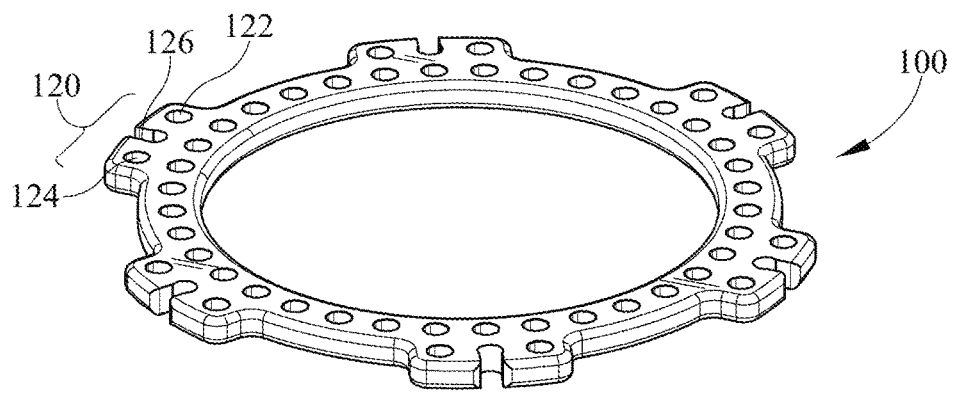
Figure 2B:
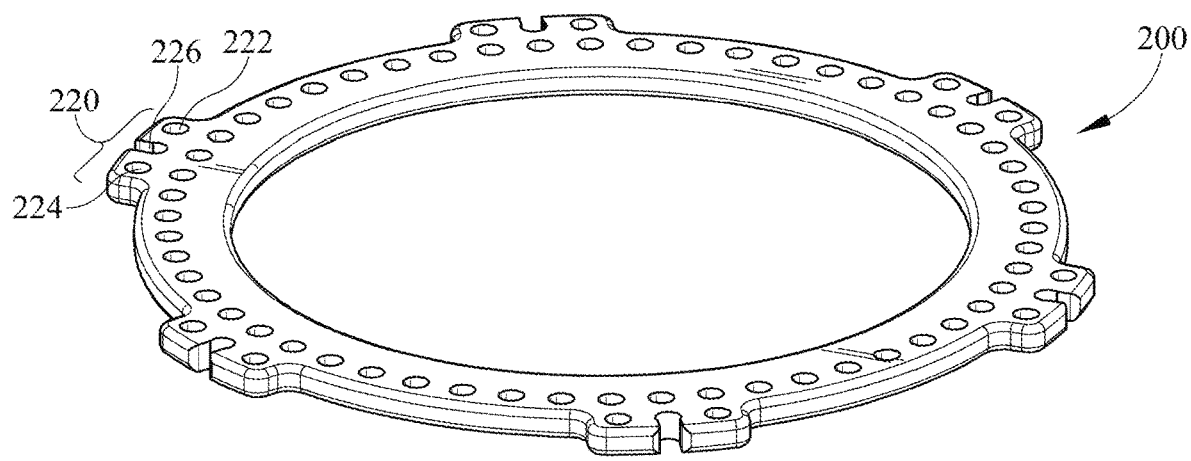
Figure 2C:
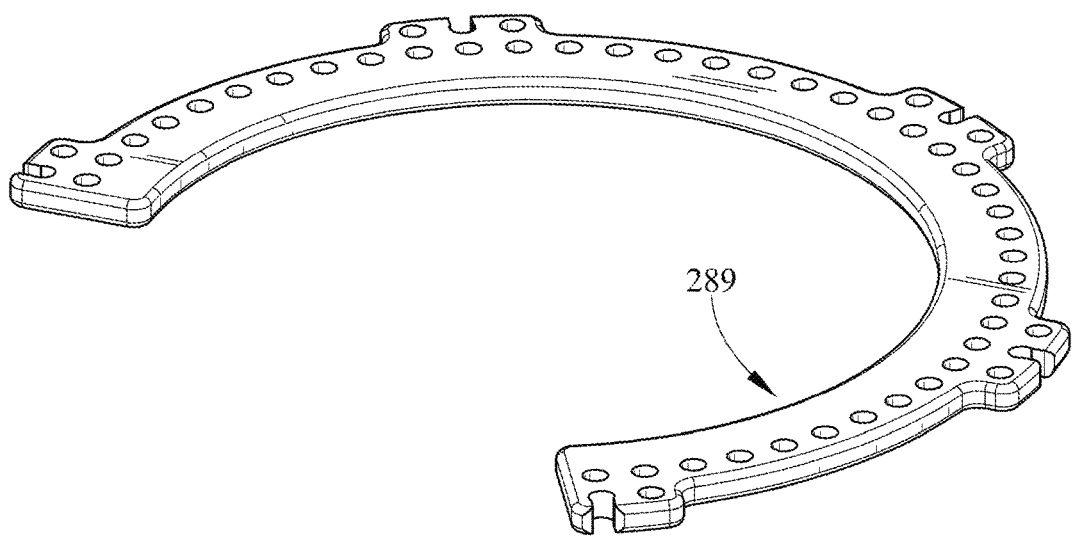
Figure 2D:
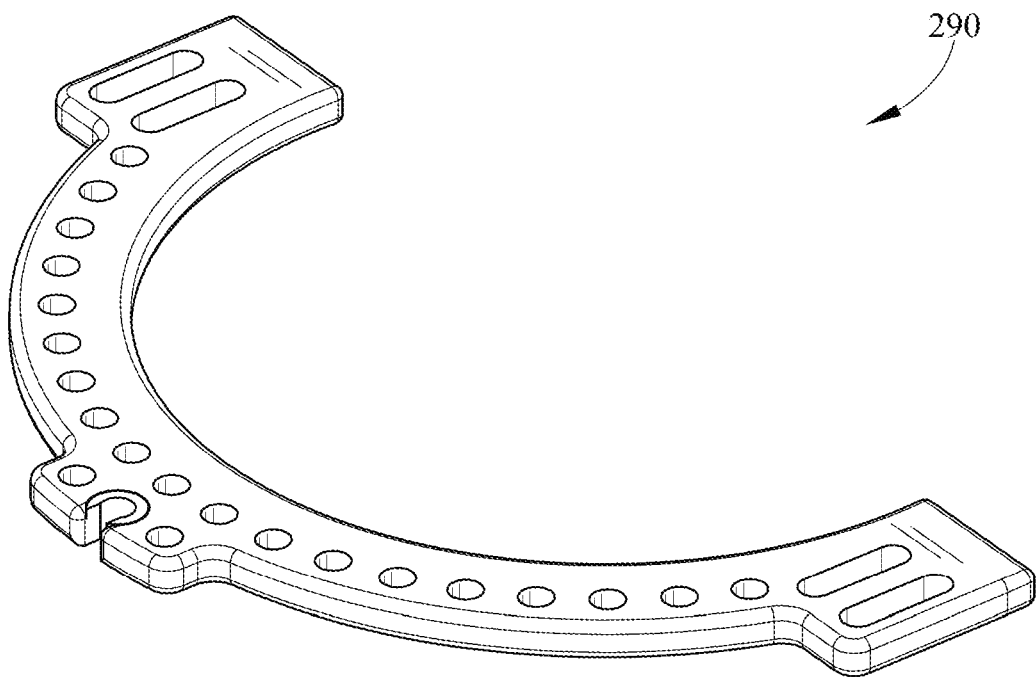
Figure 2E:
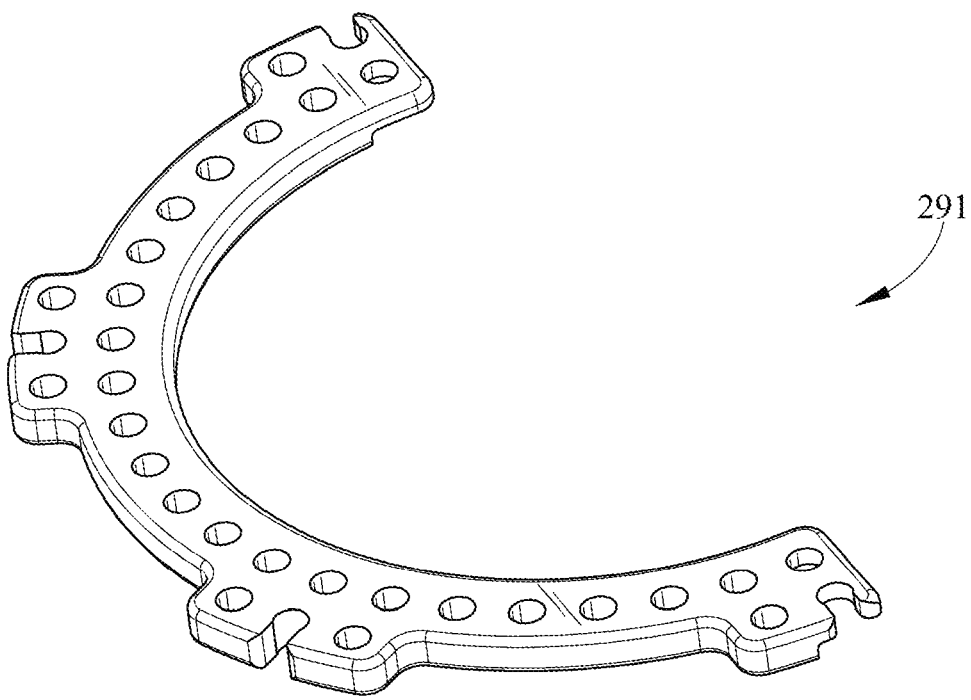
Figure 2F:
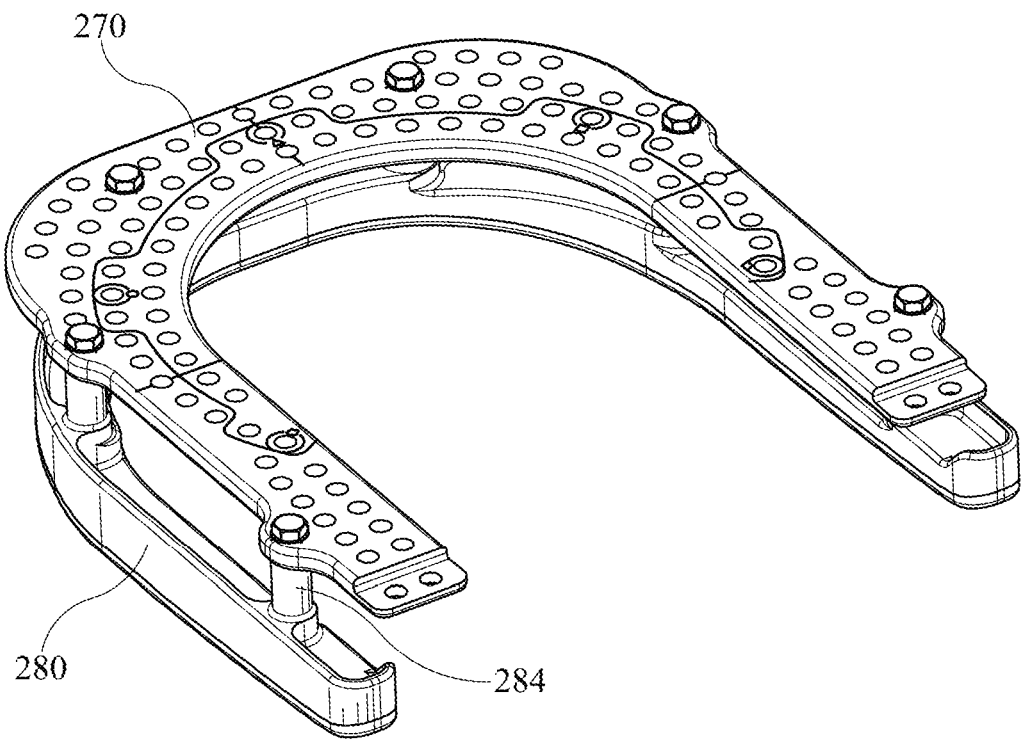

Referring now to FIGS. 1 and 2A-2E, in an embodiment of the invention, an external fixation system may comprise, first of all, a proximal plate 100 and a distal plate 200. The proximal plate 100 may be the plate that is closer to the patient's torso and the distal plate 200 may be the plate that is further from the patient's torso. Either of these plates 100, 200 or both may form a closed path forming a complete circumference defining an interior space that is at least partially empty. The dimensions of the interior space may be suitable for the patient's limb to pass through the interior space. Such a plate can be referred to as a ring. It is also possible that any of these plates 100, 200 may be an incomplete circumference, such as a U-shape, defining an interior space that connects with an exterior space. An example of such a plate may be a half-ring that comprises approximately a semicircle optionally with straight ends extending from the semicircle, which may be referred to as a footplate 270 (FIG. 2F). Another example may be slightly more than a semicircle (sometimes referred to as ⅝ circumference, as shown in FIG. 2C). Another example of such a plate is a simple semicircular plate. One version of a semicircular plate 290 is shown in FIG. 2D, and another version of a semicircular plate 291 is shown in FIG. 2E. The word plate is intended to refer generically to either a full-circumference or a partial-circumference geometry. Plates 100, 200 (as well as plates 270, 289, 290, 291) may be substantially flat and of substantially uniform thickness as illustrated, but it is also possible that they may have other contours and dimensional characteristics. It is possible that, as illustrated, the distal plate 200 may be larger in some overall dimension than the proximal plate 100. However, this is not essential. It is further possible that a structure could be constructed having a series of three plates, with the third plate being placed beyond the illustrated structure of two plates 100, 200, with all three of the plates being connected to form a structure.

Either or both of plates 100, 200 (and similarly plates 270, 289, 290, 291) may comprise a plurality of holes. Such holes may permit the attachment thereto of various attachment hardware. Such holes may be through-holes or blind holes, threaded or unthreaded, or any combination thereof. Within a plate, such holes may be distributed in a pattern that repeats regularly, or they may be arranged in any other desired configuration. A plate both may comprise a regularly-repeating pattern of holes and may additionally comprise other holes at desired locations.

It is further possible that one or more of plates 100, 200 (and similarly plates 270, 289, 290, 291) may comprise one or more outriggers 120, 220, with an outrigger being a region that extends in a radial direction beyond a remaining portion of the same plate 100, 200. The outrigger 120, 220 may comprise one or more outrigger holes 122, 124 or 222, 224, or one or more outrigger slots 126, 226, or both. An outrigger slot 126, 226 may break through the external perimeter of the plate 100, 200, 270, 289, 290, 291, or alternatively (not illustrated) may break through the internal perimeter of the plate 100, 200. It is further possible both to have both internal and external slots 126, 226 at various places in a plate 100, 200, 270, 289, 290, 291. As illustrated in FIGS. 2A-2E, an outrigger 120, 220 may contain two outrigger holes 122, 124 or 222, 224 and one outrigger slot 126 or 226. The outrigger slot 126, 226 may be located between the outrigger holes 122, 124 or 222, 224. In addition to being provided in outriggers 120, 220, slots could be provided in non-outrigger regions of a plate 100, 200, 270, 289, 290, 291 (although this is not illustrated).

Figure 2G:
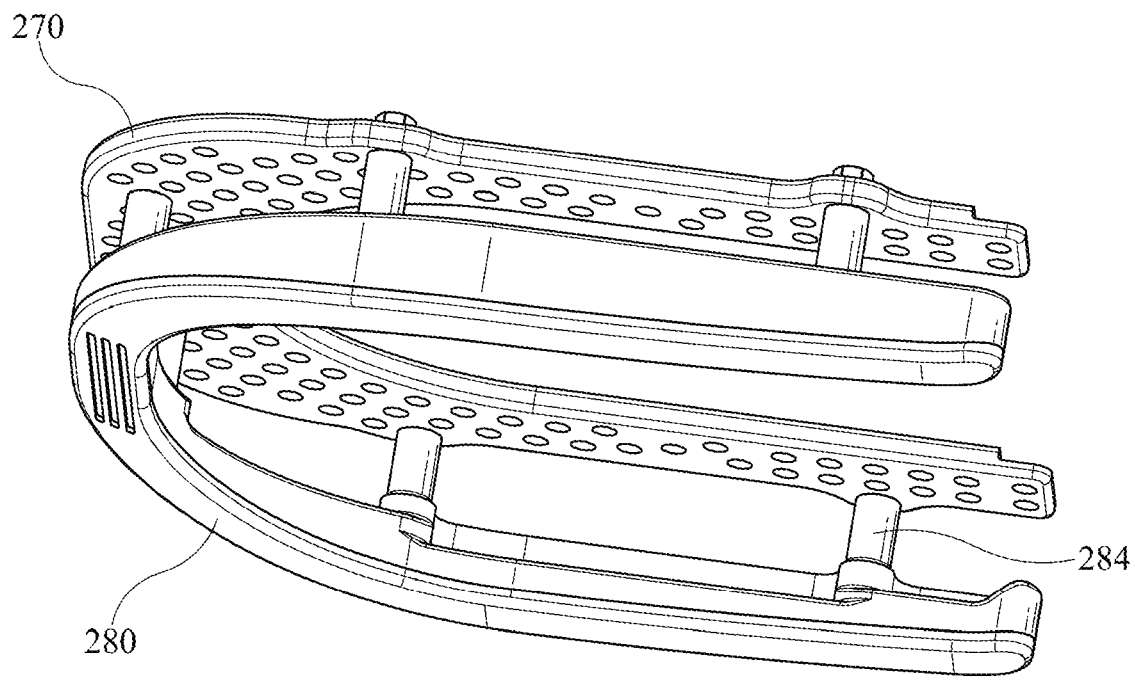

Referring now to FIGS. 2F and 2G, in an embodiment of the invention, a footplate 270 and a rocker bottom 280 may be utilized. The footplate 270 may be in a location corresponding to the more distal plate 200, and may be similar to plate 200 described elsewhere herein. The footplate 270 may be a distal plate 200 that does not form a complete closed curve; rather, for example, it may form a U-shape. The footplate 270 may be provided in various different sizes to fit the patient, and may be attached or attachable to the rocker bottom 280 by means of fasteners that may go through holes in the footplate 270. The rocker bottom 280 may have a shape that, in plan view, is similar to the shape of the footplate, such as a U-shape. The fixation system of an embodiment of the invention can be used either with or without a rocker bottom.

Facing away from the footplate 270, the rocker bottom 280 may have an underside surface that may be curved. This may be the surface that touches the floor when the patient is walking. The shape of the curved surface may be chosen so as to provide desired characteristics for walking by the patient. The footplate 270 and the rocker bottom 280 may be separated by spacers 284. The spacer dimensions or the separation distance between the footplate and the rocker bottom 280 may be chosen so as to provide a desired elevation of the patient's foot, relative to other parts of the patient's body.

In this embodiment, the footplate 270 may have a plurality of holes arranged in a regular or repeating pattern. Such holes may, for example be used for attachment thereto of connectors, posts or other hardware. In addition, there may be regions outside the regularly-repeating footplate hole pattern, that may be small regions with at least one hole that is appropriate for attachment to the rocker bottom 280. Some or all of these holes that are used to attach the rocker bottom 280 may be separate from any plate hole pattern, such as a regularly-repeating hole pattern, such as might be used for bone fixation hardware. Some of these holes may be used only to attach to the rocker bottom 280. The spacers going to the rocker bottom 280 may attach to attachment points that may be in regions of the footplate 270 that are outside of or different from the regularly-repeating hole pattern. The use of extra holes on the footplate 270 for the rocker bottom 280 attachment may allow the regularly-repeating pattern of footplate holes to be utilized with full freedom for attachment of components such as connectors 300 and posts as shown in FIG. 1.

Figure 2H:
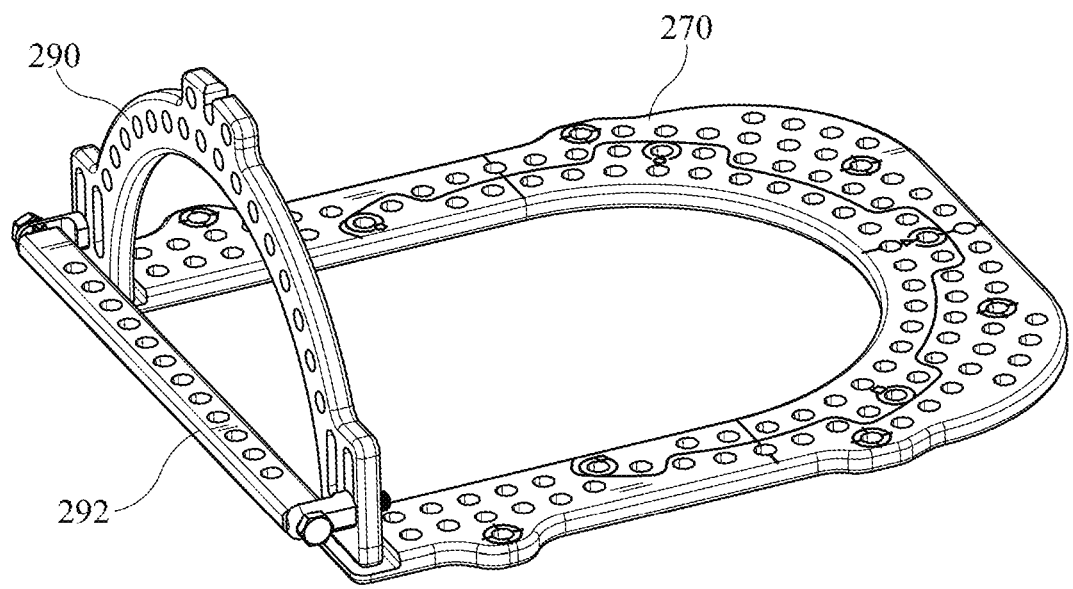
Figure 2I:
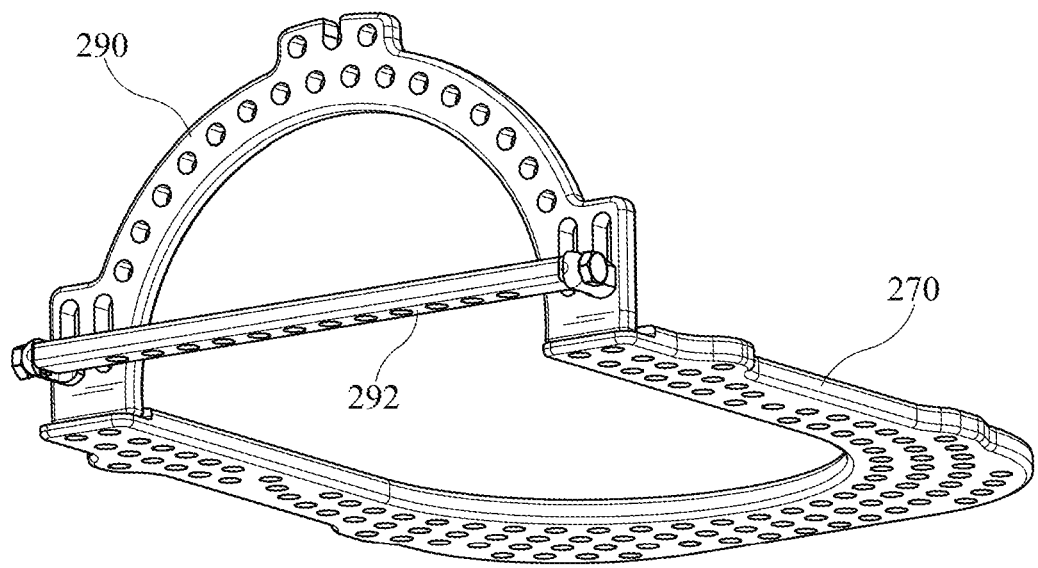

It is further possible that a version of the semicircular plate, such as the semicircular plate 290 of FIG. 2D, could be connected to the anterior end of the footplate 270. This is illustrated in FIGS. 2H and 2I. Such an arrangement could allow for fixation elements to be connected to the anterior portion of the patient's foot as needed. As illustrated in FIGS. 2H and 2I, there may further be provided a crossbar 292 that connects to the semicircular plate 290. The crossbar 292 may have still further connection points such as holes, which may be used for connection of various hardware as is described elsewhere herein. It is noted that this is not the only way in which a semicircular plate 290, 291 may be used in embodiments of the invention. For example, a fractional plate could be used generally in any circumstance in which a full-circle plate is used, if appropriate for the patient's condition.

Figure 3A:
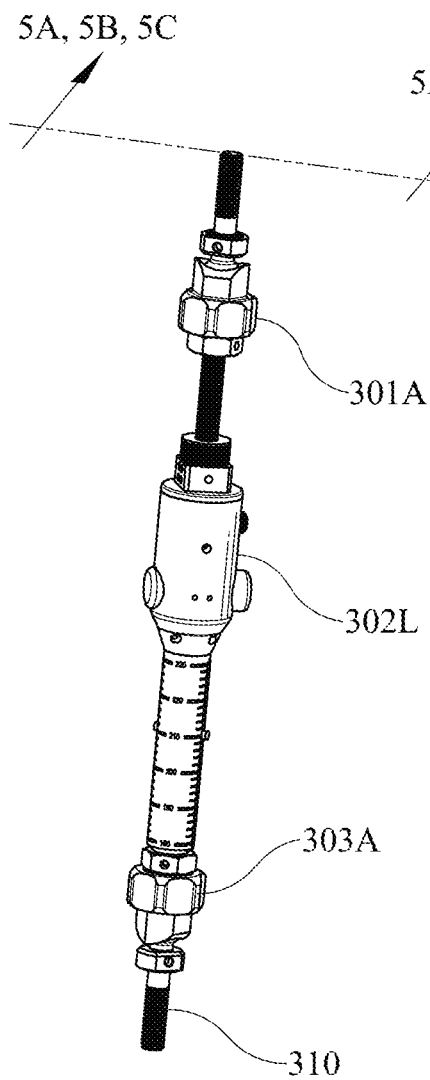
Figure 3B:
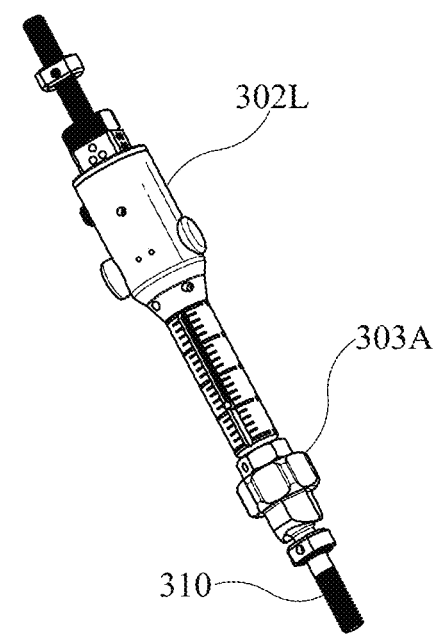
Figure 3C:
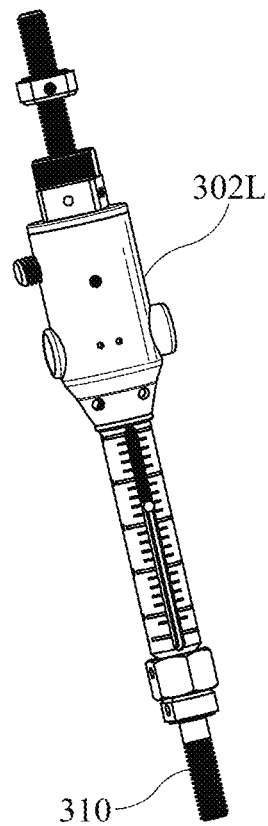

Referring now to FIGS. 3A-3C, there may further be provided a plurality of connectors 300 that may be used to connect first plate 100 and second plate 200. A connector 300 may be a structural element capable of carrying load at least generally along its longitudinal direction and possibly other components or directions of load or torque as well. For such a situation, the connector may be capable of being locked into a substantially rigid shape that resists further change of length or configuration. In general, connectors may be adjustable in either their length or their angular characteristics or both, as may be desired. Angular adjustment features may include, for example ball-and-socket joints.

A connector 300 may comprise a threaded post 310 in any of various places such as at an end of the connector 300. In conjunction with a threaded post 310, a nut may be utilized to secure a threaded end of a connector 300 to the plate 100, 200, 270, 289, 290, 291, through a hole or a slot in the plate 100, 200, 270, 289, 290, 291.

A connector 300 may comprise a first angle-adjustment mechanism, a length adjustment mechanism, and a second angle-adjustment mechanism. These may be provided in the order just given, although other orders are also possible. It is furthermore possible that connectors 300 may be provided that have different combinations of these features. For example, as just described, it is possible to provide a set of connectors 300 of various designs and various lengths. As illustrated in FIG. 3A, there could be provided a connector 300 having a first angle-adjustment mechanism 301A, a length adjustment mechanism, 302L, and a second angle-adjustment mechanism 303A. It is further possible (as illustrated in FIG. 3B) to provide a connector 300 having a length adjustment mechanism 302L and an angle-adjustment mechanism 303A. It is still further possible to provide a connector (not illustrated) having a first angle-adjustment mechanism. It is still further possible to provide a connector 300 (as illustrated in FIG. 3C) having a length-adjustment mechanism 302L. It is still further possible to provide a connector 300 that is a simple non-adjustable rod, which may be a threaded post 310 (not illustrated). These connectors 300 may be provided in various length ranges such that some or others can be used together in any combination. For example, in one part of an assembly, there could be a connector 300 containing a length adjustment and one angular adjustment, while in another part of the assembly there could be a connector 300 containing a length adjustment and two angular adjustments. Other combinations are also possible.

Figure 4A:
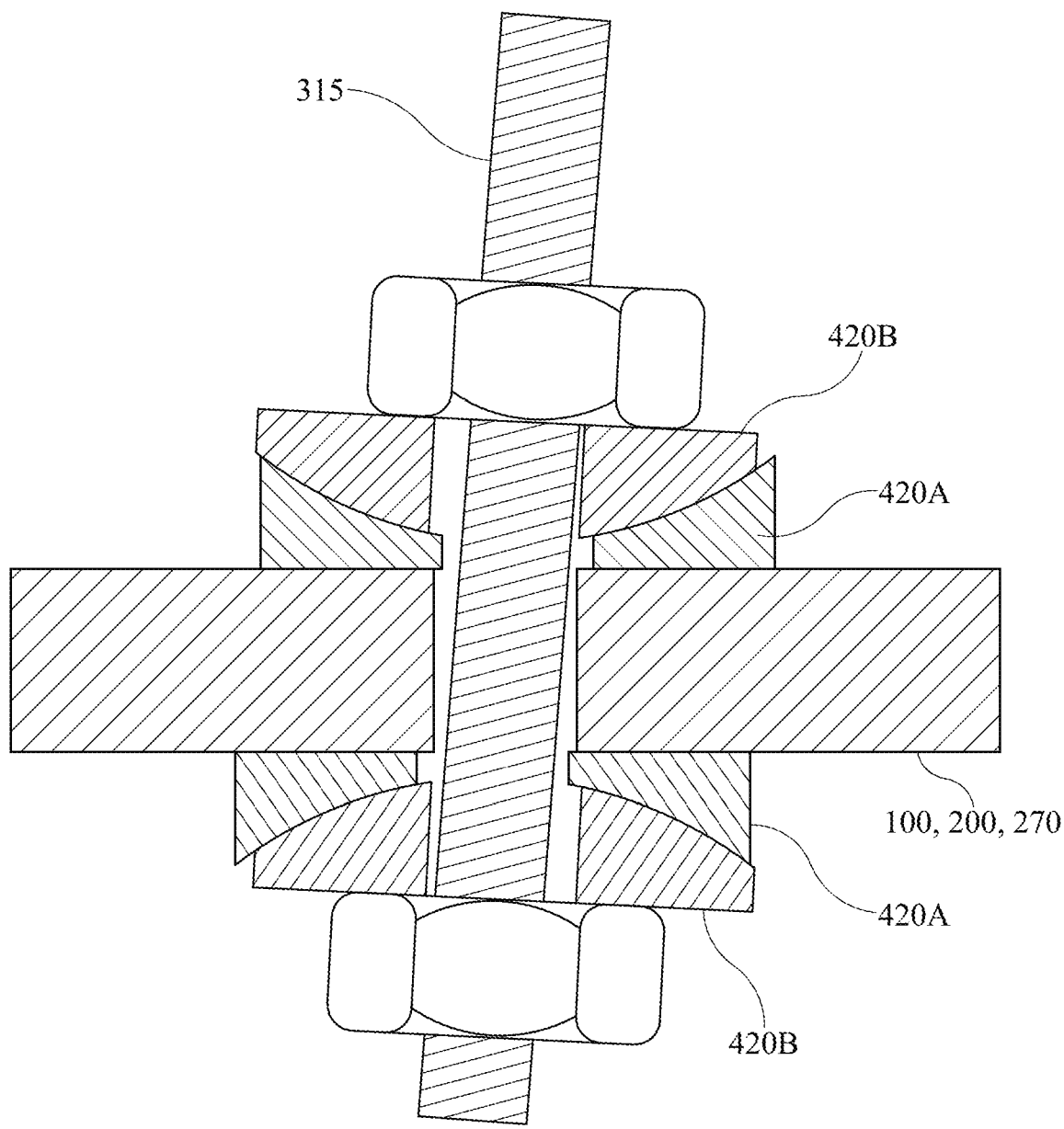
FIG. 4A shows a form of a bolted joint that can accept a certain amount of angular misalignment.
Figure 4B:
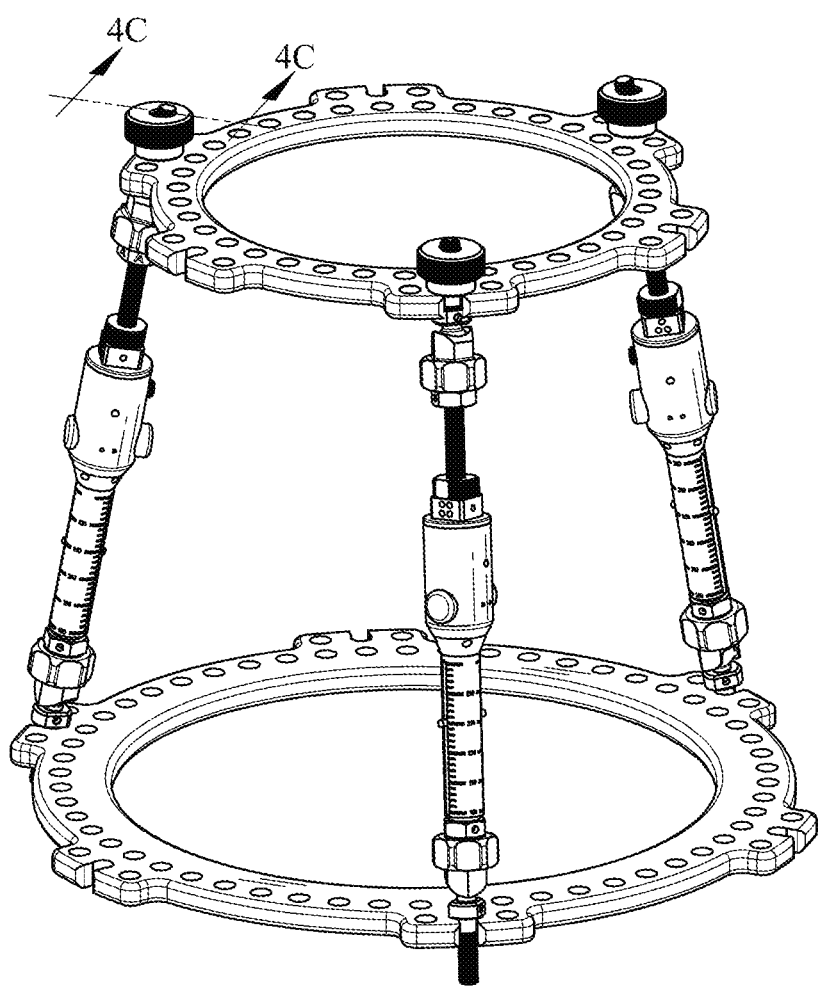
FIGS. 4B through 4E illustrate the use of a speed-nut to connect a threaded rod to a plate.
Figure 4C:
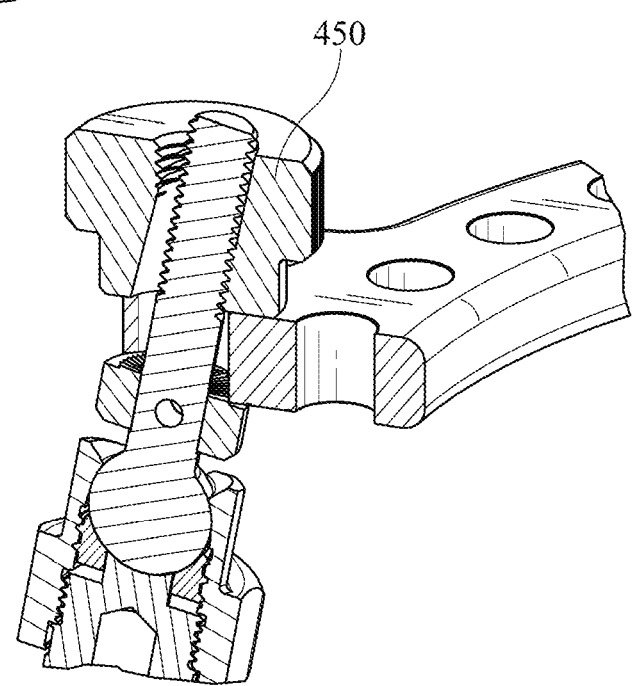
Figure 4D:
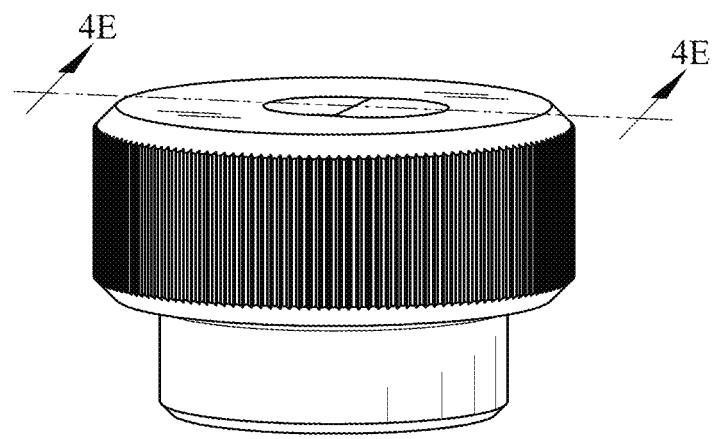
Figure 4E:
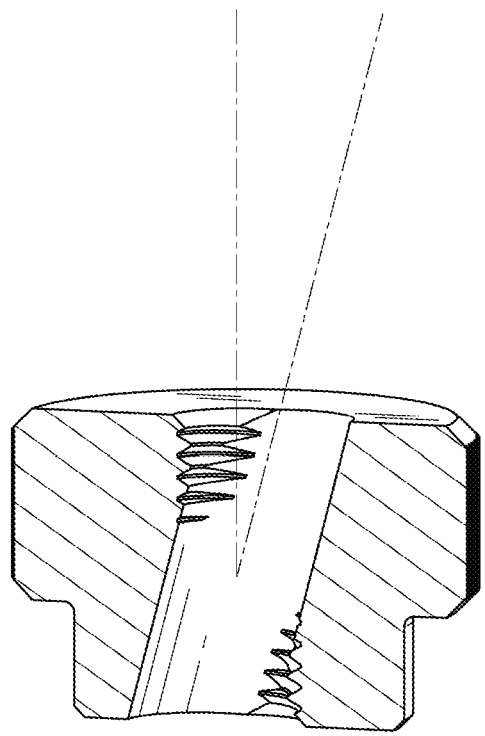
Figure 5A:
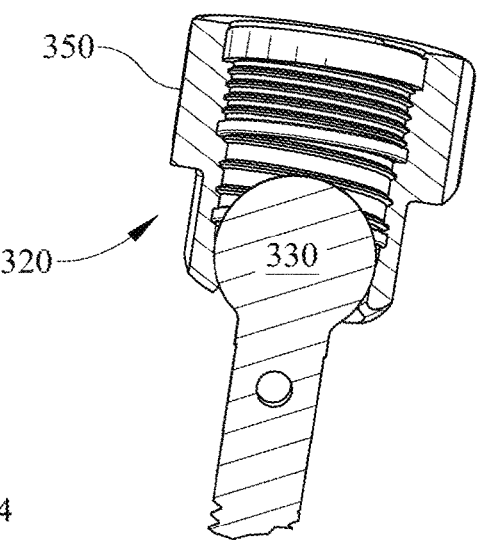
FIGS. 5A, 5B, 5C and 5D depict various views of the frictional components of the ball-and-socket joint and associated housing and the first and second frictional bearing components.
Figures 5B, 5C:
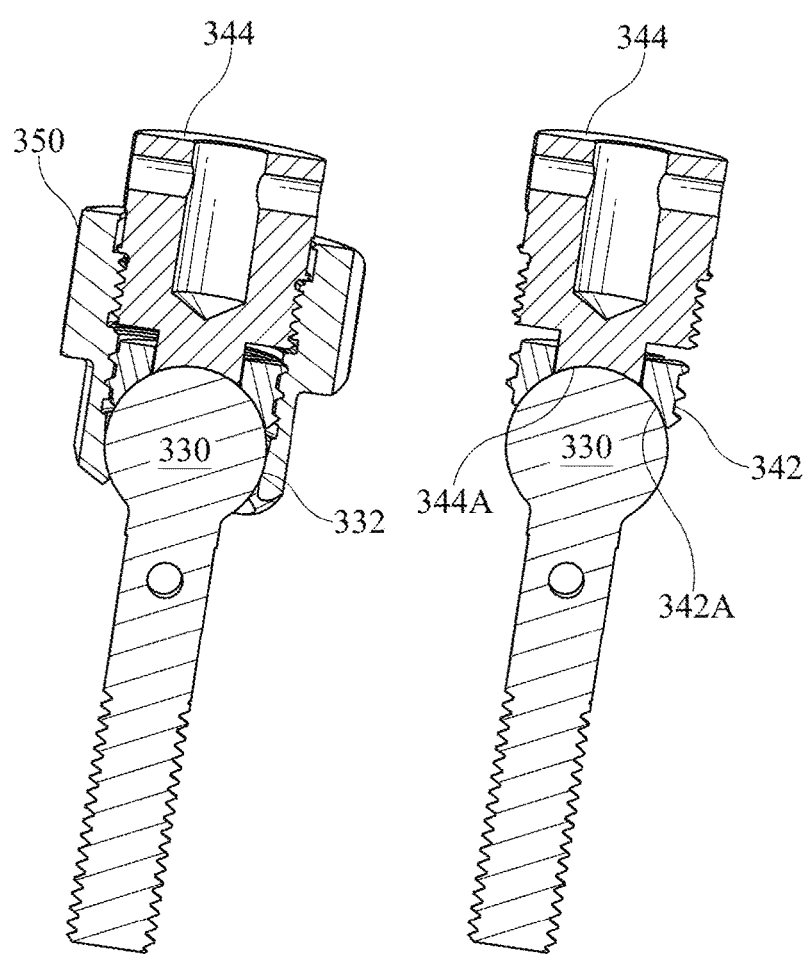
Figure 5D:
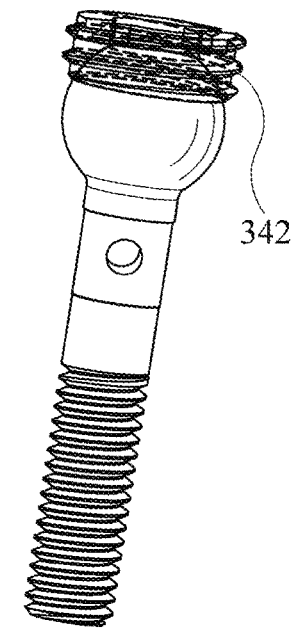

In connection with securing any type of threaded rod 315 to a plate 100, 200, 270, 289, 290, 291, one possibility is that the surfaces of the plate 100, 200, 270, 289, 290, 291 could be substantially parallel with each other, and the nuts or fasteners facing against both surfaces of the plate 100, 200, 270, 289, 290, 291 could have faces that are substantially perpendicular to their axes. In such a situation, the threaded rod 315 would be constrained to be substantially perpendicular to the plate 100, 200, 270, 289, 290, 291. However, another possibility is that, between the plate 100, 200, 270, 289, 290, 291 and a nut, there could be provided a matched pair of washers 420A and 420B. First washer 420A may have a concave surface and a first substantially flat surface opposite the concave surface. Second washer 420B may have a convex surface and a second substantially flat surface opposite the convex surface. The concave surface of first washer 420A and the convex surface of second washer 420B may be complementary to each other. For example, the concave and convex surfaces may be portions of spheres. The flat surface of first washer 420A and the flat surface of second washer 420B may be substantially parallel to each other when first washer 420A and second washer 420B are generally in a central or middle position relative to each other. However, first washer 420A and second washer 420B may also be capable of being angularly displaced relative to each other so that the flat surfaces of washers 420A, 420B may have a slightly tilted relationship relative to each other. Such a construct could allow the threaded post 310 to occupy a small range of angular orientations in addition to the position in which it is substantially perpendicular to the plate 100, 200, 270, 289, 290, 291. This is illustrated in FIG. 4A.

Referring now to FIGS. 4B, 4C 4D and 4E, in an embodiment of the invention, a connector 300 may be connected to a plate 100, 200, 270, 289, 290, 291 by a nut that may be referred to as a speed nut 450.

The speed nut 450 may have an internally threaded hole therethrough, thread while also having an angled unthreaded hole intersecting and partially overlapping the threaded hole at a slight angle. When the speed nut is rotated, the threads engage and lock onto the threaded shaft. This allows for quick attachment and security of the threaded rod or post.

In use during treatment of a patient, a speed nut 450 may be utilized to temporarily secure a threaded rod or threaded post to a plate 100, 200, 270, 289, 290, 291. This allows the nut to the tilted and slid down the threaded shaft, then tilted to a normal orientation where its internal threads engage the threaded rod, and be tightened by being rotated. At a later time, such as when all positioning has been completed, the speed nut 450 may be removed and replaced with a standard nut. Any relevant nut, whether a speed nut 450 or a standard nut, may be used if desired in combination with paired domed washers 420A, 420B as described in FIG. 4A.

Referring now to FIGS. 5A-5D, in embodiments of the invention, there may be provided a joint 320 that governs the relative angular position of one portion of the connector 300 with respect to another portion of the connector 300, and the joint may comprise a frictional relationship. The joint may comprise a ball-and-socket connection. A ball-and-socket connection may comprise a portion of a sphere. The sphere or ball 330 may be attached to or integral with an end of a rod such as threaded post 310, with the diameter of the ball 330 being greater than the diameter of the attached rod. The ball 330 may be received within a socket 332 that also may comprise a portion of a spherical surface.

In an embodiment of the invention, there may further be provided a non-user-adjustable frictional bearing component 342 and a user-adjustable frictional bearing component 344 that each may bear frictionally against the ball 330 in different locations. As a result, the non-user-adjustable frictional bearing component 342 and the user-adjustable frictional bearing component 344 may individually or in combination exert on the ball 330 force that may control the joint's motion or the resistance to motion. It is possible that one of these bearing components may exert force on the ball 330 in all circumstances while the other of these bearing components may exert force on the ball only when certain components of the system are tightened.

It is possible that the non-user-adjustable frictional bearing component 342 may be located inside the assembly in such a way that the user does not have access to change its frictional characteristics, while the user-adjustable frictional bearing component 344 may be located such that the user has access to change its frictional characteristics from external access during normal use of the apparatus. It is possible that the non-user-adjustable frictional bearing component 342 may be set such as to provide a nominal friction that may allow the connector 300 assembly to positioned at a desired angle and to maintain that angle against a force or torque that would be produced by the nominal weight of the components and perhaps slightly more than the nominal weight of the components, but that friction can be overcome within a range of force or torque that can be produced by the bodily exertion of a physician who is installing the apparatus. It is possible that the non-user-adjustable frictional bearing component 342 may be in the shape of a ring, and it is possible that the user-adjustable frictional bearing component 342 may have a bearing surface that is a portion of a sphere.

It is possible that the user-adjustable frictional bearing component 344 may be capable of being adjusted by the user during normal use. It is possible that, within the permitted range, such adjustment may provide sufficient force to rigidly and solidly lock the joint to retain its configuration against magnitudes of force and/or torque that it may experience. Locking may be achieved either by hand tightening or by tightening with a tool, depending on design details.

The joint may comprise a housing 350 that has the internal spherical surface that is socket 332, and may also comprise internal threads that engage with mating frictional bearing components. The non-user-adjustable frictional bearing component 342 may include a first frictional surface 342A, and the user-adjustable frictional bearing component may include a second frictional surface 344A. The first frictional surface 342A may be a portion of a sphere. The second frictional surface 344A may be a portion of a sphere. The non-user-adjustable frictional bearing component 342 may engage with first housing threads and the user-adjustable frictional bearing component 344 may engage with second threads of the housing 350. It may be understood that the thread by which the non-user-adjustable frictional bearing component 342 engages the housing 350 and the thread by which the user-adjustable frictional bearing component 344 engages the housing 350 may be either the same thread or different threads. If they are the same thread, the thread may be interrupted by a groove, although this is not essential. If they are different threads, as illustrated, then the further-in thread for the non-user-adjustable frictional bearing component 342 may have a major diameter that is smaller than the minor diameter of the user-adjustable frictional bearing component 344. This relation can serve to insure that the non-user-adjustable frictional bearing component 342 may enter the region designated for it by passing through the region designated for the user-adjustable frictional bearing component 344. It may be understood that other designs and other materials are also possible for creating the friction between the non-user-adjustable frictional bearing component 342, or in general any first component, and the ball 330.

The non-user-adjustable frictional bearing component 342 may exert force on a portion of the spherical surface of the ball 330, and the user-adjustable frictional bearing component 344 may exert force on a different portion of the spherical surface of the ball 330. For example, when the user-adjustable frictional bearing component 344 engages with the housing 350 in such a way as to exert significant axial force on the ball 330, there might still be a gap between the user-adjustable frictional bearing component 344 and the non-user-adjustable frictional bearing component 342, so that the user-adjustable frictional bearing component 344 does not increase the force exerted by the non-user-adjustable frictional bearing component 342 on the ball 330.

The non-user-adjustable frictional bearing component 342 may be dimensioned and installed so that it exerts a relatively gentle frictional force on the ball 330 at all times. The user-adjustable frictional bearing component 344 may be used in such a way that when desired it exerts a large force on the ball 330 sufficient to lock the joint against all anticipated forces, and when not desired, it exerts substantially zero force on the ball 330. In more detail, the force exerted by the user-adjustable frictional bearing component 344 may be of two different magnitudes, one applied by hand and another larger force applied through the use of tools such as wrenches. In order for the non-user-adjustable frictional bearing component 342 to operate as just described, it is possible that the non-user-adjustable frictional bearing component 342 may be made of a material that has good sliding properties with respect to the ball 330. The non-user-adjustable frictional bearing component 342 may be made of a material different from the second or user-adjustable frictional bearing component 344. The non-user-adjustable frictional bearing component 342 may be made of a metal although it could alternatively be made of a polymer. The housing 350 may be made of a relatively stiff material such as a metal or a stiff polymer. During manufacture, the non-user-adjustable frictional bearing component 342 may be placed into its location and tightened to a desired extent, and then the ball joint 320 may be tested for its frictional properties in response to an applied torque, such as to see if it slips at desired torque and holds for another desired torque. If any of these torque characteristics are not achieved, then the non-user-adjustable frictional bearing component 342 may be tightened or loosened in its housing 350 so as to achieve the desired frictional behavior. It may be understood that the threaded engagement between the non-user-adjustable frictional bearing component 342 and the housing 350 may permit adjustment of how much friction exists in the joint in ordinary circumstances, absent the tightening of the user-adjustable frictional bearing component 344.

In embodiments of the invention, it may be possible for the person who is setting up the apparatus on the patient to tighten the connector 300 into a locked configuration using only one hand. For example, if the plates 100, 200, 270, 289, 290, 291 are in a desired configuration, the medical personnel (user) could grasp housing 350 with one hand and rotate it in a desired direction and thereby tighten the ball-and-socket joint against further angulation in any direction. If the tightening is done in a one-handed manner, the torque applied by the user could be reacted against the rest of the external fixation system, which might include some other part of the external fixation system being held by the other hand of the user or by another person.

Figure 6A:
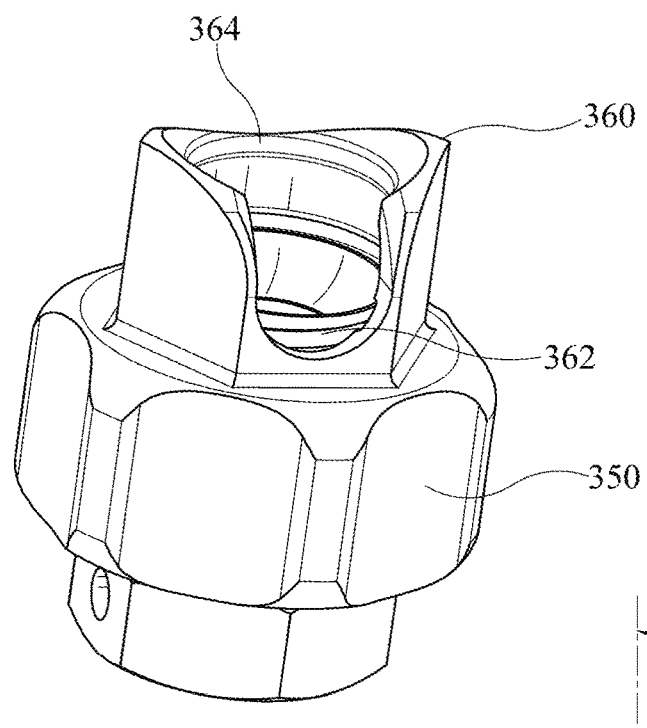
FIG. 6A depicts the angularly adjustment joint of the connector.
Figure 6B:
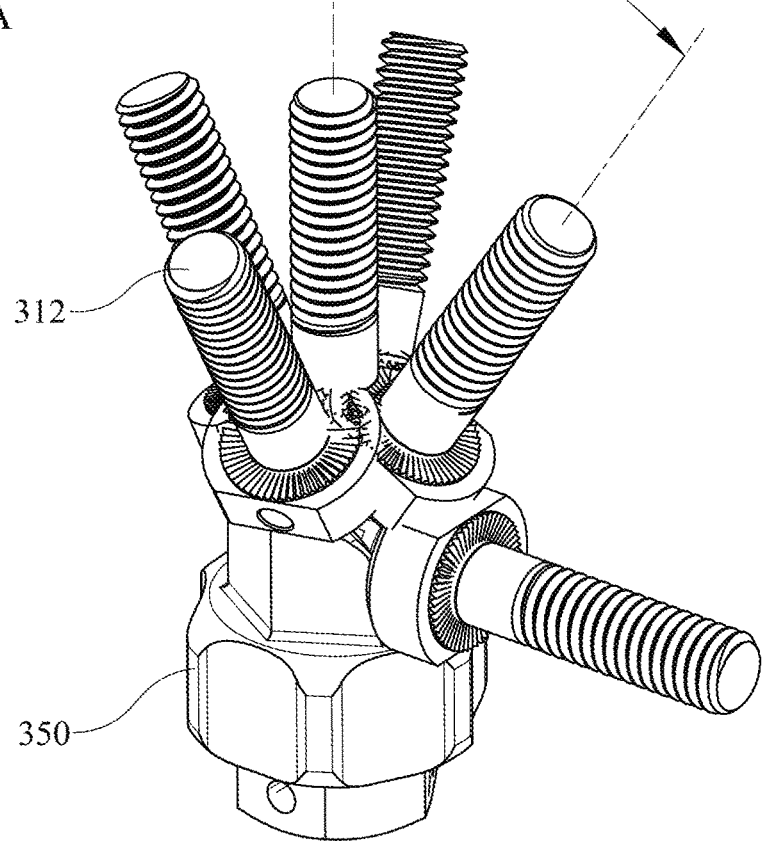
FIG. 6B is a composite view of a number of permitted positions of the angular adjustment of the joint of the connector.
Figure 7A:
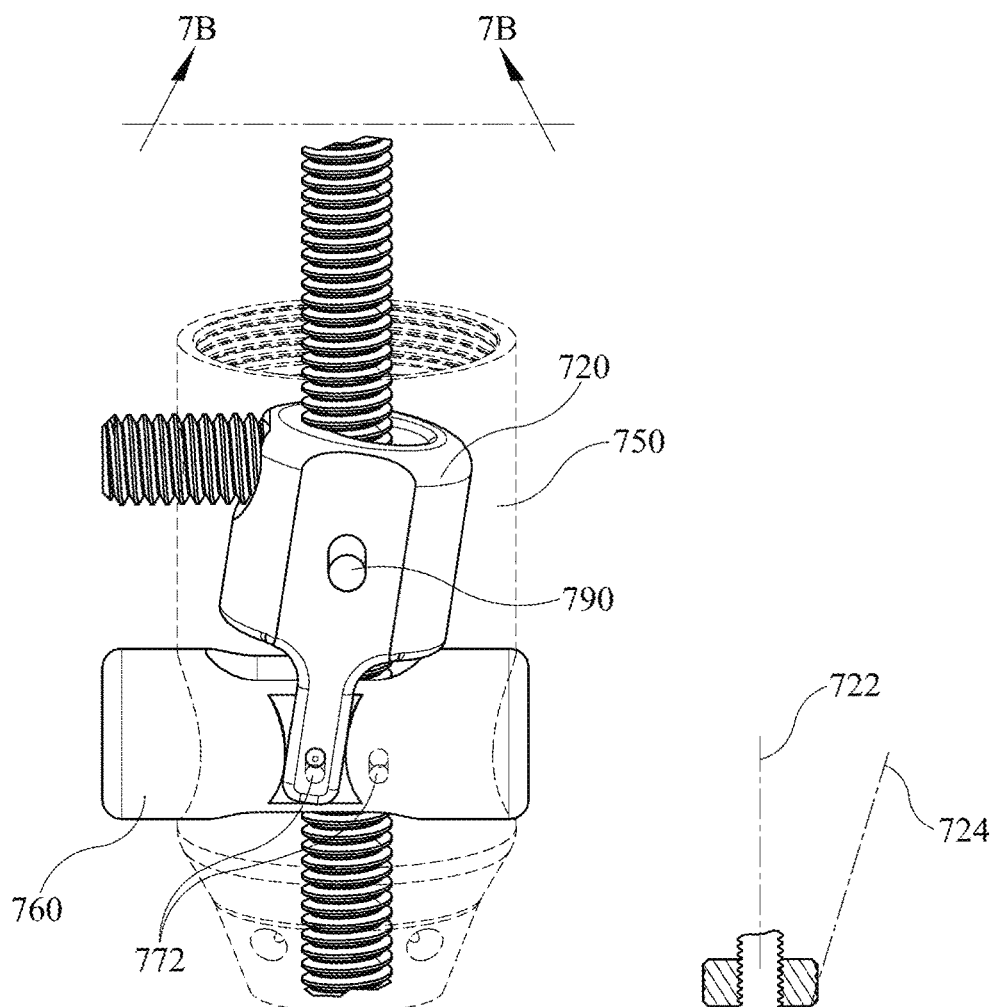
FIGS. 7A and 7B depict a slider and a tiltable nut for engaging or not engaging a threaded rod.
Figure 7B:
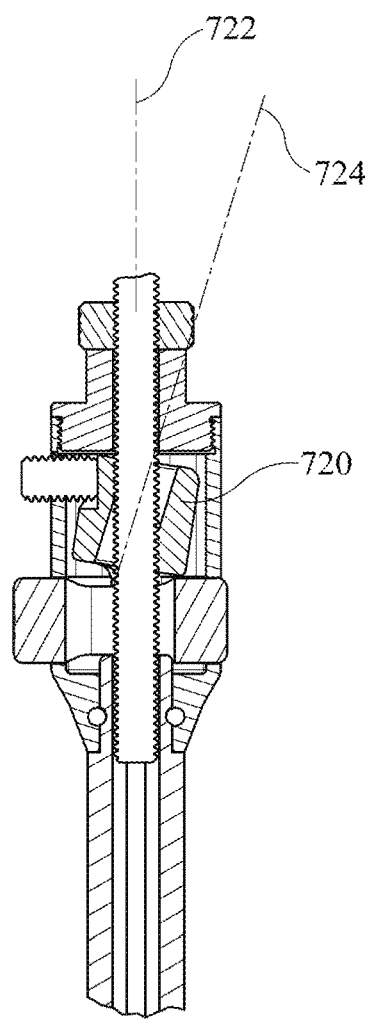
Figure 8:
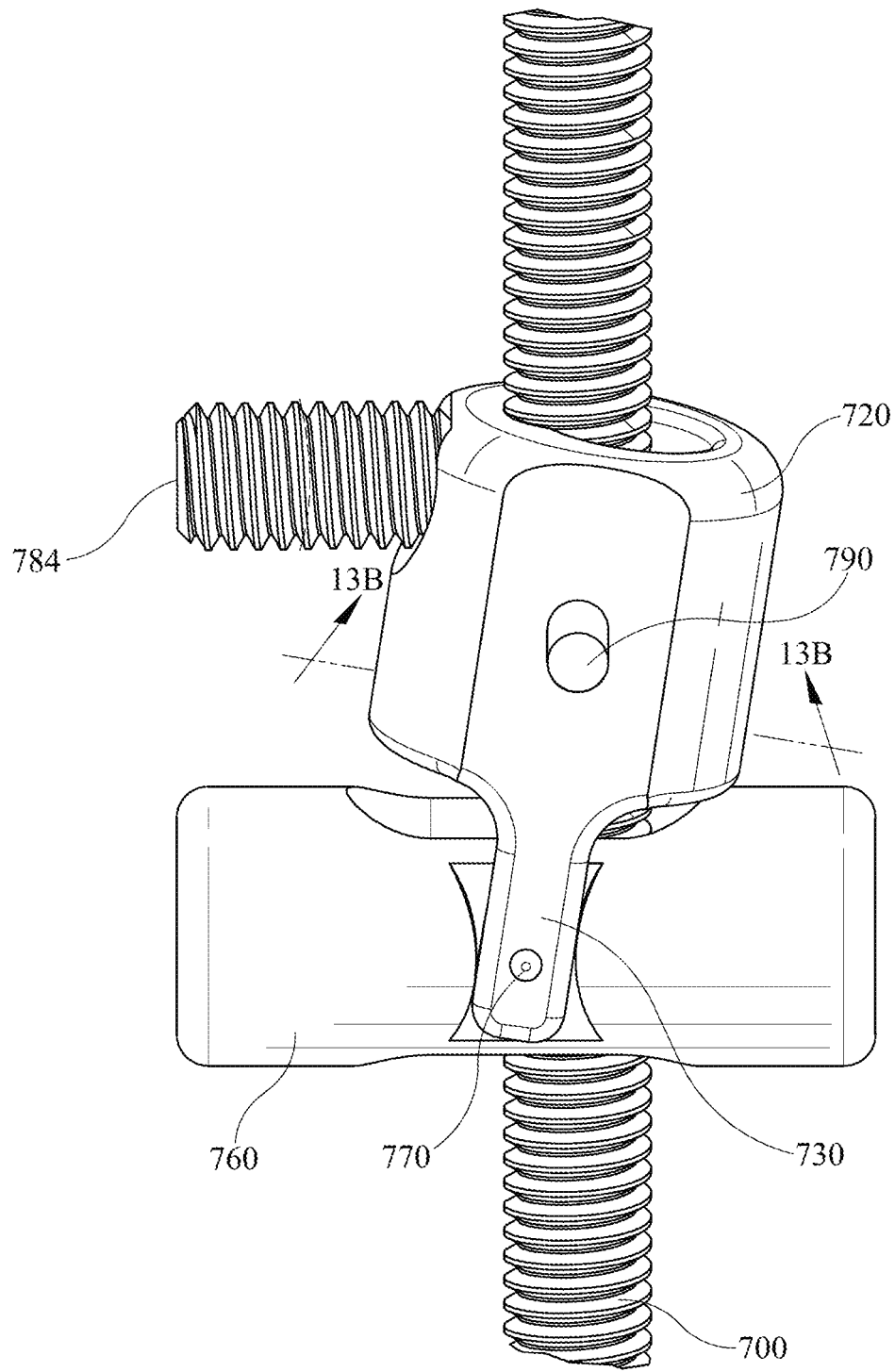
FIG. 8 depicts, in isolation, the slider and the tiltable nut, and the threaded rod that the tiltable nut engages with in certain situations, and a setscrew.
Figure 9:
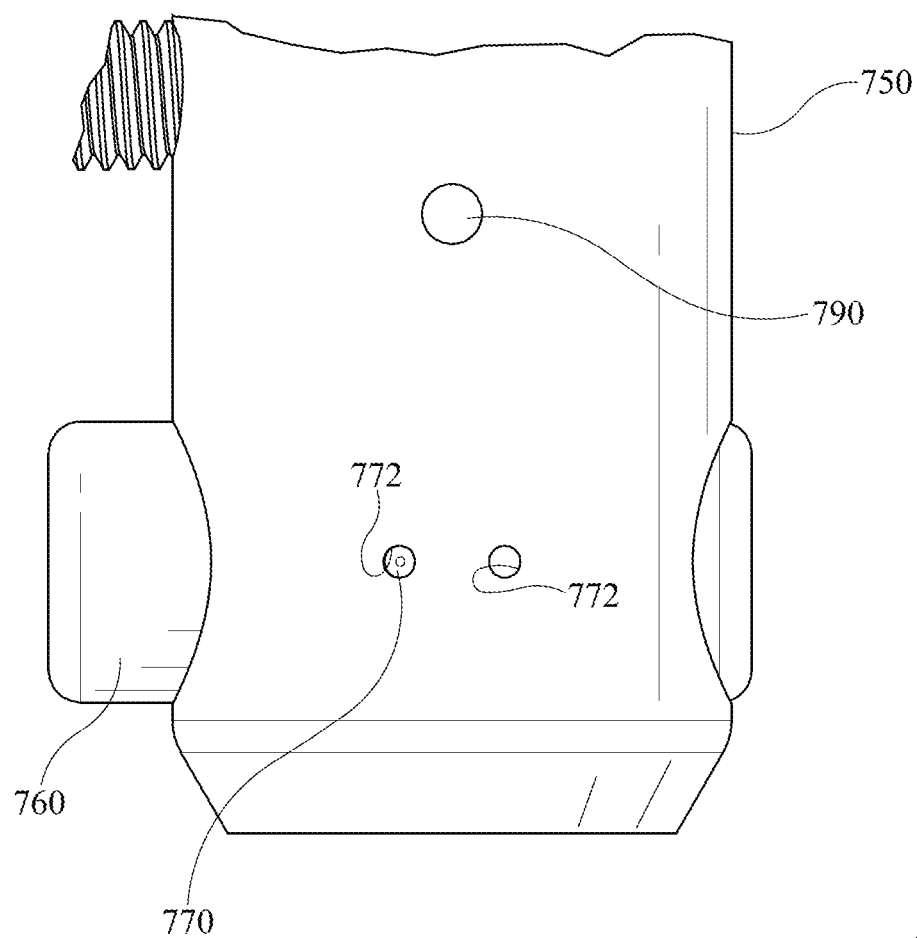
FIG. 9 is a side view of the slider in its housing, also showing the dome-bump visible through the corresponding hole in the housing.
Figure 10:
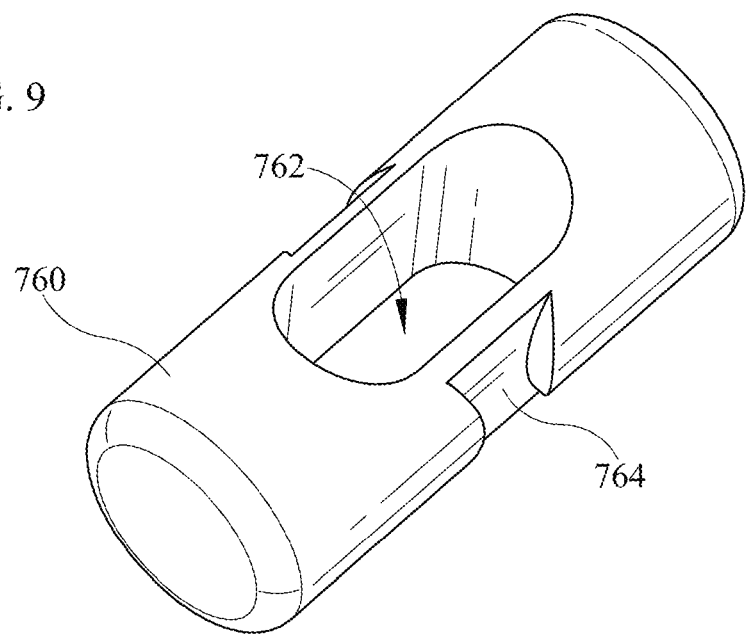
FIG. 10 shows a three-dimensional view of the slider and the housing.

Referring now to FIGS. 6A-6B, in an embodiment of the invention, there may be provided a specific range of permitted angular motion of the rod 312 of a connector 300 with respect to the housing 350 of a connector 300. There may be defined a central axis of rod 312 such that it aligns with another part of connector 300 making up the other end of the angular joint. Zero angular deflection may be considered to be when the rod 312 aligns with the central axis of the device, or when the axis of the rod extending from one end of the angular joint aligns with the axis of the rod extending from the other end of the angular joint. Angular deflection can be defined as angular departure of the axis of the rod 312 from the central axis of the other rod of the joint. In general, the pattern of what is the permitted angular deflection at various places on the circumference could be any pattern that is desired. In particular, the pattern could be a non-uniform pattern in which different amounts of angular deflection are permitted in different places on the circumference. The permitted angular deflection could be large at one place on the circumference, and could have other different possibly smaller values at other places on the circumference, and could be zero if desired at desired places on the circumference. The rod 312 of a connector 300 can be constrained such that it can lean away from its axis by no more than a first angular extent in some directions, and in one location it can lean over to a greater angular extent than at other angular locations. For example, the angular extent can be chosen to be 18 degrees (with respect to central axis) in most directions, and in the particular location it can be chosen to be 90 degrees. These numerical values are just examples, and of course other values could be chosen. It is further possible that in some places the allowed angle of deflection away from the axis could be zero degrees.

In the physical construction of such a connector, the housing 350 may have a rim 360 that proceeds around the circumference in a shape that is suitable to provide the desired circumferential distribution of permitted angular deflection. In another way of describing it, the extent by which the socket encloses the ball may be non-uniform as a function of position around said perimeter. The height of the rim 360 at particular places along the circumference can be any distribution that may be desired, as long as it is sufficient to keep ball 330 captured within the connector. For example, the rim may be at a given level for a substantial part of a circumference, and then at a certain point 362, the rim may dip closer to the center of the ball 330 with a major dip 362. The width of the major dip 362 may be at least as wide as the rod 312 that is immediately adjacent to ball 330. Furthermore, there may also be a minor dip 364, which may be directly opposed to the major dip 362. For example, the region of the large dip may have a large permitted angle that is approximately 90 degrees away from the axis, while the rest of the circumference (other than the small dip) has a permitted angle no greater than 18 degrees.

In particular, when such a connector is in use, the connector 300 may be oriented with respect to the overall apparatus such that the direction in which a large angle of motion is allowed may be such that the connector 300 is capable of swinging outward away from the limb that is being fixated. In such a situation, the major dip 362 may be facing generally away from the patient's limb. Such increased angulation can allow for the addition and removal of other components. This may also be useful to allow the medical professional treating the patient to temporarily swing one connector 300 away from the assembly so as to provide access for X-ray imaging or other forms of imaging or for other medical treatment purpose. As illustrated, it would be possible to perform such swinging-away of one connector 300 without disturbing any of the other connectors 300.

The minor dip 364 may serve to allow the rod 312 to angle itself inwardly to a greater extent than it is allowed to angle itself sideways (circumferentially along the ring or plate 100, 200, 270, 289, 290, 291). Although the illustration shows that the circumference has one minor dip 364 in addition to the major dip 362, it would of course be possible to have any number of minor dips. In general, the shape of the circumference 360 could be any desired shape.

In FIG. 6B, there is shown a superposition of several possible positions of rod 312 with respect to the housing 350. The envelope of the various illustrated positions would be the complete range of possible positions that rod 312 could occupy. This illustrates the range of permitted motion that corresponds to the circumference shape that is illustrated in FIG. 6A.

Referring now to FIGS. 7-13, in regard to adjustment of the length dimension of a connector 300, in an embodiment of the invention, a connector 300 may comprise a mechanism that in some circumstances allows rapid translation to change the length of the connector 300, and in other circumstances allows only fine adjustment of the connector 300 length associated with a rotational motion. Such a mechanism may comprise a threaded rod 700 having external threads.

Such a mechanism may further comprise a tiltable nut 720 that may occupy either of two tilt positions. A tiltable nut 720 may have a first hole 722 therethrough that has a female thread suitable to engage with the external thread of the threaded rod 700 or threaded post 310 of a connector 300. The tiltable nut 720 may also have a second hole 724 that may be an unthreaded hole. The first, threaded hole 722 and the second, unthreaded hole 724 may intersect with each other at an angle so as to form a combined void space within tiltable nut 720, such that the combined void space has a somewhat irregular shape whose interior surface is partially threaded and partially unthreaded. There may be an intersection point where the axis of the threaded hole and the axis of the unthreaded hole intersect with each other.

When the parts of the mechanism are arranged so that the when the tiltable nut internal thread is disengaged from the threaded rod external thread, the tiltable nut 720 can translate along the threaded rod 700 guided by the unthreaded hole. This allows the tiltable nut 720 to be slid along the threaded rod 700 quickly. When the tiltable nut 720 is an appropriate tilt position, the internal threads of the tiltable nut 720 engage the threaded rod 700. In this configuration, the tiltable nut 720 can be rotated while threadedly engaged with the threaded rod 700, and such rotation results in fine adjustment of the length of the connector 300.

Taken together, these various features allow for both coarse adjustment (quick sliding of one part relative to another) and fine adjustment (translation based upon rotation of a threaded element). In the fine adjustment configuration, the length of the connector 300 may be adjusted by rotation of the housing, causing rotation of tiltable nut 720 with respect to threaded rod 700, and resulting in translation.

Shifting between the coarse adjustment and fine adjustment positions may be achieved by a tilting adjustment to adjust the angle of the tiltable nut 720 relative to the threaded rod 310, or by other means. Tilting can be achieved by a sliding motion of the slider 760, which may cause the tiltable nut 720 to tilt.

The tiltable nut 720 may further comprise a pair of extension arms 730 extending from the tiltable nut 720. The pair of extension arms 730 may form a yoke.

The tiltable nut 720 may be tiltably mounted in its housing so that it can occupy at least two defined different positions. One of the positions may create engagement of the nut threads with a threaded rod 700. The other position may have no thread engagement with the threaded rod 700.

The pivot 790, which may be a pair of opposed cylindrical projections from tiltable nut 720, may have a pivot axis that may be substantially pass through the intersection point where the axis of the threaded hole and the axis of the unthreaded hole intersect with each other. The housing 750 may have a corresponding hole(s) to receive pivot 790.

The slider 760 may have a longitudinal axis and, generally perpendicular to its longitudinal axis, may have extending therethrough a through-slot 762. The through-slot 762, in its own cross-section, may have the shape of a rounded-rectangle or other elongated shape. The through-slot 762 may have internal dimensions that are sufficiently large for the threaded rod 700 to extend therethrough. The through-slot 762 may have internal dimensions that are large enough for the threaded rod 700 to extend through the through-slot at either of the two extreme positions of the slider 760 and any position between the two extreme positions.

The slider further may have two recesses 764 at places that are opposed to each other. The recesses 764 may be dimensioned and located so that extension arms 730 of the yoke may be received loosely within the recesses 764, and so that extension arms 730 may be urged to move when slider 760 translates. The motion of extension arms 730 can follow the translation of slider 760 so as to cause tiltable nut 720 to tilt in response to such translation. The shape of recesses 764 may be such as to provide some looseness in the fit between extension arms 730 and recesses 764 and also provides the ability of extension arms 730 to occupy some range of angles with respect to slider 760, as would occur in the normal course of motion of slider 760 through its permitted range of translation motion.

Figure 12:
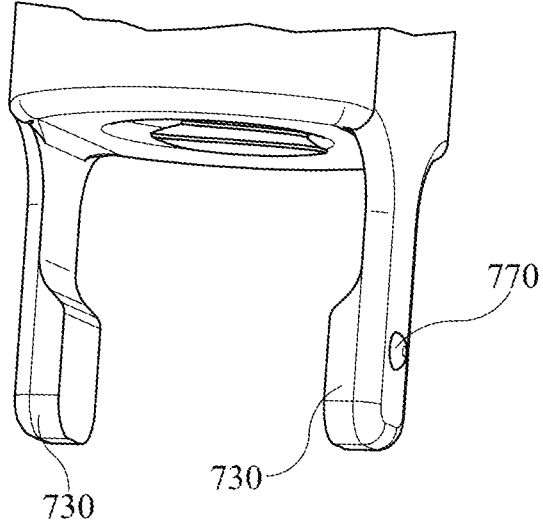
FIG. 12 is a three-dimensional view of only a portion of the tiltable nut including its extension arms.

Still further, there may be provided on extension arms 730 a pair of dome-bumps 770 on the outside of the extension arm 730. This is best illustrated in FIG. 12 and in FIG. 9 the dome-bump 770 is also visible through the corresponding hole in the housing. Also, there may be provided in the housing 750 a pair of receiving spaces 772 (which may be through-holes or internal recesses) into which the dome-bumps 770 may reside for certain positions of slider 760. The dome-bump(s) 770 and the receiving space(s) 772 may be located and dimensioned with respect to each other so that when the dome-bump 770 is residing in the receiving space 772, there is a certain amount of force needed to move the dome-bump 770 out of the receiving space 772 and start it on its travel to the other position. Also, for motion of the dome-bump 770 in an opposite direction of motion, such motion may be completely prevented. After the dome-bump 770 has exited from the receiving space 772, the dome-bump 770 may be able to translate while experiencing a certain amount of friction, but less force than the force to initiate its motion by exiting from the receiving space 772. Although it is not wished to be limited to this explanation, the deformation that permits the dome-bump 770 to escape from the receiving space 772 may be deformation of the cantilever of the extension arm 730. Other sources of deformation are also possible. The geometric details of the dome-bump 770 also may be chosen so as to provide desired characteristics of the dome-bump 770 entering into the receiving space 772 and leaving from the receiving space. For example, the slope or tangent angle of the dome-bump 770 where it meets the extension arm 730 may have an angle of less than about 45 degrees, or less than about 30 degrees, with respect to the adjacent surface of extension arm 730, so that the act of sliding the dome-bump 770 past receiving space 772 causes the dome-bump 770 to be deflected inward. This is best illustrated in FIG. 13C. The entering of the dome-bump 770 into the receiving space 772, and the leaving of the dome-bump 770 from the receiving space, may be designed so that these actions provide tactile feedback to the user of the apparatus when either of these positions is entered or departed from. It is further possible that these same actions may provide an audible feedback to the user, such as a clicking sound, when certain actions occur.

It can be appreciated that with the described connector 300, it is possible to switch between free translation and fine adjustment with just one hand operating one button. The feature of free translation allows the medical personnel to position the plate and the bone in the ideal position before locking the connectors. This feature provides additional flexibility and ease of use for the surgeon. When the thread is engaged the connector can be advanced such as at the standard rate of 1 mm per revolution of the external rotatable piece. This may be used for distraction or compression of bones.

Still further, there may be provided a setscrew 784 or similar means that can lock the tiltable nut 720 in a desired position, subject to removal only by deliberate action by the user such as loosening the setscrew. Furthermore, the setscrew 784 can be tightened to a first extent and also to a second extent. The first extent of tightening can be such that the setscrew 784 positively prevents the slider 760 from translating and thereby prevents disengagement of the tiltable nut 720, but still allows the rotation of the assembly with respect to the threaded rod 700, thereby permitting fine adjustment. The second extent of tightening can be such that the setscrew 784 causes the tiltable nut 720 to press against the threaded rod 700 with sufficient force that friction between the tiltable nut 720 and the threaded rod 700 prevents any rotation of the housing or the tiltable nut 720 with respect to the threaded rod 700, and therefore prevents any adjustment of length of the connector.

Referring now to FIGS. 14A-15B, in embodiments of the invention, there may be provided provisional alignment clamps 1410, 1420, 1430. For example, for treatment of a lower extremity injury, it may be desirable to provide, control or adjust space between the plates 100, 200, 270, 289, 290, 291 and the leg. Such provisional alignment clamps 1410, 1420, 1430 may have a body 1440 that is attachable to the plates 100, 200 or to the footplate 270 or to plates 289, 290, 291. At an opposite end, such provisional alignment clamps 1410, 1420, 1430 may have a limb interface part 1450 that is roughly complementary to a bodypart of the patient. The limb interface part 1450 may be shaped in a way that is compatible with and generally supportive of the portion of the patient's limb that it is intended to bear against. For example, there may be provided limb interface parts 1450 that are complementary to any one or more of a foot (left side and right side), a heel, and a calf. The provisional alignment clamp limb interface part could be flat, cupped, or any other appropriate geometry, and could have any desired orientation with respect to the remainder of the provisional alignment clamp 1410, 1420, 1430.

The provisional alignment clamp 1410, 1420, 1430 may have a base part 1440 that can attach substantially rigidly to one of the plates 100, 200, 270, 289, 290, 291, and it may have the limb interface part 1450. The limb interface part 1450 may be movable with respect to the base part 1440, in at least one direction. As illustrated, the limb interface part 1450 is movable with respect to the base part 1440 in one translational direction, and it is not movable in any other translational direction and is not rotatable in any rotational sense. However, it would be equally possible that the apparatus could be made so that a provisional alignment clamp 1410, 1420, 1430 is rotatable with respect to its base part 1440 or with respect to one of the plates 100, 200, 270, 289, 290, 291.

Furthermore, the provisional alignment clamps 1410, 1420, 1430 may have a sliding mechanism, which may be a ratchet mechanism, which may include a ratchet rack 1460. The ratchet mechanism may include a spring-loaded pawl that engages the teeth of the ratchet rack 1460. For example, the teeth may have a favored direction. There may be a direction of preferred translational motion that may be determined by the configuration of the teeth of ratchet rack 1460. The ratchet mechanism may be such that it is easy to push the limb interface part toward the patient's bodypart, but backing the limb interface part 1450 away from the patient's bodypart may involve the user to perform an action to release the ratchet mechanism. Releasing may be achieved by pulling ratchet release handle 1470 away from the body of provisional alignment clamp 1410, 1420, 1430.

Alternatively, instead of a ratchet, the moving mechanism could be a slide, a threaded mechanism, or any other moving mechanism. The sliding mechanism may be such as to allow translation but prevent rotation. Alternatively, if desired, certain degrees of rotation could also be allowed (not illustrated herein).

The ratchet may provide an audible indication of progression (e.g. a click at the passage of each individual tooth of the ratchet) when the limb interface part 1450 is advancing away from the base part 1440, i.e., toward the patient's limb. The ratchet may provide tactile indication of progression. The ratchet could provide both audible and tactile feedback.

Multiple provisional alignment clamps 1410, 1420, 1430 can be placed at each plate 100, 200, 270, 289, 290, 291 or level as desired. A typical usage would include provisional alignment clamps 1410 for the foot, which may exist in left and right versions that may be mirror-images of each other, and a provisional alignment clamp 1420 for the heel of the foot, and a provisional alignment clamp 1430 for the calf of the leg.

The provisional alignment clamps may be used to allow for the surgeon to provide a controlled and uniform space between the plates 100, 200, 270, 289, 290, 291 and a respective portion of the patient's leg. The provisional alignment clamps 1410, 1420, 1430 may provide for secure and precise positioning of the patient's leg within the plates 100, 200, 270, 289, 290, 291. After other parts of the External Fixation System have been put into place or locked into place, the provisional alignment clamps 1410, 1420, 1430 may be removed.

FIGS. 15A, 15B are photographs of skeletal mock-ups of the leg and foot, with provisional alignment clamps being used.

An external fixation system of the invention may further comprise bone-contacting hardware for mechanically connecting with bone or pieces of bone. Such bone-contacting hardware may include longitudinal bone connection devices, which may be K-wires and half-pins. The hardware may further comprise hardware for attaching the longitudinal bone connection devices to plates 100, 200 or footplate 270 or plates 289, 290, 291.

Referring now to FIG. 16A, a K-wire (Kirschner wire) 1600, as illustrated, may be an elongated generally cylindrical structure that has a moderate stiffness in bending. A typical K-wire 1600 may be made of a biocompatible metal and may have a diameter of less than approximately 2 mm. A K-wire 1600 may have a substantially constant cross-section over at least a large portion of its length, and may be substantially straight. This typical diameter makes the K-wire somewhat easy to bend, and a K-wire 1600 may be notably more flexible in bending than the half-pin that is described later.

In use, a K-wire 1600 may enter through the patient's skin at one side of the treatment site (an entrance site), and it may go through the patient's bone, and it may exit through the patient's skin at another opposed side (the exit site) of the treatment site. The K-wire 1600 may be mechanically supported outside the patient's body both near the entrance site and near the exit site.

At least one end a K-wire 1600 may have a specially formed tip 1610, which may be different from the rest of the K-wire 1600. The tip 1610 may be sharp such as to aid in forming a passageway through bone or other tissue. The other end of the K-wire 1600 may be blunt. A blunt trailing end may be useful in case it is helpful for the medical personnel to push on an end of the K-wire 1600 to aid its penetration through tissue or bone. Other end shapes are also possible.

During the procedure the K-wires 1600 may be inserted through the skin and bone and extend all the way through the limb that is being externally fixated, emerging from the limb in two places. A K-wire 1600 may be provided in lengths longer than the anticipated length during use, with the intent that excess may be cut off when fixation has been completed.

In an embodiment of the invention, there may be provided at least one K-wire alignment guide 1650. The K-wire alignment guide 1650 may attach to the plate 100, 200, 270, 289, 290, 291 in any known mechanical way, which may include snapping or screwing into one of the holes in plate 100, 200, 270, 289, 290, 291, resting on top of the plate 100, 200, 270, 289, 290, 291, snapping or attaching around the plate 100, 200, 270, 289, 290, 291, or attaching in or adjacent a hole in the plate 100, 200, 270, 289, 290, 291.

The K-wire alignment guide 1650 may have a slot 1660 therethrough that extends along the longitudinal direction of the alignment guide 1650. The width of the slot 1660 may generally be larger than the diameter of the K-wire 1600, perhaps only slightly larger. However, at least one end of the slot 1660, the K-wire alignment guide 1650 may have a crosswise dimension of the opening therethrough that may be wider than for other portions of the slot 1660. For example, such wider portion 1664 may be a portion of a round hole whose diameter is greater than the width of the remainder of the slot 1660 and is greater than a diameter of a K-wire 1600. Such a feature may make it easy to initially feed the K-wire 1600 through the alignment guide 1650. However, it is not required that the hole have a greater diameter, or even that the hole be circular in its cross-sectional shape.

The K-wire alignment guide 1650 may have a slidable piece 1670 that interacts with the outside of the K-wire alignment guide 1650 and is able to slide vertically with respect to the K-wire alignment guide 1650. The slidable piece 1670 may surround the outside of the K-wire alignment guide 1650. The slidable piece 1670 may have a clamping device such as a setscrew that may exert force on the K-wire alignment guide 1650. The sides of the slot 1660 may be of a sufficient length and thickness so that they may deflect or deform upon exertion of force by the slidable piece 1670 upon a side of the slot 1660, so as to grip the K-wire 1600 and secure it in a desired position. The K-wires 1600 need not always align with the surface of the plate 100, 200, 270, 289, 290, 291. In this embodiment an instrument, the K-wire alignment guide 1650, is utilized to help stabilize the K-wire 1600 during its insertion. The K-wire 1600 may be inserted through the alignment guide slot 1660 and may rest on the slidable piece 1670. The position of the slidable piece 1670 may also serve to indicate or measure the distance of the K-wire 1600 above the plate 100, 200, 2780, 289, 290, 291 such as in conjunction with a dimensional scale that may be displayed on the alignment guide 1650.

The slideable piece 1670 may move freely with respect to K-wire alignment guide 1650, or may move less than freely. The slideable piece 1670 may have some continuous friction for motion with respect to K-wire alignment guide 1650, that exists for all such motion. It is also possible that the motion of slideable piece 1670 may have discrete preferred locations. Such locations may be uniformly spaced. The motion may be such that slideable piece 1670 snaps into the preferred locations on K-wire alignment guide 1650, with an increased amount of force to leave those locations. It is possible that both continuous friction and discrete preferred locations may exist. It is possible that any such motion can have tactile feedback. It is possible that motion into or out of the discrete locations can have tactile feedback or audible feedback or both.

During use, typically, a K-wire 1600 may extend, and may be supported at both ends by respective support posts 1620 or similar structures attached to the plate 100, 200, 270, 289, 290, 291. The use of support posts 1620 at both ends of the K-wire 1600 may reflect the fact that a K-wire 1600 is typically narrower and not very stiff, so support at both ends is more important at least for reacting against bending.

Furthermore, it is even possible that the support posts 1620 may be stiff enough so that when both ends of the K-wire 1600 are clamped in their respective support posts 1620, which in turn are attached to a common plate 100, 200, 270, 289, 290, 291, the K-wire 1600 may be maintained in tension. Devices for applying such tension are described elsewhere herein.

The K-wire alignment guide 1650 may provide a stable surface for the K-wire 1600 during insertion into the patient. There could be provided a shelf that the K-wire 1600 could rest on. The K-wire alignment guide may measure the height of the K-wires above the plate 100, 200. This may make the surgical technique easier and may help provide for more precise placement of the K-wires into the bone. The K-wire alignment guide 1650 may comprise a measurement scale to measure the height of the K-wire above the plate 100, 200, which may help the surgeon in the clamping of the K-wires.

In embodiments of the invention, one or more support posts can be attached to the plate 100, 200s to secure other components and to provide for the placement of attachments at levels other than at the level of the plate 100, 200, 270, 289, 290, 291. As shown in FIG. 16B, 16C, the support post 1620 may contain a slot 1622 for this attachment, with the slot 1622 being oriented so that its length is generally along the longitudinal direction of the apparatus. The slot 1622 may allow for unlimited adjustment of the position of the attachment along the longitudinal direction of the support post 1620, as compared to what would be provided by a support post that might contain individual separate holes, which would only allow very limited and discrete attachment locations.

As yet another possibility, the support post 1620 could contain multiple overlapping holes, which would allow for finer adjustment than discrete holes, although it still would not allow continuous adjustment as would be the case for a slot 1622.

Such a support post 1620 may be used to hold either a K-wire 1600 or a half-pin, or still other fixation hardware. Such a support post 1620 may provide adjustability of position in any one or more degrees of freedom, and may further provide the ability to lock such hardware rigidly in place after desired positioning has been achieved. Such a support post 1620 with a K-wire holder, universal fixation bolt 2100, is illustrated in FIG. 16C. The same universal fixation bolt 2100 is also illustrated elsewhere herein attached directly to a plate 100, 200, 270, 289, 290, 291.

Referring now to FIG. 17, a half-pin 1700 may be a longitudinal structure configured at one of its ends 1710 to attach to bone or a piece of bone, and able to be grasped or supported at another place along its length. The half-pin 1700 may be generally straight. There is no need for the half-pin 1700 to be of uniform dimension or shape along its length. The half-pin 1700 may include a tip 1710 and, proximally of the tip 1710, a middle region or held region 1720, and, proximally of the middle region or held region 1720, a proximal region 1730. The tip 1710 may be pointed and may include threads 1712, which may be self-tapping suitable to tap into bone or a fragment of bone. A half-pin 1700 may have a first or bone attachment diameter at its tip 1710, which may be a major diameter of the threads 1712 in a non-tapered region of the threads 1712. The middle region or held region 1720 may be generally cylindrical and may have a second diameter. Alternatively, the middle region or held region 1720 may have any desired cross-sectional shape and may have a maximum cross-sectional dimension. The middle region or held region 1720 may be configured to be received and held in a support structure. Finally, at its most proximal end 1730, the half-pin 1700 may have a proximal region that may have a tool engagement feature 1732 suitable to be grasped by a tool such as a driving tool (not illustrated). The tool engagement feature 1732 may, as illustrated, include a flat along a side of the proximal region 1730, and may, as illustrated, further include a circumferential groove that may intersect the flat.

The middle region or held region 1720, may be larger than the first diameter at its bone attachment end or tip 1710 or the maximum cross-sectional dimension of the tip 1710. The diameter or overall lateral dimension of the proximal end 1710 may have any desired relationship to the second diameter or maximum cross-sectional dimension, i.e., it may as illustrated be less than the second diameter or maximum cross-sectional dimension, but alternatively it could be greater than or equal to the second diameter.

There may be provided a plurality of half-pins 1700, which may have varying bone attachment diameters or features at the bone attachment end or tip 1710. At the same time, various half-pins 1700 may have identical second diameters or maximum cross-sectional dimension. The use of identical second diameters or maximum cross-sectional dimension would enable interchangeability, i.e., various half-pins 1700 could be used in a single support structure without the need for any adapter, or by changing the support structure. If a variety of differently-dimensioned half-pins 1700 is provided, it is possible that the second diameter or maximum cross-sectional dimension of the various half-pins 1700 could be greater than the largest first diameter or cross-sectional dimension of any of the half-pins 1700. It is also possible that various half-pins 1700 could have identical proximal ends, thereby being universally compatible with a driving tool.

It is further possible that if a variety of half-pins 1700 is provided, the overall lengths could differ among various half-pins 1700.

FIG. 17A shows a half-pin 1700. FIG. 17B is a close-up view of the tip 1710. FIG. 17C is a close-up view of the proximal end 1730. FIG. 18A shows a half-pin 1700 as supported in its support structure (although for simplicity of illustration, the associated plate is omitted). The support structure may be such as to allow adjustability in various degrees of freedom when loose, and may rigidly fix the half-pin 1700 when tight. FIG. 18B shows a half-pin 1700 as supported in its support structure including the associated ring or plate.

Referring now to FIGS. 19A and 19B, it is further possible that half-pins 1700 may be secured in a device that may be referred to as block 1760. Block 1760 may have a shape generally of a parallelepiped and may have at least some of its faces parallel to others of its faces. Block 1760 may have holes through it that intersect in three mutually perpendicular directions. As illustrated, holes in one of the three mutually perpendicular directions are internally threaded, suitable to accept a setscrew. Holes in another one of the directions may be unthreaded and may have an internal diameter that is suitable to receive the various half-pins 1700. The bolts or setscrews that screw into threaded holes in block 1760 may be suitable to tighten down on and anchor the half-pins 1700 to the block 1760. Block 1760 is illustrated as having four rows of holes in a particular lengthwise direction, although of course other numbers are possible also, and blocks 1760 of more than one size may be provided in the form of a kit. This illustrates that pieces of hardware such as half-pins 1700 may be anchored in more than one ways using different pieces of anchoring hardware. This allows the overall fixation system to be versatile and adapt to a wide variety of surgical situations as dictated by the conditions of individual patients.

FIG. 19C shows a connecting plate 1780 that has a 90 degree twist. Such a plate 1780 can be used for any of various instances of connecting components described herein to various other components. Connecting plate 1780 may have holes therethrough whose axes may appear to be perpendicular to each other when viewed from along the lengthwise direction of connecting plate 1780

Referring now to FIGS. 20A-20C and 21A-21B, the K-wires 1600 may be secured to the plates 100, 200, 270, 289, 290, 291 with universal fixation bolts 2100. The universal fixation bolt 2100 may extend through the plate 100, 200, 270, 289, 290, 291 and may be secured with a nut.

In this embodiment the head of the universal fixation bolt 2100 comprises a shaft 2110 that is at least partially threaded, and comprises a head 2120 connected to the shaft 2110 and larger than the shaft 2110. The universal fixation bolt 2100 further may have a cross-hole 2130 through the shaft 2110 substantially perpendicular to the long axis of the shaft 2110. This cross-hole 2130 may be of a diameter or internal cross-sectional dimension suitable to accept a K-wire 1600 therethrough. The cross-hole 2130 is illustrated as being a round hole. However, alternatively its cross-sectional shape could be square, rectangular, triangular, V-shaped or diamond-shaped, a portion of a hexagon, or arbitrarily curved, circular arc, oval, curved, triangular, diamond-shaped, square, rectangular, wavy, spline-shaped, or any other desired shape.

Additionally, the universal fixation bolt 2100 may have a groove 2140 on the underside of the head 2120, with the groove 2140 also being dimensioned suitably to accept the K-wire 1600. The groove 2140 is illustrated as being, in cross-section, an arc of a circle. However, the cross-sectional shape of the groove 2140 could alternatively be square, rectangular, triangular, V-shaped or diamond-shaped, a portion of a hexagon, or arbitrarily curved, circular arc, oval, curved, triangular, diamond-shaped, square, rectangular, wavy, spline-shaped, or any of many other shapes or any other desired shape. The groove 2140 may be substantially parallel to the cross-hole 2130. The K-wire 1600 can be inserted through the cross-hole 2130 or can be placed in the groove 2140, and can be secured when the nut is tightened against a plate 100, 200, 270, 289, 290, 291 thereby pulling the head 2120 towards plate 100, 200, 270, 289, 290, 291 sufficiently to anchor the K-wire 1600.

It is possible that the groove 2140 can have a cross-sectional shape that is a portion of a circle having a groove radius, and the cross-hole 2130 can have a hole radius, and the groove radius can substantially equal the hole radius. More generally, the groove 2140 can have a cross-sectional dimension that is substantially equal to the cross-sectional dimension of the cross-hole 2130.

Although in the illustration the cross-hole 2130 and the groove 2140 are shown as being parallel to each other, in general the cross hole 2130 and the groove 2140 could be at any angle relative to each other.

FIG. 21A shows the universal fixation bolt 2100 in isolation. FIG. 21B shows the universal fixation bolt 2100 together with a plate 100, 200, 270, 289, 290, 291 holding a K-wire 1600 in side groove 2140. FIG. 21C shows the universal fixation bolt 2100 together with a plate 100, 200, 270, 289, 290, 291 holding a K-wire 1600 in the cross-hole 2130.

It is also possible that the universal fixation bolt 2100 could be attached to a post that is in turn attached to a plate.

The post and the plate may have compatible dimensions so that a single universal fixation bolt 2100 could be used with both of them.

Referring now to FIGS. 22A-22C, there are certain situations in which use of a K-wire 1600 may involve use of a tensioning device. A tensioning device 2220 (shown in FIG. 22A) may in turn be used with a tensioning adapter 2210 that may be attached to plate 100, 200, 270, 289, 290, 291. The tensioning device 2220 may contact and react its applied tension force against the tensioning adapter 2210. In connection with this, there may be certain situations in which it may be desirable to supplement the tensioning adapter 2210 with a filler-alignment piece 2230. Such situations can arise when the tensioning adapter 2210 is positioned partly over an outrigger and partly over a region that does not contain an outrigger. In such a situation, it may be desirable to essentially fill the region that does not contain an outrigger so that it has a radial extent substantially similar to that of the outrigger region. Thus, a filler-alignment piece 2230 may be provided. The filler-alignment piece 2230 may be capable of attaching to plate 100, 200, 270, 289, 290, 291 and may have a thickness similar to that of plate 100, 200, 270, 289, 290, 291 and may have a radial dimension suitable to bring the non-outrigger portion of plate 100, 200, 270, 289, 290, 291 out to a radial dimension similar to that of outrigger 120, 220.

Filler-alignment piece 2230 may be such that it can maintain desired relative positions of certain pieces during tensioning. The filler-alignment piece 2230 may, first of all, have a slot 2238 therethrough that can receive a plate 100, 200, 270, 289, 290, 291. The slot 2238 may have a slot width that is just slightly larger than the thickness of plate 100, 200, 270, 289, 290, 291. The innermost or bottom surface of the slot may be complementary to an outer surface of plate 100, 200, 270, 289, 290, 291 or to an outrigger of plate 100, 200, 270, 289, 290, 291 or to a combination of an outrigger of plate 100, 200, 270, 289, 290, 291 and filler-alignment piece 2230. As illustrated, the slot may be effectively formed by the presence of various of legs 2241A, 2241B, 2241C and 2241D, although other designs are of course possible. With respect to the two legs 2241A, 2241B that are illustrated as being above the plate 100, 200, 270, 289, 290, 291 the two legs may have surfaces that face each other that in at least some places are substantially flat and parallel to each other having an internal gap width. The internal gap width may be just slightly wider than the external flat-to-flat dimension of the head of the universal fixation bolt 2100. With this interrelationship, the tensioning adapter 2210 can serve as a counter-torque wrench during tightening of the nut on the universal fixation bolt 2100. With respect to the two legs 2241B, 2241C that are illustrated as being below the plate 100, 200, 270, 289, 290, 291 those two legs 2241B, 2241C may be spaced apart by a sufficient distance and shape so as to allow a nut to be placed on threaded rod or universal fixation bolt 2100 and to be rotated into its final position on threaded rod or universal fixation bolt 2100. Furthermore, the two legs 2241B, 2241C may be spaced apart by a sufficient distance and shape so as to allow a wrench socket or similar gripping device (not shown) to grasp a nut (not shown) on the threaded rod or universal fixation bolt 2100 in order to tighten the nut.

Tensioning adapter 2210 may further have a hole 2245 therethrough that is greater than a diameter of K-wire 1600, through which K-wire 1600 may pass. Such hole 2245 may be tapered, such as frustoconical, being wider closer to plate 100, 200, 270, 289, 290, 291 and narrower further away from plate 100, 200, 270, 289, 290, 291. At its most proximal end, plate 100, 200, 270, 289, 290, 291 may have an interface or a bearing surface suitable for tensioning device 2200 to bear against. Such interface may include a surface that is substantially perpendicular to an axis of hole 2245.

The features of tensioning adapter 2210 may be such that in the presence of an outrigger on plate 100, 200, 270, 289, 290, 291 the tensioning adapter 2210 may cooperate with filler-alignment piece 2230 to provide adequate positioning and support of tensioning adapter 2210. When tension is being applied to K-wire 1600, tensioning adapter 2210 may bear against plate 100, 200, 270, 289, 290, 291 or against filler-alignment piece 2230 or both, and tensioning device 2200 may bear against tensioning adapter 2210.

The plates 100, 200, 270, 289, 290, 291 may encircle the patient's leg or foot, and the K-wires 1600 and half-pins 1700 may be inserted into the bone and may be connected to the plates 100, 200, 270, 289, 290, 291 either directly or indirectly. After attaching the K-wires 1600 to the plates 100, 200, 270, 289, 290, 291, the K-wires 1600 may have tension applied to them. This may be done by first securing one end of the K-wire 1600 to the plates 100, 200, 270, 289, 290, 291 with a universal fixation bolt 2100. Next, a tensioning instrument 2220 may be used to apply a tension to the K-wire 1600, which may be followed by securing another universal fixation bolt 2100 to the plates 100, 200, 270, 289, 290, 291 on the other end of the K-wire 1600. The wire tensioner 2220 may have an engagement tip. In this embodiment, the engagement tip has four forks or prongs 2241A, 2241B, 2241C, 2241D that engage both the ring 100, 200, 270, 289, 290, 291 and the universal fixation bolt 2100 simultaneously while allowing for the K-wire 1600 to extend through to the tensioner 2220. It also allows for a shift in alignment of the K-wire 1600 as well as space for a wrench on a tightening nut. This provides alignment and stabilization to the ring 100, 200, 270, 289, 290, 291 while holding the universal fixation bolt 2100 from rotating during tightening.

Since the tensioning adapter 2210 holds the universal fixation bolt 2100 while aligned with the plate 100, 200, 270, 289, 290, 291 there is no need for an extra wrench to prevent universal fixation bolt 2100 from rotating, which frees up a surgeon's hand for other use. The tensioning adapter 2210 may also prevent rotation of the universal fixation bolt 2100 during tightening.

In embodiments of the invention, it is possible to provide a retention device 2310, which may also be referred to as a coin. Such a retention device 2310 may be suitable to be positioned on a longitudinal bone connection device such as a K-wire 1600 or on a half-pin 1700, outside the patient's body, and may be suitable to maintain its position on the K-wire 1600 or on the half-pin 1700 such as by friction. As such, it may be able to frictionally maintain its position on one of said longitudinal bone connection devices sufficiently to retain a dressing against a patient's limb.

After the K-wires 1600 or half pins 1700 are inserted through the patient's skin and into the bone, then gauze, with medication, may be placed against the skin at the entrance point of the K-wire or half-pin. The retention device 2310 may slide along the K-wire 1600 or half-pin 1700 and may hold the gauze or similar substance against the patient's skin so that the medication can stay in place.

The retention device 2310 may be suitable to be placed onto or removed from the longitudinal bone connection device such as a K-wire 1600 or half-pin 1700 without access to any end of the K-wire 1600 or half-pin 1700. Accordingly, the retention device 2310 may have therethrough one or more passageways 2320. The passageway 2320 may in cross-section be a complete or partial circle, but it alternatively could have other shapes. It could in cross-section be circular arc, oval, curved, triangular, diamond-shaped, square, rectangular, wavy, spline-shaped, or any of many other shapes, as long as it has some contact with the longitudinal bone connection device.

The passageway 2320 may have a complete perimeter of a hole, or may have a partial perimeter. A partial perimeter may have at least one slot 2330 or cut interruption in its perimeter. For example the passageway 2320 may comprise more than half of a perimeter of a circle while still connecting to the exterior of the retention device 2310. For example the passageway 2320 may comprise more than 180 degrees but less than 360 degrees of circumference. It is further possible that the slot may form an access corridor that connects the passageway with the exterior of the retention device 2310. The access corridor 2330 may be tapered, being wider toward the exterior circumference of the retention device 2310 and smaller near where the access corridor 2330 meets the passageway 2320. Such tapering may help the ease of applying the retention device 2310 to the K-wire 1600 or half-pin 1700. Stated differently, the width of the access corridor 2330 or cut at or near the hole itself may be less than the diameter of the hole that it provides access to.

More than one such passageway 2320 may be provided in a given retention device 2310, and the passageways 2320 may be of different sizes. Differently sized passageways 2320 may correspond to a K-wire 1600 and to a half-pin 1700, or to different sizes of K-wires 1600 or half-pins 1700 or any similar component. The passageway 2320 that corresponds to a particular K-wire 1600 or half-pin 1700 may have an internal diameter or dimension in a relaxed condition that is slightly smaller than the outside diameter of the K-wire 1600 or half-pin 1700 that it is intended to be used with. In this way, it may be useful for the retention device 2310 to deform or stretch slightly, which may result in some friction of the retention device 2310 with respect to the associated K-wire 1600 or half-pin 1700.

If desired, it is also possible for the retention device 2310 to have a combination of one or more passageways 2320 that lack any interruption or cut or access corridor through their perimeter, and one or more passageways 2320 that have an interruption or cut or access corridor 2330 through their perimeter.

It is further possible that around the perimeter of any of the passageways 2320 or holes, the thickness of the retention device 2310 may be greater than the thickness in places away from the passageways. Also, as illustrated, the thickness of the retention device 2310 may be greater at the outer edge of the retention device 2310 than it is at radially intermediate regions. In general, the thickness of retention device 2310 may be either constant or non-constant. The thickness of the retention device 2310 at ordinary regions (not near the passageways 2320 or the outer edge) may be chosen, together with the material properties, such that it is possible to warp one edge of the passageway 2320 out of the plane of the rest of the retention device 2310. This may aid in the removal of the device from the K-wire 1600 or half-pin 1700, or in loosening its grip on the K-wire 1600 or half-pin 1700 for purposes of repositioning the retention device 2310.

The retention device 2310 may be resilient and may be made of resilient polymer such as silicone.

In using the retention device 2310, it is possible to slide the retention device 2310 onto the K-wire or half-pin in a lateral direction, with the K-wire 1600 or half-pin 1700 passing through the access corridor 2330. In using the retention device 2310, it is also possible to slide the retention device 2310 along the lengthwise dimension of a K-wire 1600 or a half-pin 1700 so as to use the retention device 2310 to push or maintain a barrier material such as medical gauze against the patient's skin near the point where the half-pin or K-wire passes through the patient's skin. Such gauze or other medical material may be ordinary sterile material or may further comprise an antimicrobial substance so as to reduce the risk of infection at the site where the K-wire 1600 or half-pin 1700 passes through the patient's skin. The retention device 2310 can be used with any type of barrier or whether it is medicated or not.

Referring now to FIGS. 23C-23E, in an embodiment of the invention, the retention device 2310 may comprise flaps 2340 that extends generally from a hole perimeter radially inward toward whatever half-pin or K-wire is desired to be gripped by the retention device 2310. The flaps may be distributed on around the perimeter of the hole. The flaps 2340, in the absence of bearing against a half-pin 1700 or K-wire 1600, may extend radially inwardly to a radius that is smaller than the radius of the corresponding half-pin 1700 or K-wire 1600. The flaps 2340 may be bendable or deformable so that in the presence of the half-pin 1700 or K-wire 1600, the flaps 2340 bend or buckle. The flaps 2340 may have a curvature of the flaps 2340 when the flaps 2340 are in an unstrained condition even in the absence of a half-pin 1700 or K-wire 1600. This curvature may determine a preferred direction of bending or buckling. In regard to the bending or buckling of the flaps 2340, the flaps in FIGS. 23C-23E are shown as they would look after the retention device 2310 has been advanced toward the patient's limb. The flaps 2340 may be suitable so that they allow axial motion of the retention device 2310 (relative to the half-pin 1700 or K-wire 1600) in a particular direction to be easier than axial motion in the opposite direction. For the orientation as illustrated in FIGS. 23C-23E, the direction of easy motion would be for the retention device 2310 to slide toward the distal end of the half-pin 1700, i.e., vertically upward in the illustrated orientation. Sliding the retention device 2310 proximally, or vertically downward as illustrated, would be more difficult. As an alternative, the flaps 2340 could form a continuous web.

It is still further possible that removing the retention device 2310 from the half-pin 1700 might not be particularly difficult, because the existence of access corridor 2330 would allow the retention device 2310 to be deformed out-of-plane in a motion that could be described as peeling. Such a technique might depend on how thick the retention device 2310 is in appropriate places.

In this illustration, most of the flaps are shown, but the half-pin is not shown, but the flaps are shown as they would appear when deflected to accommodate a little bit of interference with the half-pin, with coin having most recently moved in a specific direction with respect to the half-pin, i.e. probably with the coin pushing toward the patient's limb.

A kit may include more than one K-wire, which may be of varying dimensions. A kit may include more than one half-pin, which may be of varying dimensions.

Fine adjustment can be used for distraction osteogenesis (the Ilizarov technique) as well as simply for adjusting the position of bones.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All documents referred to herein are incorporated by reference in their entirety.

We claim:

1. An external fixation system, comprising:
   a first plate;
   a second plate;
   a first fastener connecting said first plate to said second plate;
   wherein at least one of said first plate and said second plate has an external shape that comprises one or more outrigger regions that extends further radially outward than a remainder of said external shape, and said one or more outrigger region comprises at least one through-hole having a complete perimeter and also has at least one slot that opens to an external perimeter of the at least one of said first plate and said second plate;
   wherein said first fastener can connect either to said at least one slot or to said at least one through-hole;
   a speed-nut, and wherein said first fastener includes a threaded rod having a threaded rod axis, and wherein said speed-nut urges said first fastener into tight relationship with at least one of said first plate and said second plate, said speed-nut having a speed-nut axis, wherein when said speed-nut axis is aligned with said threaded rod axis, said speed-nut engages threads of said threaded rod, but when said speed-nut axis is tilted with respect to said threaded rod axis, said speed-nut is free of said threads of said threaded rod; and
   a washer set comprising a first washer having a concave surface, and a second washer having a convex surface, wherein said convex surface and said concave surface are complementary to each other and permit said first washer and said second washer to occupy a tilted orientation relative to each other when said speed-nut bears against said washer set.

2. The external fixation system of claim 1 wherein said first plate is a footplate.

3. The external fixation system of claim 2 further comprising a rocker plate, wherein said footplate includes a regularly repeating pattern of holes for at least one first fastener to connect to, and a plurality of other holes that are not part of said regularly repeating pattern of holes; and
a plurality of spacers that connect said rocker plate to said footplate, wherein said spacers connect to said other holes.

4. The external fixation system of claim 1 wherein said first fastener is a connector, wherein said connector includes a lengthwise adjustable member.

5. The external fixation system of claim 1 further comprising at least one of a universal fixation bolt, a tensioning adaptor, an alignment guide, and a holder, wherein said holder attaches at least one half-pin to at least one of said first plate and said second plate.

6. The external fixation system of claim 1 further comprising an alignment spacer that attaches to or bears against said first plate in a non-outrigger region of said first plate, and extends radially outward approximately to a radial extent of said outrigger region.

7. The external fixation system of claim 1 wherein said first washer has a first substantially flat surface opposite said concave surface and said second washer has a second substantially flat surface second substantially flat surface opposite said convex surface, and said first substantially flat surface and said second substantially flat surface can occupy a tilted orientation with respect to each other when said speed-nut bears against said washer set.

8. The external fixation system of claim 1 wherein said concave surface and said convex surface are portions of spheres.

9. The external fixation system of claim 1 further comprising a provisional alignment clamp, wherein said provisional alignment clamp has a first end that can attach to at least one of said first plate and said second plate and, and has a second end, opposed to said first end, that has a shape complementary to a body part of a patient, and, between said first end and said second end, has a length adjustment mechanism that allows a length of said provisional alignment clamp to lengthen upon pulling said second end away from said first end, but prevents shortening of said length of said provisional alignment clamp.

10. An external fixation system, comprising:
a first plate;
an alignment guide for a K-wire; and
a slidable piece that is slidable along a length of said K-wire alignment guide,
wherein said K-wire alignment guide attaches directly or indirectly to said first plate, and comprises a slot therethrough extending generally along a length of said K-wire alignment guide; and
wherein said slot comprises a portion having a width, said width being larger than a diameter of said K-wire, and said slot further comprises an enlarged portion, said enlarged portion being wider than said width of said portion of said slot.

11. The system of claim 10 wherein said slideable piece has continuous friction for motion with respect to said K-wire alignment guide.

12. The system of claim 10 wherein said slideable piece has discrete preferred locations for motion with respect to said K-wire alignment guide.

13. The system of claim 12 wherein said discrete preferred locations have provide tactile feedback or audible feedback or both.

14. The system of claim 10 further comprising a length scale on said K-wire alignment guide, wherein said length scale cooperates with said slideable piece to indicate a position of said slidable piece.

15. The system of claim 10 wherein said slideable piece further comprises a clamping device to clamp said slideable piece with respect to said K-wire alignment guide.

16. The system of claim 10 further comprising a second plate and a plurality of fasteners connecting said first plate with said second plate.

\* \* \* \* \*